United States Patent
Zhang et al.

(10) Patent No.: US 12,162,879 B2
(45) Date of Patent: Dec. 10, 2024

(54) PYRIDOPYRIMIDINE DERIVATIVE, PREPARATION METHOD THEREFOR AND MEDICAL USE THEREOF

(71) Applicants: Jiangsu Hengrui Medicine Co., Ltd., Lianyungang (CN); Shanghai Hengrui Pharmaceutical Co., Ltd., Shanghai (CN)

(72) Inventors: Guobao Zhang, Shanghai (CN); Yiqian Chen, Shanghai (CN); Feng He, Shanghai (CN); Weikang Tao, Shanghai (CN)

(73) Assignees: Jiangsu Hengrui Medicine Co., Ltd., Lianyungang (CN); Shanghai Hengrui Pharmaceutical Co., Ltd., Shanghai (CN)

( * ) Notice: Subject to any disclaimer, the term of this patent is extended or adjusted under 35 U.S.C. 154(b) by 916 days.

(21) Appl. No.: 17/257,172

(22) PCT Filed: Jul. 2, 2019

(86) PCT No.: PCT/CN2019/094310
§ 371 (c)(1),
(2) Date: Dec. 30, 2020

(87) PCT Pub. No.: WO2020/007275
PCT Pub. Date: Jan. 9, 2020

(65) Prior Publication Data
US 2021/0269439 A1  Sep. 2, 2021

(30) Foreign Application Priority Data

Jul. 3, 2018 (CN) .......................... 201810717585.7
Nov. 7, 2018 (CN) .......................... 201811317059.8

(51) Int. Cl.
C07D 471/04 (2006.01)
A61P 35/00 (2006.01)

(52) U.S. Cl.
CPC ............ *C07D 471/04* (2013.01); *A61P 35/00* (2018.01)

(58) Field of Classification Search
CPC .................................................. C07D 471/04
See application file for complete search history.

(56) References Cited

U.S. PATENT DOCUMENTS

| | | |
|---|---|---|
| 2005/0049274 A1 | 3/2005 | Wall et al. |
| 2008/0009507 A1 | 1/2008 | Cosford et al. |
| 2013/0109639 A1* | 5/2013 | Hughes ............... A61P 13/00 558/275 |
| 2013/0109693 A1* | 5/2013 | Routier ............... C07D 471/04 544/212 |
| 2016/0289229 A1 | 10/2016 | Aktoudianakis et al. |

FOREIGN PATENT DOCUMENTS

| | | |
|---|---|---|
| CN | 1867334 A | 11/2006 |
| CN | 101115479 A | 1/2008 |
| CN | 107108615 A | 8/2017 |
| EA | 201791305 A1 | 12/2017 |
| WO | 2006135993 A1 | 12/2006 |
| WO | 2007024612 A2 | 3/2007 |
| WO | 2009111337 A1 | 9/2009 |
| WO | 2011017611 A1 | 2/2011 |
| WO | 2011068233 A1 | 6/2011 |
| WO | 2011139348 A2 | 11/2011 |
| WO | 2012066336 A1 | 5/2012 |
| WO | 2012156498 A1 | 11/2012 |
| WO | 2013033345 A1 | 3/2013 |
| WO | 2016105532 A1 | 6/2016 |
| WO | 2016141092 A1 | 9/2016 |
| WO | 2017046112 A1 | 3/2017 |
| WO | 2017048727 A1 | 3/2017 |

OTHER PUBLICATIONS

Pinedo et al. (2000).*
McMahon et al. (2000).*
Written Opinion of the International Searching Authority; China National Intellectual Property Administration; International Application No. PCT/CN2019/094310; Sep. 27, 2019; 7 pages.

(Continued)

*Primary Examiner* — Paul V Ward
(74) *Attorney, Agent, or Firm* — Taft Stettinius & Hollister LLP

(57) ABSTRACT

Disclosed are a pyridopyrimidine derivative as shown in general formula (I), a preparation method therefor and a pharmaceutical composition containing the derivative, and the use thereof as a therapeutic agent, particularly as a TLR8 agonist, wherein each substituent of general formula (I) is the same as those defined in the description.

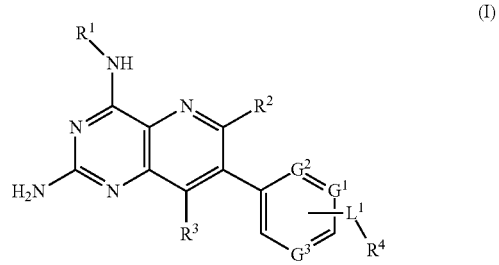

(I)

19 Claims, No Drawings

(56) References Cited

OTHER PUBLICATIONS

International Preliminary Report on Patentability; China National Intellectual Property Administration; International Application No. PCT/CN2019/094310; Jan. 5, 2021; 9 pages.
International Search Report; China National Intellectual Property Administration; International Application No. PCT/CN2019/094310; Oct. 9, 2019; 10 pages.
Ranjeet Singh Mahla et al.; Sweeten PAMPs: Role of Sugar Complexed PAMPs in Innate Immunity and Vaccine Biology; Frontiers in Immunology; Sep. 2, 2013; 16 pages; vol. 4, Article 248.
Extended European Search Report, European Patent Office, European Patent Application No. 19830329.9, Mar. 14, 2022, 7 pages.
Russian Office Action, Federal Service for Intellectual Property, Russian Patent Application No. 2021100972/04 (001793), Feb. 10, 2022, 10 pages.

* cited by examiner

PYRIDOPYRIMIDINE DERIVATIVE, PREPARATION METHOD THEREFOR AND MEDICAL USE THEREOF

CROSS-REFERENCE TO RELATED APPLICATIONS

This application is a U.S. National Phase of International PCT Application No. PCT/CN2019/094310 filed Jul. 2, 2019, which claims priority to Chinese Patent Application Serial No. 201810717585.7 filed Jul. 3, 2018 and Chinese Patent Application Serial No. 201811317059.8 filed Nov. 7, 2018, the contents of each application are incorporated herein by reference in their entirety.

FIELD OF THE INVENTION

The present invention belongs to the field of medicine, and relates to a pyridopyrimidine derivative of formula (I), a method for preparing the same and a pharmaceutical composition comprising the same, as well as the use thereof as a therapeutic agent, particularly as a TLR8 agonist.

BACKGROUND OF THE INVENTION

Toll-like receptors (TLRs) are a class of key receptors involved in innate immunity. TLRs are single, membrane-spanning, non-catalytic receptors, usually expressed on sentinel cells such as macrophages and dendritic cells, and can recognize structurally conserved molecules produced by microorganisms. Once these microorganisms break through physical barriers such as the skin or intestinal tract mucosa, they will be recognized by TLRs, thereby activating immune cell responses (Mahla, R S. et al., Front Immunol. 4: 248 (2013)). The ability of immune system to broadly recognize pathogenic microorganisms is, in part, due to the widespread presence of Toll-like immunoreceptors.

There are at least ten different TLRs in mammals. Ligands and corresponding signaling cascades have been identified for some of these receptors. TLR8 is a member of the subgroup of TLRs (TLRs 3, 7, 8, and 9), which is localised in recognizing the endosomal compartment of cells which are specialised to detect non-self nucleic acids. In human, TLR8 is mainly expressed in monocytes, NK cells and myeloid dendritic cells (mDC). TLR8 agonists can cause the release of various pro-inflammatory cytokines, such as IL-6, IL-12, TNF-α and IFN-γ.

TLR8 plays an important role in the body's innate immunity and acquired immunity. TLR8 agonists, as immunomodulators, can be used in the treatment of various immune-related diseases, such as ovarian cancer, melanoma, non-small cell lung cancer, hepatocellular carcinoma, basal cell carcinoma, renal cell carcinoma, myeloma, allergic rhinitis, asthma, chronic obstructive pulmonary disease (COPD), ulcerative colitis, liver fibrosis, HBV, Flaviviridae virus, HCV, HPV, RSV, SARS, HIV or influenza virus infection and the like.

Since TLR8 and TLR7 are highly homologous. TLR8 agonists are also TLR7 agonists in most cases. Therefore. TLR8 and TLR7 dual agonists have been reported in many patent applications, such as WO2009111337, WO2011017611, WO2011068233, WO2011139348, WO2012066336, WO2013033345 and WO2017046112. There are relatively few reports on TLR8 selective agonists, mainly including VTX-2337 developed by VentiRX (WO2007024612) and GS-9688 developed by Gilead (WO2016141092).

SUMMARY OF THE INVENTION

After deep research, the inventors have designed and synthesized a series of pyridopyrimidine compounds. These compounds have a good activating effect on TLR8, while have no activating effect on TLR7. Therefore, these compounds can be developed as TLR8 selective agonists for the treatment and/or prevention of various diseases related to TLR8 activity.

Thus, an object of the present invention is to provide a compound of formula (I);

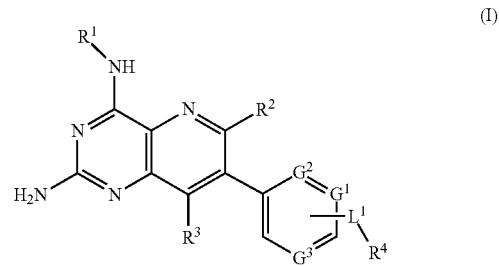

or a tautomer, mesomer, racemate, enantiomer, diastereomer thereof, or mixture thereof, or a pharmaceutically acceptable salt thereof, wherein:
$G^1$, $G^2$ and $G^3$ are identical or different, and are each independently selected from the group consisting of CH, $CR^5$ and N;

$L^1$ is selected from the group consisting of alkylene and covalent bond, wherein the alkylene is optionally substituted by one or more substituent(s) selected from the group consisting of halogen, alkyl, alkoxy, haloalkyl, haloalkoxy, hydroxy, hydroxyalkyl, cyano, amino, nitro, cycloalkyl and heterocyclyl;

$R^1$ is selected from the group consisting of hydrogen atom, halogen, alkyl, alkoxy, haloalkyl, haloalkoxy, hydroxy, hydroxyalkyl, cyano, amino, nitro, cycloalkyl, heterocyclyl, aryl and heteroaryl, wherein the alkyl, cycloalkyl, heterocyclyl, aryl and heteroaryl are each independently optionally substituted by one or more substituent(s) selected from the group consisting of halogen, alkyl, alkoxy, haloalkyl, haloalkoxy, hydroxy, hydroxyalkyl, cyano, amino, nitro, cycloalkyl, heterocyclyl, aryl and heteroaryl;

$R^2$ and $R^3$ are identical or different, and are each independently selected from the group consisting of hydrogen atom, halogen, alkyl, alkoxy, haloalkyl, haloalkoxy, hydroxy, hydroxyalkyl, cyano, amino, nitro, cycloalkyl, heterocyclyl, aryl and heteroaryl;

$R^4$ is selected from the group consisting of alkyl, haloalkyl, cycloalkyl, heterocyclyl, aryl and heteroaryl, wherein the alkyl, cycloalkyl, heterocyclyl, aryl and heteroaryl are each independently optionally substituted by one or more substituent(s) selected from the group consisting of alkyl, alkoxy, halogen, amino, cyano, nitro, hydroxy, hydroxyalkyl, cycloalkyl, heterocyclyl, aryl and heteroaryl; and $R^5$ is selected from the group consisting of hydrogen atom, halogen, alkyl, alkoxy, haloalkyl, haloalkoxy, hydroxy, hydroxyalkyl, cyano, amino, nitro, cycloalkyl, heterocyclyl, aryl and heteroaryl.

In a preferred embodiment of the present invention, the compound of formula (I) according to the present invention is a compound of formula (Ia):

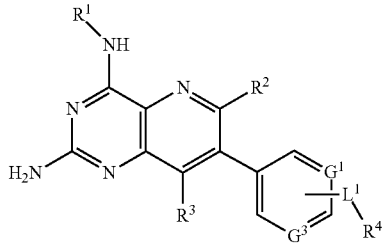

(Ia)

or a tautomer, mesomer, racemate, enantiomer, diastereomer thereof, or mixture thereof, or a pharmaceutically acceptable salt thereof,
wherein:
$G^1$, $G^3$, $L^1$ and $R^1$ to $R^4$ are as defined in formula (I).

In another preferred embodiment of the present invention, the compound of formula (I) according to the present invention is a compound of formula (Ib):

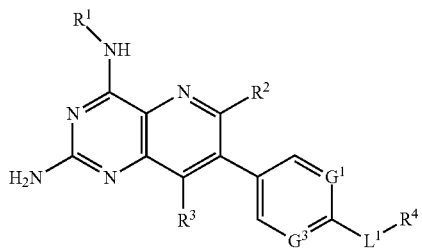

(Ib)

or a tautomer, mesomer, racemate, enantiomer, diastereomer thereof, or mixture thereof, or a pharmaceutically acceptable salt thereof,
wherein:
$G^1$, $G^3$, $L^1$ and $R^1$ to $R^4$ are as defined in formula (I).

In another preferred embodiment of the present invention, the compound of formula (I) according to the present invention is a compound of formula (II):

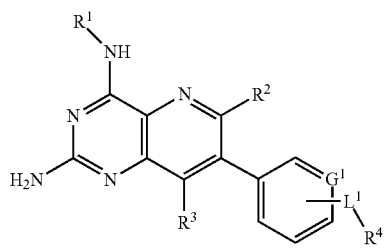

(II)

or a tautomer, mesomer, racemate, enantiomer, diastereomer thereof, or mixture thereof, or a pharmaceutically acceptable salt thereof,
wherein:
$G^1$, $L^1$ and $R^1$ to $R^4$ are as defined in formula (I).

In another preferred embodiment of the present invention, the compound of formula (I) according to the present invention is a compound of formula (III):

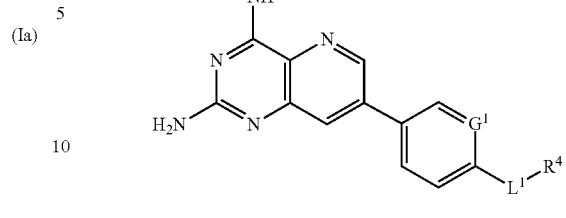

(III)

or a tautomer, mesomer, racemate, enantiomer, diastereomer thereof, or mixture thereof, or a pharmaceutically acceptable salt thereof,
wherein:
$G^1$, $L^1$, $R^1$ and $R^4$ are as defined in formula (I).

In another preferred embodiment of the present invention, the compound of formula (I), formula (Ia), formula (Ib), formula (II) or formula (III) according to the present invention, wherein $R^4$ is a heterocyclyl, which is optionally substituted by one or more alkyl(s); $R^4$ is preferably a 4 to 6 membered heterocyclyl comprising one or two identical or different heteroatom(s) selected from the group consisting of N, O and S, and the 4 to 6 membered heterocyclyl is optionally substituted by one or more alkyl(s); and $R^4$ is more preferably a pyrrolyl, piperazinyl, piperidinyl or morpholinyl.

In another preferred embodiment of the present invention, the compound of formula (I), formula (Ia), formula (Ib), formula (II) or formula (III) according to the present invention is a compound of formula (IVa):

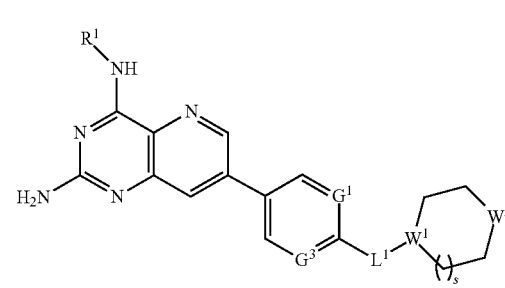

(IVa)

or a tautomer, mesomer, racemate, enantiomer, diastereomer thereof, or mixture thereof, or a pharmaceutically acceptable salt thereof,
wherein:
$W^1$ is CH and $W^2$ is $NR^6$; or
$W^1$ is N and $W^2$ is $CH_2$ or $NR^6$.
$R^6$ is selected from the group consisting of hydrogen atom and alkyl, and preferably alkyl;
s is 0 or 1; and
$G^1$, $G^3$, $L^1$ and $R^1$ are as defined in formula (I).

In another preferred embodiment of the present invention, the compound of formula (I), formula (Ia), formula (Ib), formula (II) or formula (III) according to the present invention is a compound of formula (IV):

(IV)

[Chemical structure of formula (IV)]

or a tautomer, mesomer, racemate, enantiomer, diastereomer thereof, or mixture thereof, or a pharmaceutically acceptable salt thereof,
wherein:
$W^1$ is CH and $W^2$ is $NR^6$; or
$W^1$ is N and $W^2$ is $CH_2$ or $NR^6$;
$R^6$ is selected from the group consisting of hydrogen atom and alkyl, and preferably alkyl;
s is 0 or 1; and
$G^1$, $L^1$ and $R^1$ are as defined in formula (I).

In another preferred embodiment of the present invention, the compound of formula (I), formula (Ia), formula (Ib), formula (II), formula (III), formula (IVa) or formula (IV) according to the present invention, wherein $R^1$ is an alkyl, which is optionally substituted by one or more hydroxy(s); $R^1$ is preferably a $C_{1-12}$ alkyl, which is optionally substituted by one or more hydroxy(s).

In another preferred embodiment of the present invention, the compound of formula (I), formula (Ia), formula (Ib), formula (II), formula (III), formula (IVa) or formula (IV) according to the present invention is a compound of formula (Va):

(Va)

[Chemical structure of formula (Va)]

or a tautomer, mesomer, racemate, enantiomer, diastereomer thereof, or mixture thereof, or a pharmaceutically acceptable salt thereof,
wherein:
$W^1$ is CH and $W^2$ is $NR^6$; or
$W^1$ is N and $W^2$ is $CH_2$ or $NR^6$;
$R^6$ is selected from the group consisting of hydrogen atom and alkyl, and preferably alkyl;
s is 0 or 1; and
$G^1$, $G^3$ and $L^1$ are as defined in formula (I).

In another preferred embodiment of the present invention, the compound of formula (I), formula (Ia), formula (Ib), formula (II), formula (III), formula (IVa) or formula (IV) according to the present invention is a compound of formula (V);

(V)

[Chemical structure of formula (V)]

or a tautomer, mesomer, racemate, enantiomer, diastereomer thereof, or mixture thereof, or a pharmaceutically acceptable salt thereof,
wherein:
$W^1$ is CH and $W^2$ is $NR^6$; or
$W^1$ is N and $W^2$ is $CH_2$ or $NR^6$;
$R^6$ is selected from the group consisting of hydrogen atom and alkyl, and preferably alkyl;
s is 0 or 1; and
$G^1$ and $L^1$ are as defined in formula (I).

In another preferred embodiment of the present invention, the compound of formula (I), formula (Ia), formula (Ib), formula (II), formula (III), formula (IVa), formula (IV), formula (Va) or formula (V) according to the present invention, wherein $L^1$ is —$(CH_2)_n$— or a covalent bond, wherein n is an integer from 1 to 6; and $L^1$ is preferably -$CH_2$— or a covalent bond.

The compounds of formula (I) according to the present invention typically include, but are not limited to:

| Example No. | Structure and name of the compound |
|---|---|
| 1 | 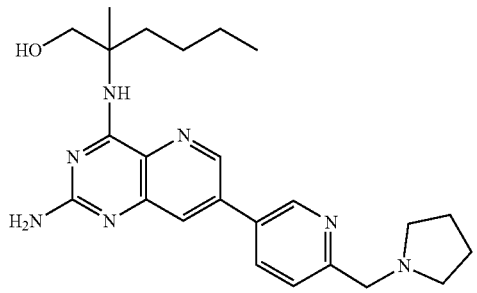<br>1<br>2-((2-Amino-7-(6-(pyrrolidin-1-ylmethyl)pyridin-3-yl)pyrido[3,2-d]pyrimidin-4-yl)amino)-2-methylhexan-1-ol<br>1 |
| 2 | 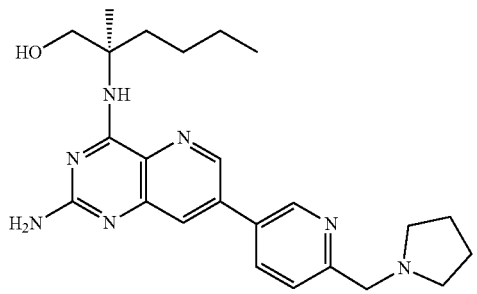<br>2<br>(R)-2-((2-Amino-7-(6-(pyrrolidin-1-ylmethyl)pyridin-3-yl)pyrido[3,2-d]pyrimidin-4-yl)amino)-2-methylhexan-1-ol<br>2 |
| 3 | 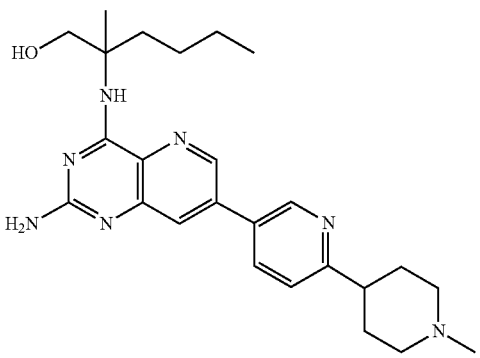<br>3<br>2-((2-Amino-7-(6-(1-methylpiperidin-4-yl)pyridin-3-yl)pyrido[3,2-d]pyrimidin-4-yl)amino)-2-methylhexan-1-ol<br>3 |

-continued
| Example No. | Structure and name of the compound |
|---|---|
| 4 | 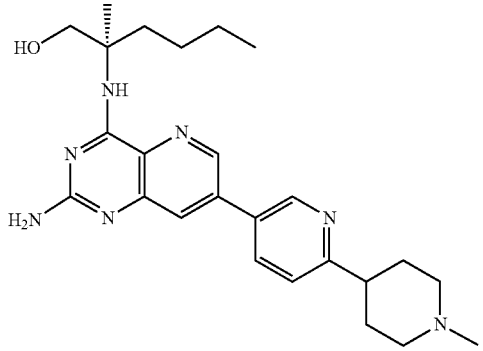<br>4<br>(R)-2-((2-Amino-7-(6-(1-methylpiperidin-4-yl)pyridin-3-yl)pyrido[3,2-d]pyrimidin-4-yl)amino)-2-methylhexan-1-ol<br>4 |
| 5 | 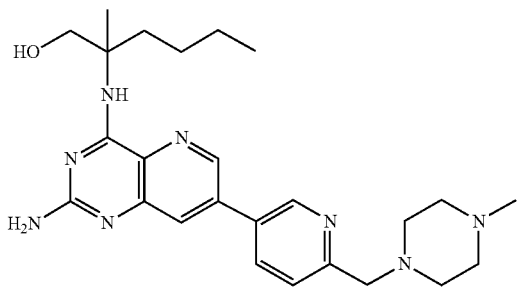<br>5<br>2-((2-Amino-7-(6-((4-methylpiperazin-1-yl)methyl)pyridin-3-yl)pyrido[3,2-d]pyrimidin-4-yl)amino)-2-methylhexan-1-ol<br>5 |
| 6 | 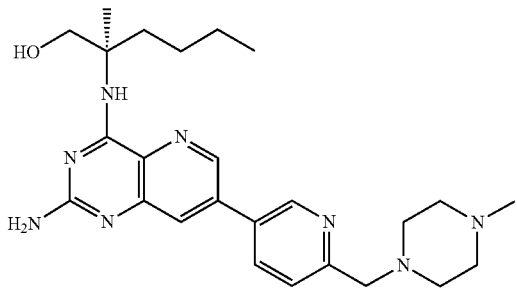<br>6<br>(R)-2-((2-Amino-7-(6-((4-methylpiperazin-1-yl)methyl)pyridin-3-yl)pyrido[3,2-d]pyrimidin-4-yl)amino)-2-methylhexan-1-ol<br>6 |

| Example No. | Structure and name of the compound |
|---|---|
| 7 | 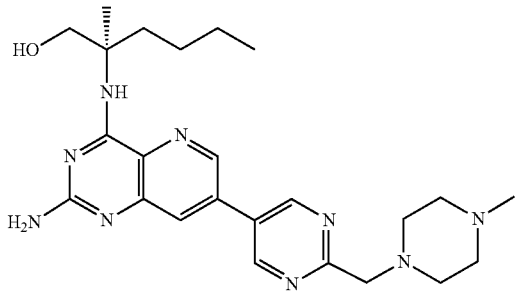<br>(R)-2-((2-Amino-7-(2-((4-methylpiperazin-1-yl)methyl)pyrimidin-5-yl)pyrido[3,2-d]pyrimidin-4-yl)amino)-2-methylhexan-1-ol<br>7 |
| 8 | 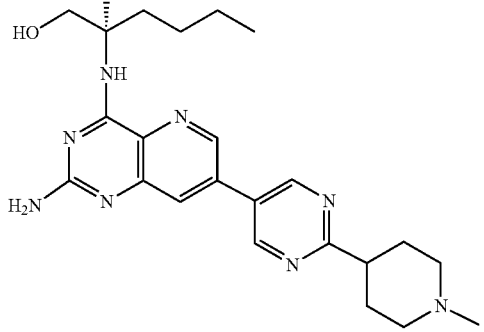<br>(R)-2-((2-Amino-7-(2-(1-methylpiperidin-4-yl)pyrimidin-5-yl)pyrido[3,2-d]pyrimidin-4-yl)amino)-2-methylhexan-1-ol<br>8 |
| 9 | 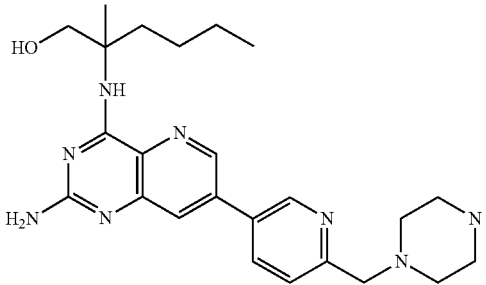<br>2-((2-Amino-7-(6-(piperazin-1-ylmethyl)pyridin-3-yl)pyrido[3,2-d]pyrimidin-4-yl)amino)-2-methylhexan-1-ol<br>9 | or a tautomer, mesomer, racemate, enantiomer, diastereomer thereof, or mixture thereof, or a pharmaceutically acceptable salt thereof.

In another aspect, the present invention relates to a compound of formula (IB):

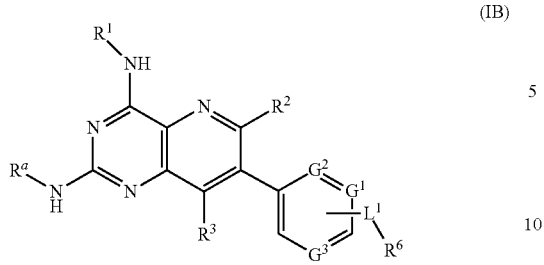

(IB)

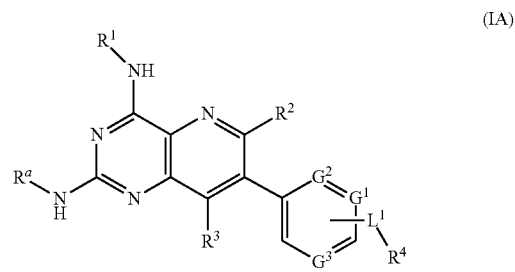

(IA)

or a tautomer, mesomer, racemate, enantiomer, diastereomer thereof, or mixture thereof, or a pharmaceutically acceptable salt thereof, which is an intermediate for preparing the compound of formula (I), wherein:
- $R^a$ is an amino protecting group, and preferably 2,4-dimethoxybenzyl;
- $G^1$, $G^2$ and $G^3$ are identical or different, and are each independently selected from the group consisting of CH, $CR^5$ and N;
- $L^1$ is selected from the group consisting of alkylene and covalent bond, wherein the alkylene is optionally substituted by one or more substituent(s) selected from the group consisting of halogen, alkyl, alkoxy, haloalkyl, haloalkoxy, hydroxy, hydroxyalkyl, cyano, amino, nitro, cycloalkyl and heterocyclyl;
- $R^1$ is selected from the group consisting of hydrogen atom, halogen, alkyl, alkoxy, haloalkyl, haloalkoxy, hydroxy, hydroxyalkyl, cyano, amino, nitro, cycloalkyl, heterocyclyl, aryl and heteroaryl, wherein the alkyl, cycloalkyl, heterocyclyl, aryl and heteroaryl are each independently optionally substituted by one or more substituent(s) selected from the group consisting of halogen, alkyl, alkoxy, haloalkyl, haloalkoxy, hydroxy, hydroxyalkyl, cyano, amino, nitro, cycloalkyl, heterocyclyl, aryl and heteroaryl;
- $R^2$ and $R^3$ are identical or different, and are each independently selected from the group consisting of hydrogen atom, halogen, alkyl, alkoxy, haloalkyl, haloalkoxy, hydroxy, hydroxyalkyl, cyano, amino, nitro, cycloalkyl, heterocyclyl, aryl and heteroaryl;
- $R^6$ is selected from the group consisting of alkyl, haloalkyl, cycloalkyl, heterocyclyl, aryl and heteroaryl, wherein the alkyl, cycloalkyl, heterocyclyl, aryl and heteroaryl are each independently optionally substituted by one or more substituent(s) selected from the group consisting of alkyl, alkoxy, halogen, amino, cyano, nitro, hydroxy, hydroxyalkyl, tert-butoxycarbonyl (BOC), cycloalkyl, heterocyclyl, aryl and heteroaryl; and
- $R^5$ is selected from the group consisting of hydrogen atom, halogen, alkyl, alkoxy, haloalkyl, haloalkoxy, hydroxy, hydroxyalkyl, cyano, amino, nitro, cycloalkyl, heterocyclyl, aryl and heteroaryl.

In a preferred embodiment, the compound of formula (IB) according to the present invention is a compound of formula (IA):

or a tautomer, mesomer, racemate, enantiomer, diastereomer thereof, or mixture thereof, or a pharmaceutically acceptable salt thereof, being an intermediate for preparing the compound of formula (I), wherein:
- $R^a$ is an amino protecting group, and preferably 2,4-dimethoxybenzyl;
- $G^1$, $G^2$ and $G^3$ are identical or different, and are each independently selected from the group consisting of CH, $CR^5$ and N;
- $L^1$ is selected from the group consisting of alkylene and covalent bond, wherein the alkylene is optionally substituted by one or more substituent(s) selected from the group consisting of halogen, alkyl, alkoxy, haloalkyl, haloalkoxy, hydroxy, hydroxyalkyl, cyano, amino, nitro, cycloalkyl and heterocyclyl;
- $R^1$ is selected from the group consisting of hydrogen atom, halogen, alkyl, alkoxy, haloalkyl, haloalkoxy, hydroxy, hydroxyalkyl, cyano, amino, nitro, cycloalkyl, heterocyclyl, aryl and heteroaryl, wherein the alkyl, cycloalkyl, heterocyclyl, aryl and heteroaryl are each independently optionally substituted by one or more substituent(s) selected from the group consisting of halogen, alkyl, alkoxy, haloalkyl, haloalkoxy, hydroxy, hydroxyalkyl, cyano, amino, nitro, cycloalkyl, heterocyclyl, aryl and heteroaryl;
- $R^2$ and $R^3$ are identical or different, and are each independently selected from the group consisting of hydrogen atom, halogen, alkyl, alkoxy, haloalkyl, haloalkoxy, hydroxy, hydroxyalkyl, cyano, amino, nitro, cycloalkyl, heterocyclyl, aryl and heteroaryl;
- $R^4$ is selected from the group consisting of alkyl, haloalkyl, cycloalkyl, heterocyclyl, aryl and heteroaryl, wherein the alkyl, cycloalkyl, heterocyclyl, aryl and heteroaryl are each independently optionally substituted by one or more substituent(s) selected from the group consisting of alkyl, alkoxy, halogen, amino, cyano, nitro, hydroxy, hydroxyalkyl, cycloalkyl, heterocyclyl, aryl and heteroaryl; and
- $R^5$ is selected from the group consisting of hydrogen atom, halogen, alkyl, alkoxy, haloalkyl, haloalkoxy, hydroxy, hydroxyalkyl, cyano, amino, nitro, cycloalkyl, heterocyclyl, aryl and heteroaryl.

The compounds of formula (IB) according to the present invention typically include, but are not limited to:

| Example No. | Structure and name of the compound |
|---|---|
| 1g | 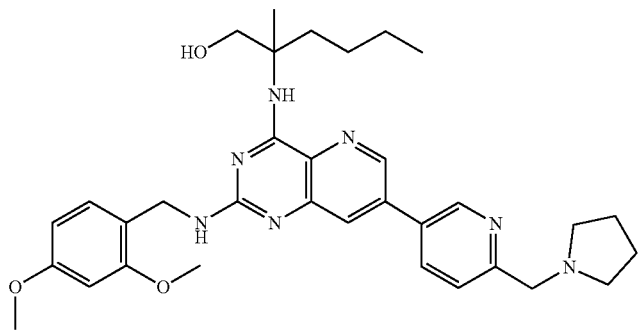<br>2-((2-((2,4-Dimethoxybenzyl)amino)-7-(6-(pyrrolidin-1-ylmethyl)pyridin-3-yl)pyrido[3,2-d]pyrimidin-4-yl)amino)-2-methylhexan-1-ol<br>1g |
| 2g | 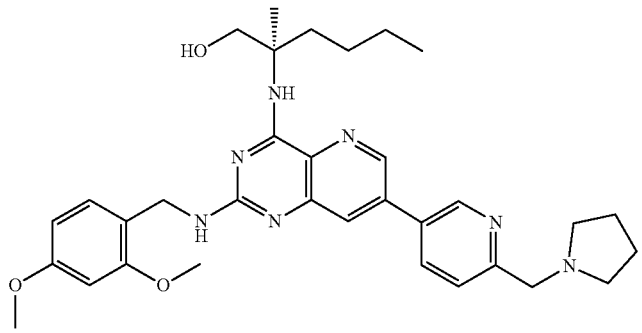<br>(R)-2-((2-((2,4-Dimethoxybenzyl)amino)-7-(6-(pyrrolidin-1-ylmethyl)pyridin-3-yl)pyrido[3,2-d]pyrimidin-4-yl)amino)-2-methylhexan-1-ol<br>2g |
| 3c | 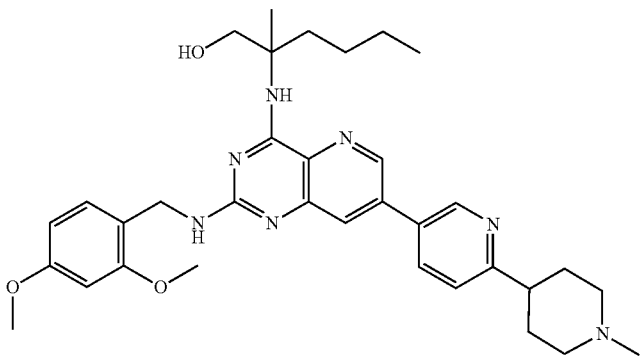<br>2-((2-((2,4-Dimethoxybenzyl)amino)-7-(6-(1-methylpiperidin-4-yl)pyridin-3-yl)pyrido[3,2-d]pyrimidin-4-yl)amino)-2-methylhexan-1-ol<br>3c |

-continued

| Example No. | Structure and name of the compound |
|---|---|
| 4c | 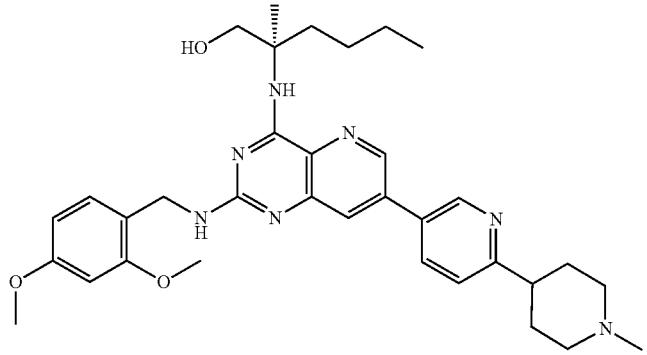<br>4c<br>(R)-2-((2-((2,4-Dimethoxybenzyl)amino)-7-(6-(1-methylpiperidin-4-yl)<br>pyridin-3-yl)pyrido[3,2-d]pyrimidin-4-yl)amino)-2-methylhexan-1-ol<br>4c |
| 5b | 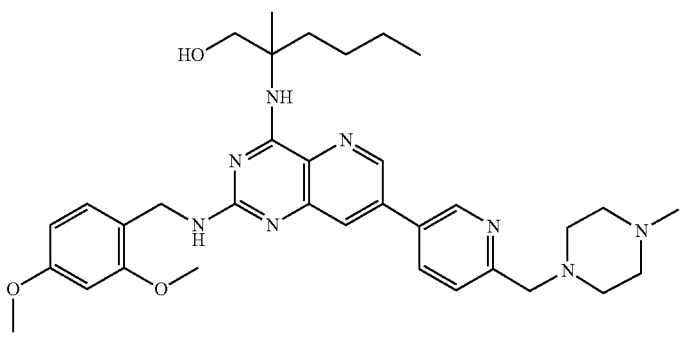<br>5b<br>2-((2-((2,4-Dimethoxybenzyl)amino)-7-(6-((4-methylpiperazin-1-yl)<br>methyl)pyridin-3-yl)pyrido[3,2-d]pyrimidin-4-yl)amino)-2-methylhexan-1-ol<br>5b |
| 6b | 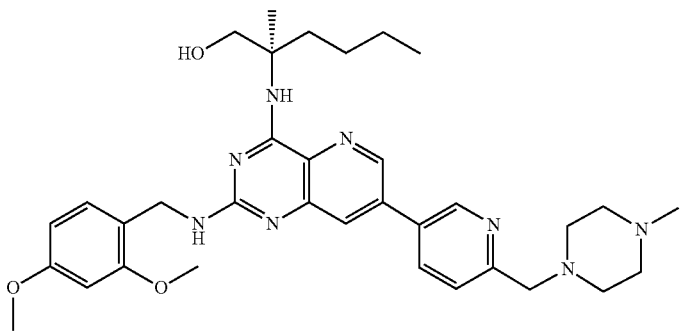<br>6b<br>(R)-2-((2-((2,4-Dimethoxybenzyl)amino)-7-(6-((4-methylpiperazin-1-yl)<br>methyl)pyridin-3-yl)pyrido[3,2-d]pyrimidin-4-yl)amino)-2-methylhexan-1-ol<br>6b |

| Example No. | Structure and name of the compound |
|---|---|
| 7d | 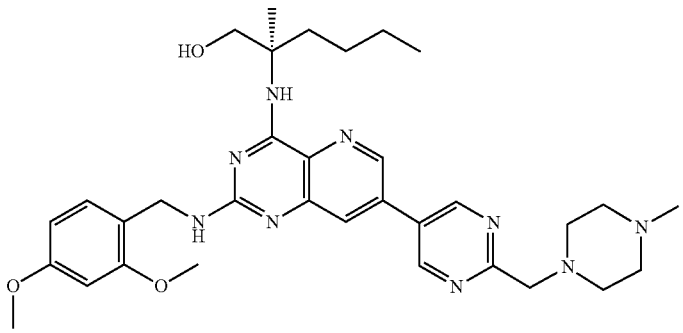<br>7d<br>(R)-2-((2-((2,4-Dimethoxybenzyl)amino)-7-(2-((4-methylpiperazin-1-yl)methyl)pyrimidin-5-yl)pyrido[3,2-d]pyrimidin-4-yl)amino)-2-methylhexan-1-ol<br>7d |
| 8e | 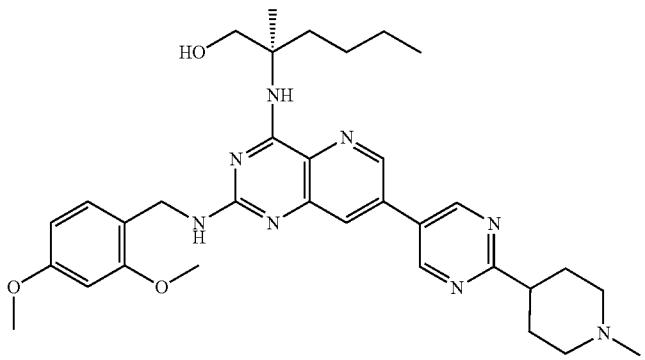<br>8e<br>(R)-2-((2-((2,4-Dimethoxybenzyl)amino)-7-(2-(1-methylpiperidin-4-yl)pyrimidin-5-yl)pyrido[3,2-d]pyrimidin-4-yl)amino)-2-methylhexan-1-ol<br>8e |
| 9d | 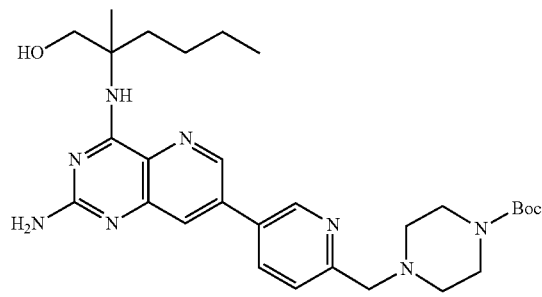<br>9d<br>Tert-butyl 4-((5-(2-Amino-4-((1-hydroxy-2-methylhexan-2-yl)amino)pyrido[3,2-d]pyrimidin-7-yl)pyridin-2-yl)methyl)piperazine-1-carboxylate<br>9d | or a tautomer, mesomer, racemate, enantiomer, diastereomer thereof, or mixture thereof, or a pharmaceutically acceptable salt thereof.

In another aspect, the present invention relates to a method for preparing the compound of formula (I) according to the present invention, comprising a step of:

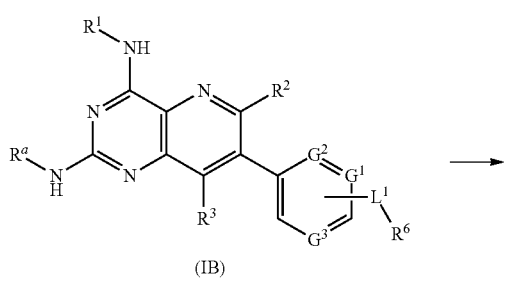

(IB)

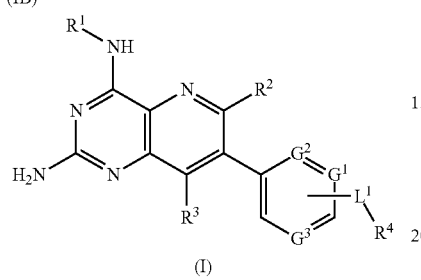

(I)

subjecting the compound of formula (IB) to a deprotection reaction to obtain the compound of formula (I);
wherein:
$R^a$ is an amino protecting group, and preferably 2,4-dimethoxybenzyl;
$G^1$, $G^2$ and $G^3$ are identical or different, and are each independently selected from the group consisting of CH, $CR^5$ and N;
$L^1$ is selected from the group consisting of alkylene and covalent bond, wherein the alkylene is optionally substituted by one or more substituent(s) selected from the group consisting of halogen, alkyl, alkoxy, haloalkyl, haloalkoxy, hydroxy, hydroxyalkyl, cyano, amino, nitro, cycloalkyl and heterocyclyl;
$R^1$ is selected from the group consisting of hydrogen atom, halogen, alkyl, alkoxy, haloalkyl, haloalkoxy, hydroxy, hydroxyalkyl, cyano, amino, nitro, cycloalkyl, heterocyclyl, aryl and heteroaryl, wherein the alkyl, cycloalkyl, heterocyclyl, aryl and heteroaryl are each independently optionally substituted by one or more substituent(s) selected from the group consisting of halogen, alkyl, alkoxy, haloalkyl, haloalkoxy, hydroxy, hydroxyalkyl, cyano, amino, nitro, cycloalkyl, heterocyclyl, aryl and heteroaryl;
$R^2$ and $R^3$ are identical or different, and are each independently selected from the group consisting of hydrogen atom, halogen, alkyl, alkoxy, haloalkyl, haloalkoxy, hydroxy, hydroxyalkyl, cyano, amino, nitro, cycloalkyl, heterocyclyl, aryl and heteroaryl;
$R^4$ is selected from the group consisting of alkyl, haloalkyl, cycloalkyl, heterocyclyl, aryl and heteroaryl, wherein the alkyl, cycloalkyl, heterocyclyl, aryl and heteroaryl are each independently optionally substituted by one or more substituent(s) selected from the group consisting of alkyl, alkoxy, halogen, amino, cyano, nitro, hydroxy, hydroxyalkyl, cycloalkyl, heterocyclyl, aryl and heteroaryl;
$R^6$ is selected from the group consisting of alkyl, haloalkyl, cycloalkyl, heterocyclyl, aryl and heteroaryl, wherein the alkyl, cycloalkyl, heterocyclyl, aryl and heteroaryl are each independently optionally substituted by one or more substituent(s) selected from the group consisting of alkyl, alkoxy, halogen, amino, cyano, nitro, hydroxy, hydroxyalkyl, tert-butoxycarbonyl, cycloalkyl, heterocyclyl, aryl and heteroaryl; and
$R^5$ is selected from the group consisting of hydrogen atom, halogen, alkyl, alkoxy, haloalkyl, haloalkoxy, hydroxy, hydroxyalkyl, cyano, amino, nitro, cycloalkyl, heterocyclyl, aryl and heteroaryl.

In another aspect, the present invention relates to a method for preparing the compound of formula (I) according to the present invention, comprising a step of:

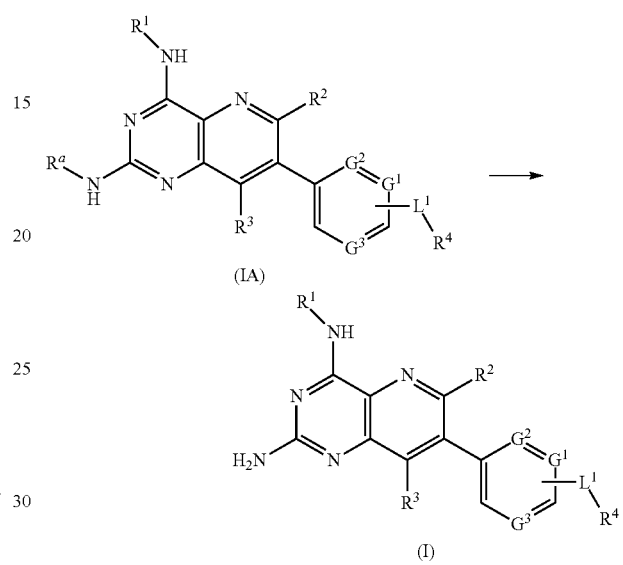

subjecting the compound of formula (IA) to a deprotection reaction to obtain the compound of formula (I);
wherein:
$R^a$ is an amino protecting group, and preferably 2,4-dimethoxy benzyl; and
$G^1$ to $G^3$, $L^1$ and $R^1$ to $R^4$ are as defined in formula (I).

In another aspect, the present invention relates to a method for preparing the compound of formula (Ia) according to the present invention, comprising a step of:

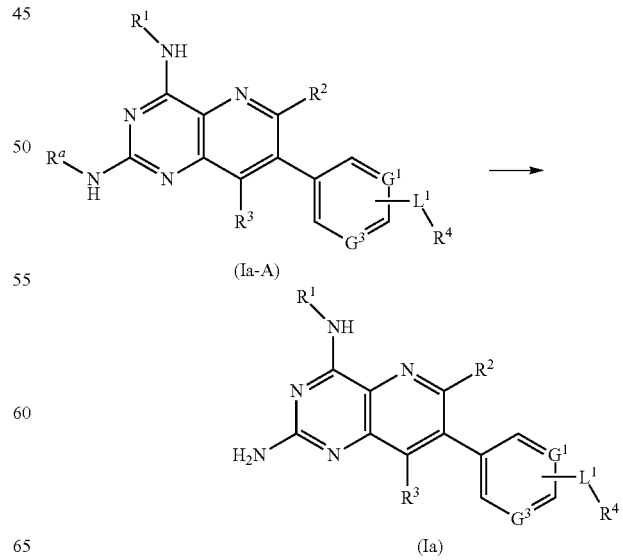

subjecting a compound of formula (Ia-A) to a deprotection reaction to obtain the compound of formula (Ia);
wherein:
$R^a$ is an amino protecting group, and preferably 2,4-dimethoxybenzyl; and
$G^1$, $G^3$, $L^1$ and $R^1$ to $R^4$ are as defined in formula (Ia).

In another aspect, the present invention relates to a method for preparing the compound of formula (Ib) according to the present invention, comprising a step of:

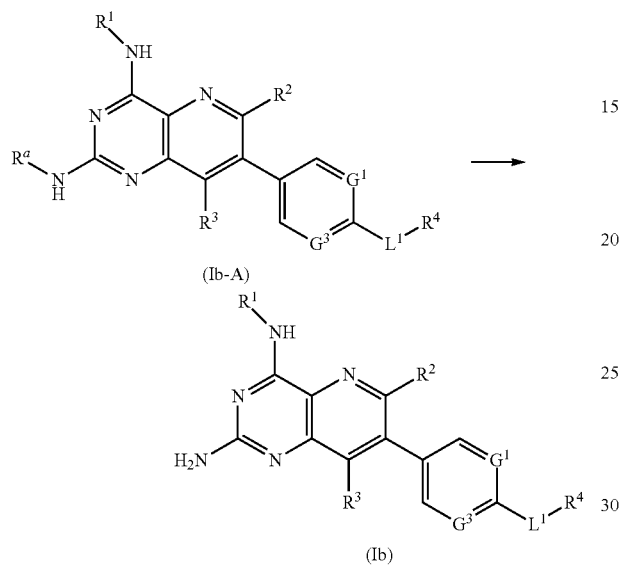

(Ib-A)

(Ib)

subjecting a compound of formula (Ib-A) to a deprotection reaction to obtain the compound of formula (Ib);
wherein:
$R^a$ is an amino protecting group, and preferably 2,4-dimethoxybenzyl; and
$G^1$, $G^3$, $L^1$ and $R^1$ to $R^4$ are as defined in formula (Ib).

In another aspect, the present invention relates to a method for preparing the compound of formula (II) according to the present invention, comprising a step of:

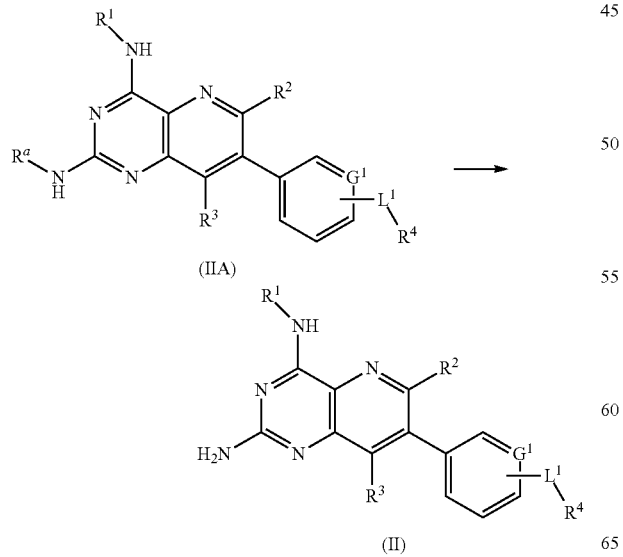

(IIA)

(II)

subjecting a compound of formula (IIA) to a deprotection reaction to obtain the compound of formula (II);
wherein:
$R^a$ is an amino protecting group, and preferably 2,4-dimethoxybenzyl; and
$G^1$, $L^1$ and $R^1$ to $R^4$ are as defined in formula (II).

In another aspect, the present invention relates to a method for preparing the compound of formula (III) according to the present invention, comprising a step of:

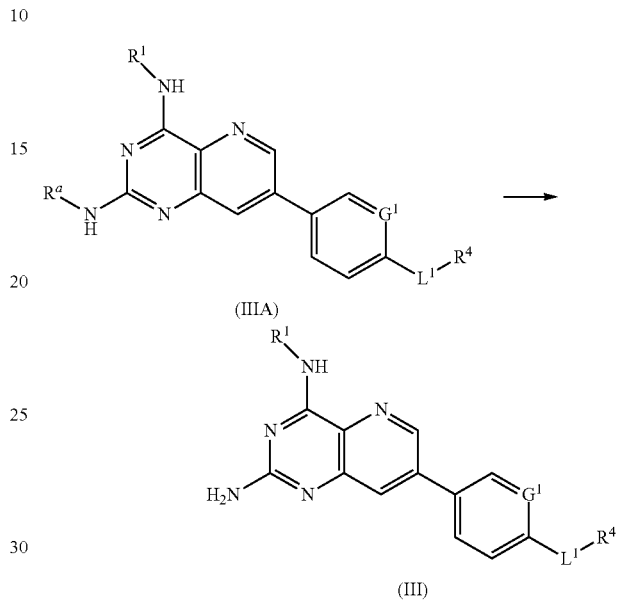

(IIIA)

(III)

subjecting a compound of formula (IIIA) to a deprotection reaction to obtain the compound of formula (III);
wherein:
$R^a$ is an amino protecting group, and preferably 2,4-dimethoxybenzyl; and
$G^1$, $L^1$, $R^1$ and $R^4$ are as defined in formula (III).

In another aspect, the present invention relates to a method for preparing the compound of formula (IV) according to the present invention, comprising a step of:

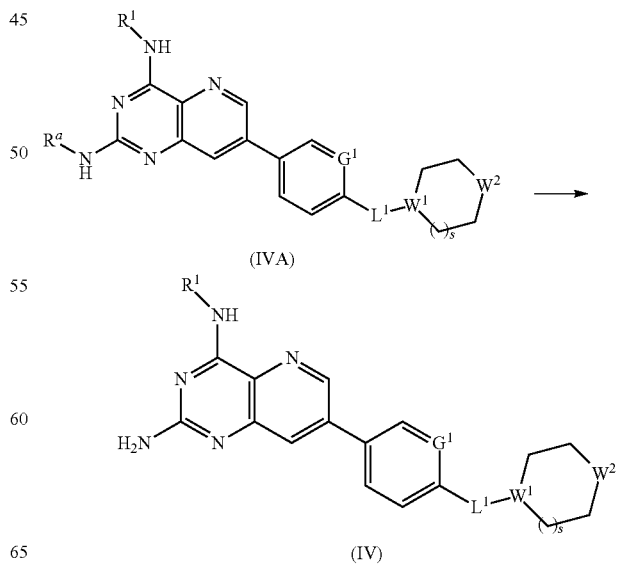

(IVA)

(IV)

subjecting a compound of formula (IVA) to a deprotection reaction to obtain the compound of formula (IV);

wherein:

$R^a$ is an amino protecting group, and preferably 2,4-dimethoxybenzyl; and $G^1$, $L^1$, $R^1$, $W^1$, $W^2$ and s are as defined in formula (IV).

In another aspect, the present invention relates to a method for preparing the compound of formula (Va) according to the present invention, comprising a step of:

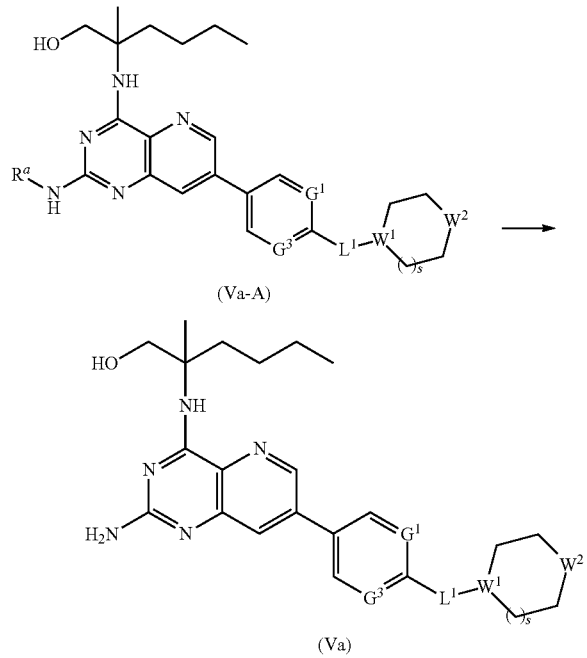

(Va-A)

(Va)

subjecting a compound of formula (Va-A) to a deprotection reaction to obtain the compound of formula (Va);

wherein:

$R^a$ is an amino protecting group, and preferably 2,4-dimethoxybenzyl; and $G^1$, $G^3$, $L^1$, $W^1$, $W^2$ and s are as defined in formula (Va).

In another aspect, the present invention relates to a method for preparing the compound of formula (V) according to the present invention, comprising a step of:

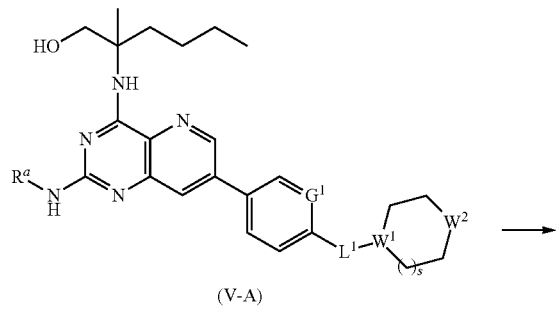

(V-A)

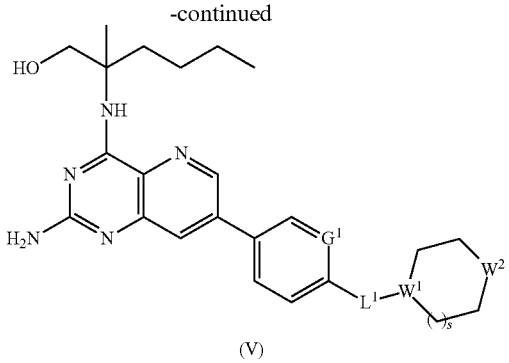

(V)

subjecting a compound of formula (V-A) to a deprotection reaction to obtain the compound of formula (V);

wherein:

$R^a$ is an amino protecting group, and preferably 2,4-dimethoxy benzyl; and $G^1$, $L^1$, $W^1$, $W^2$ and s are as defined in formula (V).

The present invention further provides a pharmaceutical composition comprising a therapeutically effective amount of the compound of formula (I), or a tautomer, mesomer, racemate, enantiomer, diastereomer thereof, or mixture thereof, or a pharmaceutically acceptable salt thereof according to the present invention, and one or more pharmaceutically acceptable carrier(s), diluent(s) or excipient(s).

The present invention further relates to a use of the compound of formula (I), or a tautomer, mesomer, racemate, enantiomer, diastereomer thereof, or mixture thereof, or a pharmaceutically acceptable salt thereof according to the present invention, or the pharmaceutical composition comprising the same in the preparation of a medicament for activating TLR8.

The present invention further relates to a use of the compound of formula (I), or a tautomer, mesomer, racemate, enantiomer, diastereomer thereof, or mixture thereof, or a pharmaceutically acceptable salt thereof according to the present invention, or the pharmaceutical composition comprising the same in the preparation of a medicament for the treatment of infection caused by virus, wherein the virus is preferably hepatitis B virus, hepatitis C virus, influenza virus, herpes virus and AIDS virus.

The present invention further relates to a use of the compound of formula (I), or a tautomer, mesomer, racemate, enantiomer, diastereomer thereof, or mixture thereof, or a pharmaceutically acceptable salt thereof according to the present invention, or the pharmaceutical composition comprising the same in the preparation of a medicament for regulating immune system.

The present invention further relates to a use of the compound of formula (I), or a tautomer, mesomer, racemate, enantiomer, diastereomer thereof, or mixture thereof, or a pharmaceutically acceptable salt thereof according to the present invention, or the pharmaceutical composition comprising the same in the preparation of a medicament for the treatment or prevention of tumor.

The present invention further relates to a method for activating TLR8, comprising a step of contacting the compound of formula (I), or a tautomer, mesomer, racemate, enantiomer, diastereomer thereof, or mixture thereof, or a pharmaceutically acceptable salt thereof according to the present invention, or the pharmaceutical composition comprising the same with TLR8.

The present invention further relates to a method for treating infection caused by virus, comprising a step of administration of a therapeutically effective dose of the compound of formula (I), or a tautomer, mesomer, racemate, enantiomer, diastereomer thereof, or mixture thereof, or a pharmaceutically acceptable salt thereof according to the present invention, or the pharmaceutical composition comprising the same to a patient in need thereof, wherein the virus is preferably hepatitis B virus, hepatitis C virus, influenza virus, herpes virus and AIDS virus.

The present invention further relates to a method for treating or preventing a tumor, comprising a step of administration of a therapeutically or preventively effective dose of the compound of formula (I), or a tautomer, mesomer, racemate, enantiomer, diastereomer thereof, or mixture thereof, or a pharmaceutically acceptable salt thereof according to the present invention, or the pharmaceutical composition comprising the same to a patient in need thereof.

The present invention further relates to the compound of formula (I), or a tautomer, mesomer, racemate, enantiomer, diastereomer thereof, or mixture thereof, or a pharmaceutically acceptable salt thereof according to the present invention, or the pharmaceutical composition comprising the same, for use as a medicament.

The present invention further relates to the compound of formula (I), or a tautomer, mesomer, racemate, enantiomer, diastereomer thereof, or mixture thereof, or a pharmaceutically acceptable salt thereof according to the present invention, or the pharmaceutical composition comprising the same according to the present invention, for use as a TLR8 agonist.

The present invention further relates to the compound of formula (I), or a tautomer, mesomer, racemate, enantiomer, diastereomer thereof, or mixture thereof, or a pharmaceutically acceptable salt thereof according to the present invention, or the pharmaceutical composition comprising the same, for use as a medicament for the treatment of infection caused by virus, wherein the virus is preferably hepatitis B virus, hepatitis C virus, influenza virus, herpes virus and AIDS virus.

The present invention further relates to the compound of formula (I), or a tautomer, mesomer, racemate, enantiomer, diastereomer thereof, or mixture thereof, or a pharmaceutically acceptable salt thereof according to the present invention, or the pharmaceutical composition comprising the same, for use as a medicament for regulating immune system.

The present invention further relates to the compound of formula (I), or a tautomer, mesomer, racemate, enantiomer, diastereomer thereof, or mixture thereof, or a pharmaceutically acceptable salt thereof according to the present invention, or the pharmaceutical composition comprising the same, for use as a medicament for treating or preventing a tumor.

The tumor of the present invention is preferably a cancer, and more preferably selected from the group consisting of melanoma, lung cancer, liver cancer, basal cell carcinoma, kidney cancer, myeloma, biliary tract cancer, brain cancer, breast cancer, cervical cancer, choriocarcinoma, colon cancer, rectal cancer, head and neck cancer, peritoneal tumor, fallopian tube cancer, endometrial cancer, esophageal cancer, stomach cancer, leukemia, lymphoma, sarcoma, neuroblastoma, oral cancer, ovarian cancer, pancreatic cancer, prostate cancer, testicular cancer, skin cancer and thyroid cancer.

The dose of the compound or composition used in the treatment method of the present invention will generally vary according to the severity of the disease, the weight of the patient and the relative efficacy of the compound. However, as a general guide, a suitable unit dose can be 0.1 to 1000 mg.

In addition to the active compound, the pharmaceutical composition of the present invention can also comprise one or more auxiliary material(s) including filler (diluent), binder, wetting agent, disintegrant, excipient and the like. Depending on the administration mode, the composition can comprise 0.1 to 99% by weight of the active compound.

The pharmaceutical composition containing the active ingredient can be in a form suitable for oral administration, for example, a tablet, troche, lozenge, aqueous or oily suspension, dispersible powder or granule, emulsion, hard or soft capsule, syrup or elixir. An oral composition can be prepared according to any known method in the art for the preparation of pharmaceutical composition. Such a composition can contain one or more ingredients selected from the group consisting of sweeteners, flavoring agents, colorants and preservatives, in order to provide a pleasing and palatable pharmaceutical formulation. The tablet contains the active ingredient in admixture with nontoxic, pharmaceutically acceptable excipients suitable for the manufacture of tablets. These excipients can be inert excipients, granulating agents, disintegrating agents, binders and lubricants. The tablet can be uncoated or coated by means of a known technique to mask drug taste or delay the disintegration and absorption of the active ingredient in the gastrointestinal tract, thereby providing sustained release over a long period of time.

An oral formulation can also be provided as soft gelatin capsules in which the active ingredient is mixed with an inert solid diluent, or the active ingredient is mixed with a water-soluble carrier or an oil medium.

An aqueous suspension contains the active ingredient in admixture with excipients suitable for the manufacture of an aqueous suspension. Such excipients are suspending agents, dispersants or wetting agents. The aqueous suspension can also contain one or more preservative(s), one or more colorant(s), one or more flavoring agent(s), and one or more sweetener(s).

An oil suspension can be formulated by suspending the active ingredient in a vegetable oil or mineral oil. The oil suspension can contain a thickener. The aforementioned sweeteners and flavoring agents can be added to provide a palatable formulation. These compositions can be preserved by adding an antioxidant.

The pharmaceutical composition of the present invention can also be in the form of an oil-in-water emulsion. The oil phase can be a vegetable oil, or a mineral oil, or a mixture thereof. Suitable emulsifying agents can be naturally occurring phospholipids. The emulsion can also contain a sweetening agent, flavoring agent, preservative and antioxidant. Such a formulation can also contain a demulcent, preservative, colorant and antioxidant.

The pharmaceutical composition of the present invention can be in the form of a sterile injectable aqueous solution. Acceptable vehicles or solvents that can be used are water, Ringer's solution or isotonic sodium chloride solution. The sterile injectable formulation can be a sterile injectable oil-in-water micro-emulsion in which the active ingredient is dissolved in the oil phase. The injectable solution or micro-emulsion can be introduced into a patient's bloodstream by local bolus injection. Alternatively, the solution and micro-emulsion are preferably administrated in a manner that maintains a constant circulating concentration of the compound of the present invention. In order to maintain this constant concentration, a continuous intravenous delivery device can be used. An example of such a device is Deltec CADD-PLUS™. 5400 intravenous injection pump.

The pharmaceutical composition can be in the form of a sterile injectable aqueous or oily suspension for intramuscular and subcutaneous administration. Such a suspension can be formulated with suitable dispersants or wetting agents and suspending agents as described above according to known techniques. The sterile injectable formulation can also be a sterile injectable solution or suspension prepared in a nontoxic parenterally acceptable diluent or solvent. Moreover, sterile fixed oils can easily be used as a solvent or suspending medium.

The compound of the present invention can be administrated in the form of a suppository for rectal administration. These pharmaceutical compositions can be prepared by mixing the drug with a suitable non-irritating excipient that is solid at ordinary temperatures, but liquid in the rectum, thereby melting in the rectum to release the drug. Such materials include cocoa butter, glycerin gelatin, hydrogenated vegetable oil, a mixture of polyethylene glycols of various molecular weights and fatty acid esters thereof.

It is well known to those skilled in the art that the dosage of a drug depends on a variety of factors including, but not limited to the following factors: activity of a specific compound, age of the patient, weight of the patient, general health of the patient, behavior of the patient, diet of the patient, administration time, administration route, excretion rate, drug combination and the like. In addition, the optimal treatment, such as treatment mode, daily dose of the compound of formula (I) or the type of pharmaceutically acceptable salt thereof can be verified by traditional therapeutic regimens.

DETAILED DESCRIPTION OF THE INVENTION

Unless otherwise stated, the terms used in the specification and claims have the meanings described below.

The term "alkyl" refers to a saturated aliphatic hydrocarbon group, which is a straight or branched chain group comprising 1 to 20 carbon atoms, preferably an alkyl having 1 to 12 carbon atoms, and more preferably an alkyl having 1 to 6 carbon atoms. Non-limiting examples include methyl, ethyl, n-propyl, isopropyl, n-butyl, isobutyl, tert-butyl, sec-butyl, n-pentyl, 1,1-dimethylpropyl, 1,2-dimethylpropyl, 2,2-dimethylpropyl, 1-ethylpropyl, 2-methylbutyl, 3-methylbutyl, n-hexyl, 1-ethyl-2-methylpropyl, 1,1,2-trimethylpropyl, 1,1-dimethylbutyl, 1,2-dimethylbutyl, 2,2-dimethylbutyl, 1,3-dimethylbutyl, 2-ethylbutyl, 2-methylpentyl, 3-methylpentyl, 4-methylpentyl, 2,3-dimethylbutyl, n-heptyl, 2-methylhexyl, 3-methylhexyl, 4-methylhexyl, 5-methylhexyl, 2,3-dimethylpentyl, 2,4-dimethylpentyl, 2,2-dimethylpentyl, 3,3-dimethylpentyl, 2-ethylpentyl, 3-ethylpentyl, n-octyl, 2,3-dimethylhexyl, 2,4-dimethylhexyl, 2,5-dimethylhexyl, 2,2-dimethylhexyl, 3,3-dimethylhexyl, 4,4-dimethylhexyl, 2-ethylhexyl, 3-ethylhexyl, 4-ethylhexyl, 2-methyl-2-ethylpentyl, 2-methyl-3-ethylpentyl, n-nonyl, 2-methyl-2-ethylhexyl, 2-methyl-3-ethylhexyl, 2,2-diethylpentyl, n-decyl, 3,3-diethylhexyl, 2,2-diethylhexyl, and various branched isomers thereof. More preferably, the alkyl group is a lower alkyl having 1 to 6 carbon atoms, and non-limiting examples include methyl, ethyl, n-propyl, isopropyl, n-butyl, isobutyl, tert-butyl, sec-butyl, n-pentyl, 1,1-dimethylpropyl, 1,2-dimethylpropyl, 2,2-dimethylpropyl, 1-ethylpropyl, 2-methylbutyl, 3-methylbutyl, n-hexyl, 1-ethyl-2-methylpropyl, 1,1,2-trimethylpropyl, 1,1-dimethylbutyl, 1,2-dimethylbutyl, 2,2-dimethylbutyl, 1,3-dimethylbutyl, 2-ethylbutyl, 2-methylpentyl, 3-methylpentyl, 4-methylpentyl, 2,3-dimethylbutyl and the like. The alkyl group can be substituted or unsubstituted. When substituted, the substituent group can be substituted at any available connection point. The substituent group is one or more group(s) independently optionally selected from the group consisting of halogen, alkyl, haloalkyl, alkoxy, haloalkoxy, alkylthio, alkylamino, alkenyl, alkynyl, thiol, hydroxy, hydroxyalkyl, cyano, amino, nitro, cycloalkyl, heterocyclyl, aryl, heteroaryl, cycloalkoxy, heterocycloalkoxy, cycloalkylthio, heterocyclylthio and oxo.

The term "alkoxy" refers to an —O-(alkyl) or an —O-(unsubstituted cycloalkyl) group, wherein the alkyl and cycloalkyl are as defined above. Non-limiting examples of alkoxy include methoxy, ethoxy, propoxy, butoxy, cyclopropyloxy, cyclobutyloxy, cyclopentyloxy, cyclohexyloxy. The alkoxy can be optionally substituted or unsubstituted. When substituted, the substituent group can be substituted at any available connection point. The substituent group is one or more group(s) independently optionally selected from the group consisting of halogen, alkyl, haloalkyl, alkoxy, haloalkoxy, alkylthio, alkylamino, alkenyl, alkynyl, thiol, hydroxy, hydroxyalkyl, cyano, amino, nitro, cycloalkyl, heterocyclyl, aryl, heteroaryl, cycloalkoxy, heterocycloalkoxy, cycloalkylthio, heterocyclylthio and oxo.

The term "cycloalkyl" refers to a saturated or partially unsaturated monocyclic or polycyclic hydrocarbon substituent group having 3 to 20 carbon atoms, preferably 3 to 12 carbon atoms, more preferably 3 to 6 carbon atoms (for example 3, 4, 5 or 6 carbon atoms), and most preferably 5 to 6 carbon atoms. Non-limiting examples of monocyclic cycloalkyl include cyclopropyl, cyclobutyl, cyclopentyl, cyclopentenyl, cyclohexyl, cyclohexenyl, cyclohexadienyl, cycloheptyl, cycloheptatrienyl, cyclooctyl and the like. Polycyclic cycloalkyl includes a cycloalkyl having a spiro ring, fused ring or bridged ring.

The term "spiro cycloalkyl" refers to a 5 to 20 membered polycyclic group with individual rings connected through one shared carbon atom (called a spiro atom), wherein the rings can contain one or more double bond(s), but none of the rings has a completely conjugated t-electron system. The spiro cycloalkyl is preferably a 6 to 14 membered spiro cycloalkyl, and more preferably 7 to 10 membered spiro cycloalkyl (for example 7, 8, 9 or 10 membered spiro cycloalkyl). According to the number of the spiro atoms shared between the rings, the spiro cycloalkyl can be divided into mono-spiro cycloalkyl, di-spiro cycloalkyl, or poly-spiro cycloalkyl, and the spiro cycloalkyl is preferably a mono-spiro cycloalkyl or di-spiro cycloalkyl, and more preferably 4-membered/4-membered, 4-membered/5-membered, 4-membered/6-membered, 5-membered/5-membered, or 5-membered/6-membered mono-spiro cycloalkyl. Non-limiting examples of spiro cycloalkyl include:

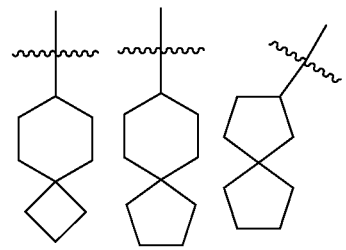

-continued

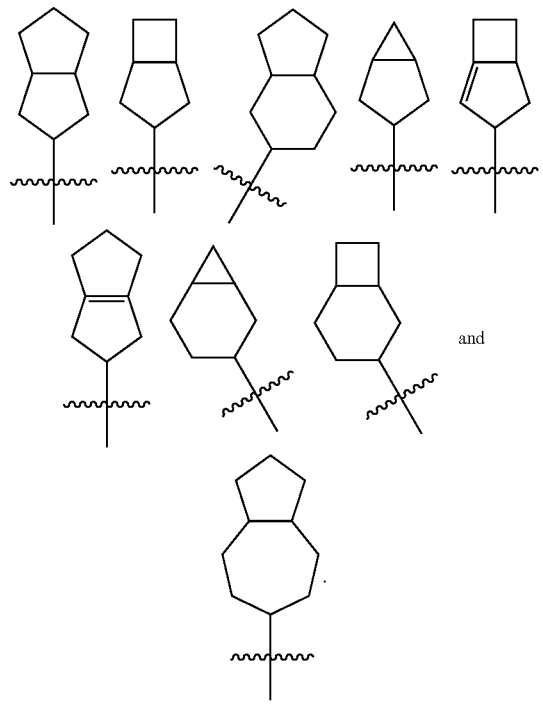

and

The term "fused cycloalkyl" refers to a 5 to 20 membered all-carbon polycyclic group, wherein each ring in the system shares an adjacent pair of carbon atoms with another ring, wherein one or more ring(s) can contain one or more double bonds, but none of the rings has a completely conjugated n-electron system. The fused cycloalkyl is preferably a 6 to 14 membered fused cycloalkyl, and more preferably 7 to 10 membered fused cycloalkyl (for example 7, 8, 9 or 10 membered fused cycloalkyl). According to the number of membered rings, the fused cycloalkyl can be divided into bicyclic, tricyclic, tetracyclic or polycyclic fused cycloalkyl, and the fused cycloalkyl is preferably a bicyclic or tricyclic fused cycloalkyl, and more preferably 5-membered/5-membered, or 5-membered/6-membered bicyclic fused cycloalkyl. Non-limiting examples of fused cycloalkyl include:

The term "bridged cycloalkyl" refers to a 5 to 20 membered all-carbon polycyclic group, wherein every two rings in the system share two disconnected carbon atoms, wherein the rings can have one or more double bond(s), but none of the rings has a completely conjugated π-electron system. The bridged cycloalkyl is preferably a 6 to 14 membered bridged cycloalkyl, and more preferably 7 to 10 membered bridged cycloalkyl (for example 7, 8, 9 or 10 membered fused cycloalkyl). According to the number of membered rings, the bridged cycloalkyl can be divided into bicyclic, tricyclic, tetracyclic or polycyclic bridged cycloalkyl, and the bridged cycloalkyl is preferably a bicyclic, tricyclic or tetracyclic bridged cycloalkyl, and more preferably bicyclic or tricyclic bridged cycloalkyl. Non-limiting examples of bridged cycloalkyl include:

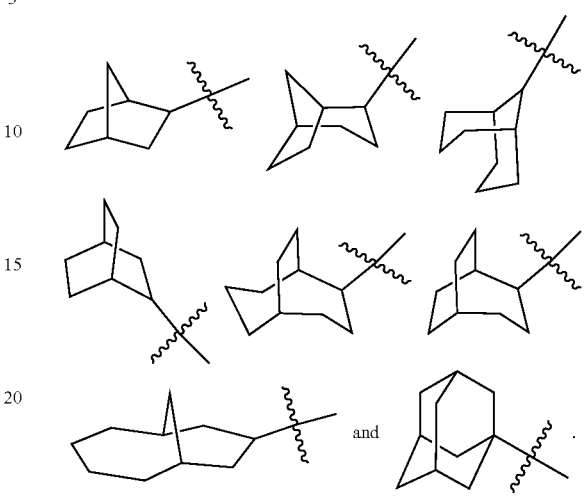

and

The cycloalkyl ring can be fused to the ring of aryl, heteroaryl or heterocyclyl, wherein the ring bound to the parent structure is cycloalkyl. Non-limiting examples include indanyl, tetrahydronaphthyl, benzocycloheptyl and the like, and preferably benzocyclopentyl, tetrahydronaphthyl. The cycloalkyl can be optionally substituted or unsubstituted. When substituted, the substituent group can be substituted at any available connection point. The substituent group is one or more group(s) independently optionally selected from the group consisting of halogen, alkyl, haloalkyl, alkoxy; haloalkoxy, alkylthio, alkylamino, alkenyl, alkynyl, thiol, hydroxy, hydroxyalkyl, cyano, amino, nitro, cycloalkyl, heterocyclyl, aryl, heteroaryl, cycloalkoxy, heterocycloalkoxy, cycloalkylthio, heterocyclylthio and oxo.

The term "heterocyclyl" refers to a 3 to 20 membered saturated or partially unsaturated monocyclic or polycyclic hydrocarbon group, wherein one or more ring atom(s) are heteroatoms selected from the group consisting of N, O and $S(O)_m$ (wherein m is an integer of 0 to 2), but excluding —O—O—, —O—S— or —S—S— in the ring, with the remaining ring atoms being carbon atoms. Preferably, the heterocyclyl has 3 to 12 ring atoms wherein 1 to 4 atom(s) are heteroatoms; more preferably, 3 to 8 ring atoms wherein 1 to 3 atom(s) are heteroatoms; and most preferably 5 to 6 ring atoms wherein 1 to 2 or 1 to 3 atom(s) are heteroatoms. Non-limiting examples of monocyclic heterocyclyl include pyrrolidinyl, imidazolidinyl, tetrahydrofuranyl, tetrahydropyranyl, tetrahydrothienyl, dihydroimidazolyl, dihydrofuranyl, dihydropyrazolyl, dihydropyrrolyl, piperidinyl, piperazinyl, morpholinyl, thiomorpholinyl, homopiperazinyl and the like, and preferably tetrahydropyranyl, piperidinyl, pyrrolidinyl. Polycyclic heterocyclyl includes a heterocyclyl having a spiro ring, fused ring or bridged ring.

The term "spiro heterocyclyl" refers to a 5 to 20 membered polycyclic heterocyclyl group with individual rings connected through one shared atom (called a spiro atom), wherein one or more ring atom(s) are heteroatoms selected from the group consisting of N, O and $S(O)_m$ (wherein m is an integer of 0 to 2), with the remaining ring atoms being carbon atoms. The spiro heterocyclyl can contain one or more double bond(s), but none of the rings has a completely conjugated T-electron system. The spiro heterocyclyl is preferably a 6 to 14 membered spiro heterocyclyl, and more preferably 7 to 10 membered spiro heterocyclyl. According to the number of the spiro atoms shared between the rings, the spiro heterocyclyl can be divided into mono-spiro heterocyclyl, di-spiro heterocyclyl, or poly-spiro heterocyclyl, and the spiro heterocyclyl is preferably a mono-spiro heterocyclyl or di-spiro heterocyclyl, more preferably 4-membered/4-membered, 4-membered/5-membered, 4-membered/6-membered, 5-membered/5-membered, or 5-membered/6-membered mono-spiro heterocyclyl. Non-limiting examples of spiro heterocyclyl include:

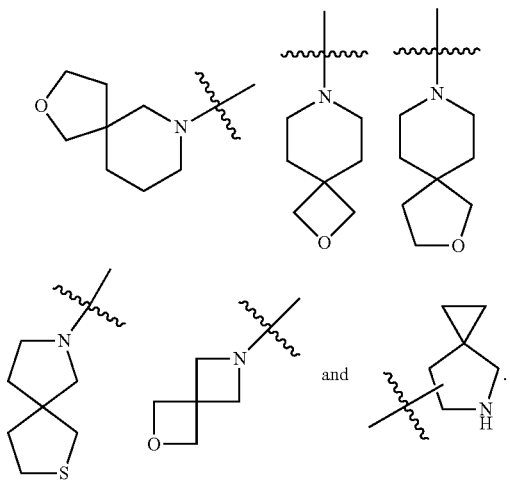

The term "fused heterocyclyl" refers to a 5 to 20 membered polycyclic heterocyclyl group, wherein each ring in the system shares an adjacent pair of atoms with another ring, one or more ring(s) can contain one or more double bond(s), but none of the rings has a completely conjugated π-electron system, and one or more ring atom(s) are heteroatoms selected from the group consisting of N, O and $S(O)_m$ (wherein m is an integer of 0 to 2), with the remaining ring atoms being carbon atoms. The fused heterocyclyl is preferably a 6 to 14 membered fused heterocyclyl, and more preferably 7 to 10 membered fused heterocyclyl (for example a 7, 8, 9 or 10 membered fused heterocyclyl). According to the number of membered rings, the fused heterocyclyl can be divided into bicyclic, tricyclic, tetracyclic or polycyclic fused heterocyclyl, and the fused heterocyclyl is preferably a bicyclic or tricyclic fused heterocyclyl, and more preferably 5-membered/5-membered or 5-membered/6-membered bicyclic fused heterocyclyl. Non-limiting examples of fused heterocyclyl include:

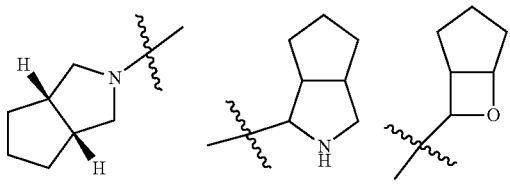

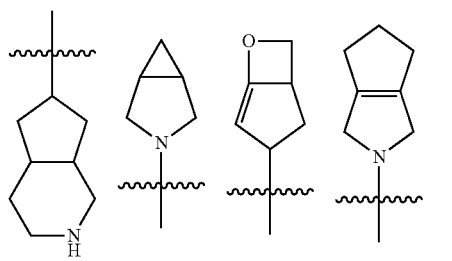

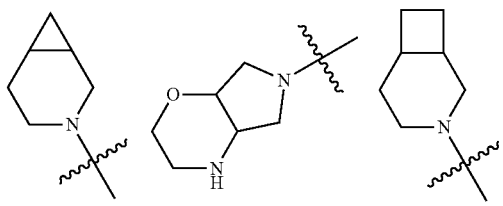

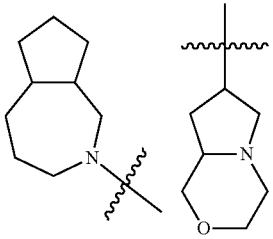

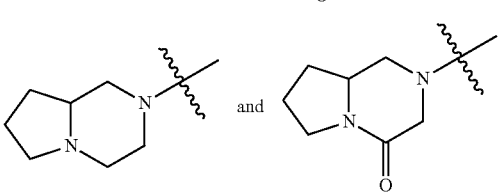

The term "bridged heterocyclyl" refers to a 5 to 14 membered polycyclic heterocyclyl group, wherein every two rings in the system share two disconnected atoms, wherein the rings can have one or more double bond(s), but none of the rings has a completely conjugated π-electron system, and one or more ring atom(s) are heteroatoms selected from the group consisting of N, O and $S(O)_m$ (wherein m is an integer of 0 to 2), with the remaining ring atoms being carbon atoms. The bridged heterocyclyl is preferably a 6 to 14 membered bridged heterocyclyl, and more preferably 7 to 10 membered bridged heterocyclyl (for example a 7, 8, 9 or 10 membered bridged heterocyclyl). According to the number of membered rings, the bridged heterocyclyl can be divided into bicyclic, tricyclic, tetracyclic or polycyclic bridged heterocyclyl, and the bridged heterocyclyl is preferably a bicyclic, tricyclic or tetracyclic bridged heterocyclyl, and more preferably bicyclic or tricyclic bridged heterocyclyl. Non-limiting examples of bridged heterocyclyl include:

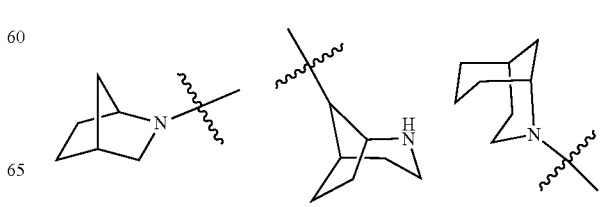

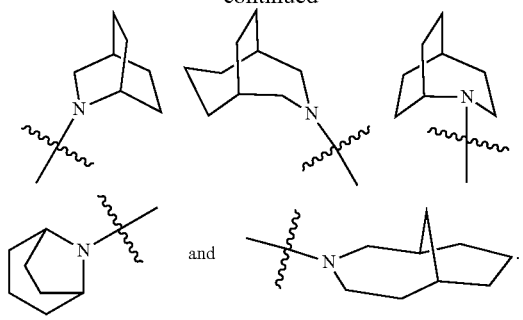

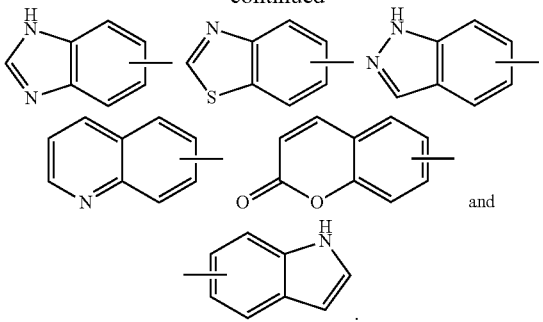

The heterocyclyl ring can be fused to the ring of aryl, heteroaryl or cycloalkyl, wherein the ring bound to the parent structure is heterocyclyl. Non-limiting examples thereof include:

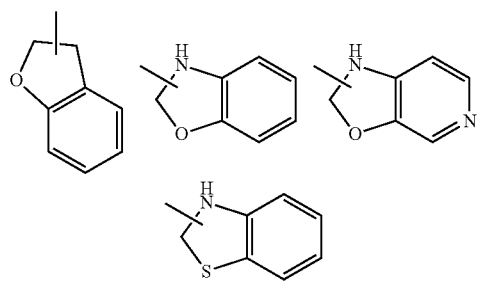

and the like.

The heterocyclyl can be optionally substituted or unsubstituted. When substituted, the substituent group can be substituted at any available connection point. The substituent group is one or more group(s) independently optionally selected from the group consisting of halogen, alkyl, haloalkyl, alkoxy, haloalkoxy, alkylthio, alkylamino, alkenyl, alkynyl, thiol, hydroxy, hydroxyalkyl, cyano, amino, nitro, cycloalkyl, heterocyclyl, aryl, heteroaryl, cycloalkoxy, heterocycloalkoxy, cycloalkylthio, heterocyclylthio and oxo.

The term "aryl" refers to a 6 to 14 membered all-carbon monocyclic ring or polycyclic fused ring (i.e. each ring in the system shares an adjacent pair of carbon atoms with another ring in the system) having a conjugated π-electron system, preferably a 6 to 10 membered aryl, and more preferably 5 to 6 membered aryl, for example, phenyl and naphthyl. The aryl ring can be fused to the ring of heteroaryl, heterocyclyl or cycloalkyl, wherein the ring bound to the parent structure is aryl ring. Non-limiting examples thereof include:

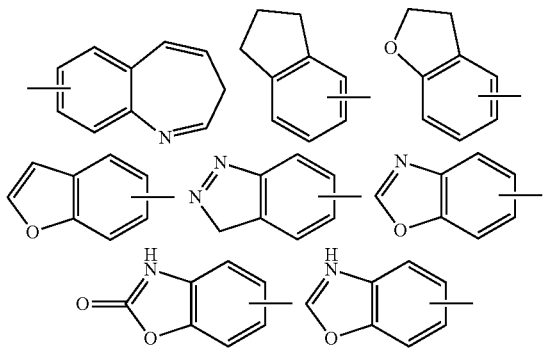

The aryl can be optionally substituted or unsubstituted. When substituted, the substituent group can be substituted at any available connection point. The substituent group is one or more group(s) independently optionally selected from the group consisting of halogen, alkyl, haloalkyl, alkoxy, haloalkoxy, alkylthio, alkylamino, alkenyl, alkynyl, thiol, hydroxy, hydroxyalkyl, cyano, amino, nitro, cycloalkyl, heterocyclyl, aryl, heteroaryl, cycloalkoxy, heterocycloalkoxy, cycloalkylthio, heterocyclylthio and oxo.

The term "heteroaryl" refers to a 5 to 14 membered heteroaromatic system having 1 to 4 heteroatoms selected from the group consisting of O, S and N. The heteroaryl is preferably a 5 to 10 membered heteroaryl having 1 to 3 heteroatoms, more preferably 5 or 6 membered heteroaryl having 1 to 2 heteroatoms: preferably for example, imidazolyl, furyl, thienyl, thiazolyl, pyrazolyl, oxazolyl, pyrrolyl, 1H-1,2,3-triazolyl, 4H-1,2,4-triazolyl, 4H-1,2,3-triazolyl, 1H-tetrazolyl, 2H-tetrazolyl, 5H-tetrazolyl, pyridyl, pyrimidinyl, thiadiazole, pyrazinyl and the like, preferably imidazolyl, pyrazolyl, pyrimidinyl, thiazolyl, and more preferably pyrazolyl or imidazolyl. The heteroaryl ring can be fused to the ring of aryl, heterocyclyl or cycloalkyl, wherein the ring bound to the parent structure is heteroaryl ring. Non-limiting examples thereof include:

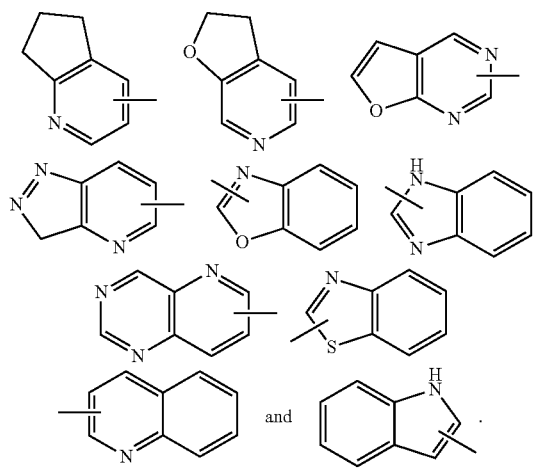

The heteroaryl can be optionally substituted or unsubstituted. When substituted, the substituent group can be substituted at any available connection point. The substituent group is one or more group(s) independently optionally selected from the group consisting of halogen, alkyl, haloalkyl, alkoxy, haloalkoxy, alkylthio, alkylamino, alkenyl, alkynyl, thiol, hydroxy, hydroxyalkyl, cyano, amino, nitro, cycloalkyl, heterocyclyl, aryl, heteroaryl, cycloalkoxy, heterocycloalkoxy, cycloalkylthio, heterocyclylthio and oxo.

The term "amino protecting group" refers to a group which prevents an amino group from reaction when other parts of the molecular are subject to a reaction, and can be easily removed. Non-limiting examples include tert-butoxy carbonyl, acetyl, benzyl, allyl, 2,4-dimethoxy benzyl, p-methoxybenzyl and the like. These groups can be optionally substituted by one to three substituent(s) selected from the group consisting of halogen, alkoxy and nitro. The amino protecting group is preferably 2,4-dimethoxy benzyl.

The term "haloalkyl" refers to an alkyl group substituted by one or more halogen(s), wherein the alkyl is as defined above.

The term "haloalkoxy" refers to an alkoxy group substituted by one or more halogen(s), wherein the alkoxy is as defined above.

The term "hydroxy" refers to an —OH group.

The term "hydroxyalkyl" refers to an alkyl group substituted by hydroxy(s), wherein the alkyl is as defined above.

The term "halogen" refers to fluorine, chlorine, bromine or iodine.

The term "amino" refers to a —$NH_2$ group.

The term "cyano" refers to a —CN group.

The term "nitro" refers to a —$NO_2$ group.

The term "Oxo" refers to a =O group.

"Optional" or "optionally" means that the event or circumstance described subsequently can, but need not, occur, and such a description includes the situation in which the event or circumstance does or does not occur. For example, "the heterocyclyl optionally substituted by an alkyl" means that an alkyl group can be, but need not be, present, and such a description includes the situation of the heterocyclyl being substituted by an alkyl and the heterocyclyl being not substituted by an alkyl.

"Substituted" refers to one or more hydrogen atoms in a group, preferably up to 5, and more preferably 1 to 3 hydrogen atoms, independently substituted by a corresponding number of substituents. It goes without saying that the substituents only exist in their possible chemical position. The person skilled in the art is able to determine whether the substitution is possible or impossible by experiments or theory without paying excessive efforts. For example, the combination of amino or hydroxy having free hydrogen and carbon atoms having unsaturated bonds (such as olefinic) may be unstable.

A "pharmaceutical composition" refers to a mixture of one or more of the compounds described herein or physiologically/pharmaceutically acceptable salts or prodrugs thereof with other chemical components, and other components such as physiologically/pharmaceutically acceptable carriers and excipients. The purpose of the pharmaceutical composition is to facilitate administration of a compound to an organism, which is conducive to the absorption of the active ingredient so as to show biological activity.

A "pharmaceutically acceptable salt" refers to a salt of the compound of the present invention, which is safe and effective in mammals and has the desired biological activity:

The TLR8 agonists disclosed in the prior art have poor selectivity to Cyp and hERG. Therefore, it is still necessary to continue to develop safe and therapeutically more effective TLR8 agonists.

In view of the problems of the prior art, the present invention provides a pharmaceutical compound with better selectivity to Cyp and hERG, better selectivity to TLR8 and more obvious activating effect, which is a safer and more effective TLR8 agonist.

Synthesis Method of the Compound of the Present Invention

In order to achieve the object of the present invention, the present invention applies the following technical solutions.

Scheme I

A method for preparing the compound of formula (I) or a tautomer, mesomer, racemate, enantiomer, diastereomer thereof, or mixture thereof, or a pharmaceutically acceptable salt thereof of the present invention, comprises the following steps of:

Step 1:

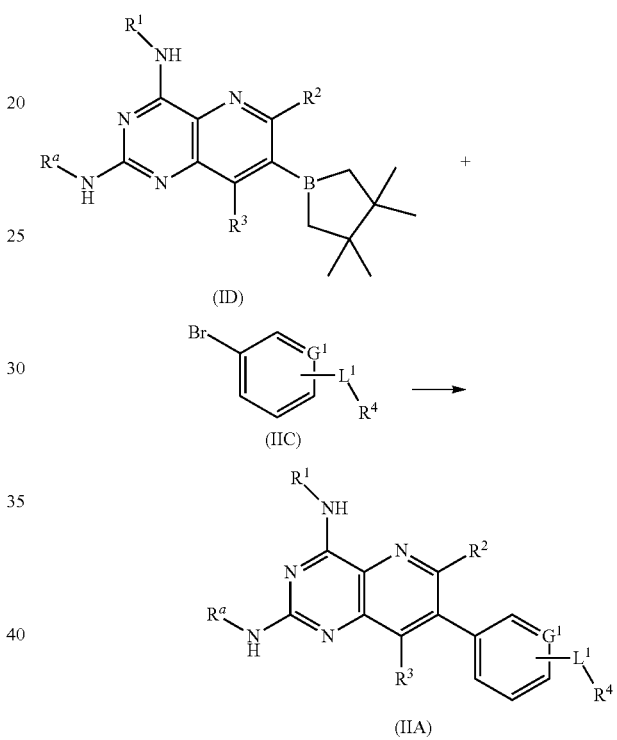

a compound of formula (ID) and a compound of formula (IC) are subjected to a coupling reaction under an alkaline condition in the presence of a catalyst to obtain a compound of formula (IA);

Step 2:

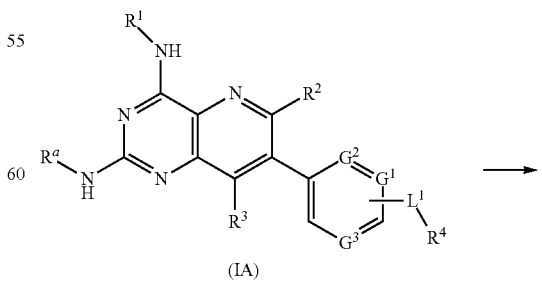

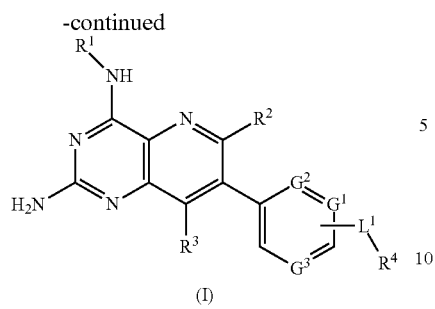

(I)

the compound of formula (IA) is subjected to a deprotection reaction under an acidic condition to obtain the compound of formula (I);

wherein:

$R^a$ is an amino protecting group, and preferably 2,4-dimethoxybenzyl; and $G^1$ to $G^3$, $L^1$ and $R^1$ to $R^4$ are as defined in formula (I).

Scheme II

A method for preparing the compound of formula (Ia) or a tautomer, mesomer, racemate, enantiomer, diastereomer thereof, or mixture thereof, or a pharmaceutically acceptable salt thereof of the present invention, comprises the following step of:

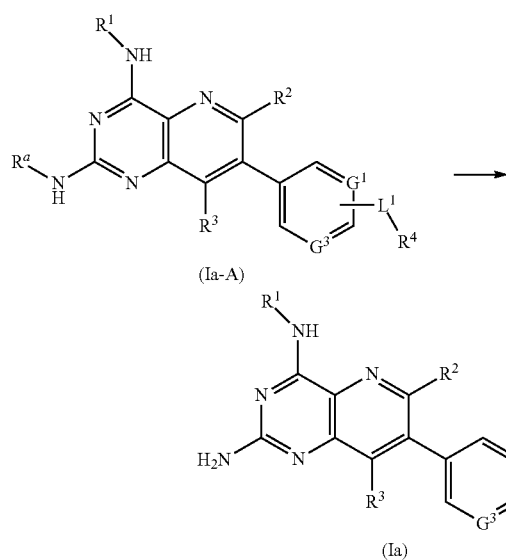

(Ia-A)

(Ia)

a compound of formula (Ia-A) is subjected to a deprotection reaction under an acidic condition to obtain the compound of formula (Ia);

wherein:

$R^a$ is an amino protecting group, and preferably 2,4-dimethoxybenzyl; and $G^1$, $G^3$, $L^1$ and $R^1$ to $R^4$ are as defined in formula (Ia).

Scheme III

A method for preparing the compound of formula (Ib) or a tautomer, mesomer, racemate, enantiomer, diastereomer thereof, or mixture thereof, or a pharmaceutically acceptable salt thereof of the present invention, comprises the following step of:

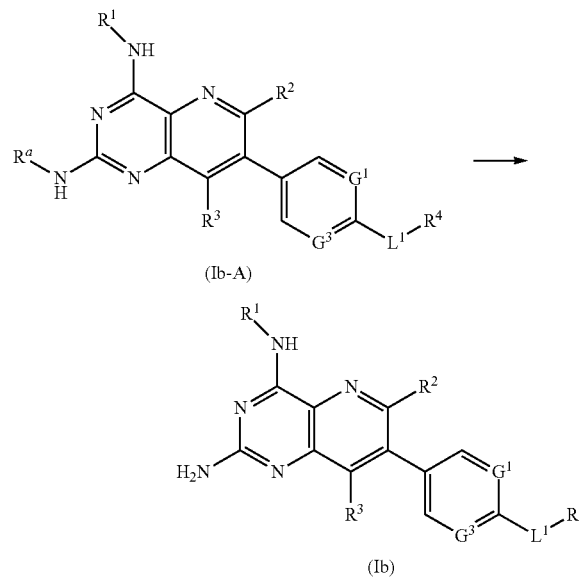

(Ib-A)

(Ib)

a compound of formula (Ib-A) is subjected to a deprotection reaction under an acidic condition to obtain the compound of formula (Ib);

wherein:

$R^a$ is an amino protecting group, and preferably 2,4-dimethoxybenzyl; and $G^1$, $G^3$, $L^1$ and $R^1$ to $R^4$ are as defined in formula (Ib).

Scheme IV

A method for preparing the compound of formula (II) or a tautomer, mesomer, racemate, enantiomer, diastereomer thereof, or mixture thereof, or a pharmaceutically acceptable salt thereof of the present invention, comprises the following steps of:

Step 1:

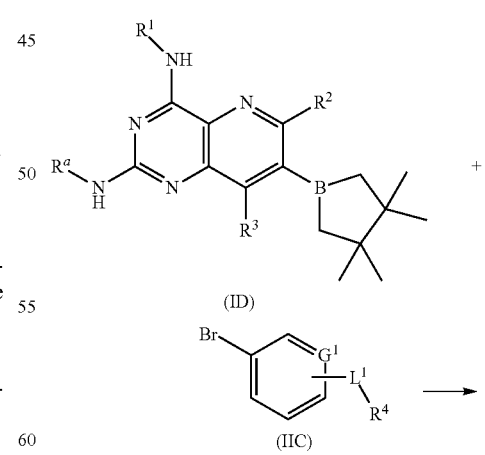

(ID)

(IIC)

-continued

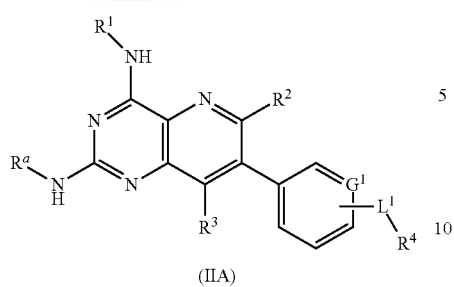

(IIA)

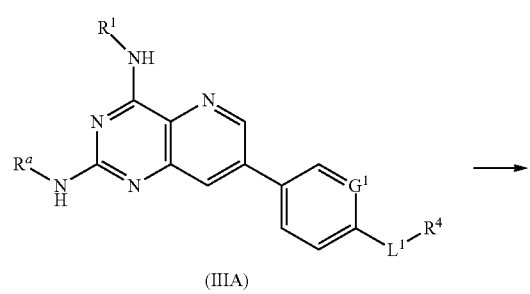

(IIIA)

a compound of formula (ID) and a compound of formula (IIC) are subjected to a coupling reaction under an alkaline condition in the presence of a catalyst to obtain a compound of formula (IIA);

Step 2:

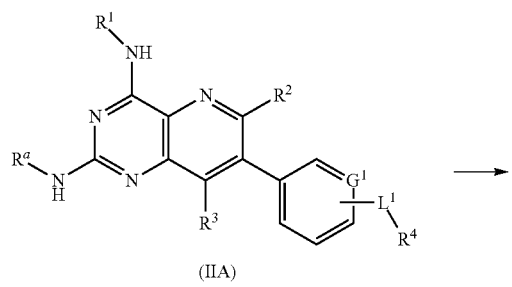

(IIA)

→

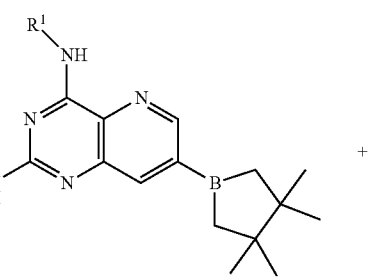

(III)

a compound of formula (IIIA) is subjected to a deprotection reaction under an acidic condition to obtain the compound of formula (III);

wherein:

$R^a$ is an amino protecting group, and preferably 2,4-dimethoxybenzyl; and $G^1$, $L^1$ and $R^1$ and $R^4$ are as defined in formula (III).

Scheme VI

A method for preparing the compound of formula (IVa) or a tautomer, mesomer, racemate, enantiomer, diastereomer thereof, or mixture thereof, or a pharmaceutically acceptable salt thereof of the present invention, comprises the following steps of:

Step 1:

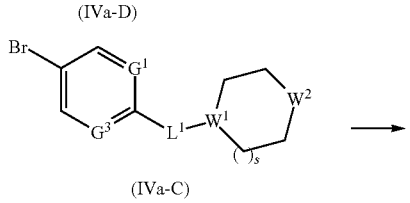

(IVa-D)

+

(II)

the compound of formula (IIA) is subjected to a deprotection reaction under an acidic condition to obtain the compound of formula (II);

wherein:

$R^a$ is an amino protecting group, and preferably 2,4-dimethoxybenzyl; and $G^1$, $L^1$ and $R^1$ to $R^4$ are as defined in formula (II).

Scheme V

A method for preparing the compound of formula (III) or a tautomer, mesomer, racemate, enantiomer, diastereomer thereof, or mixture thereof, or a pharmaceutically acceptable salt thereof of the present invention, comprises the following step of:

(IVa-C)

-continued

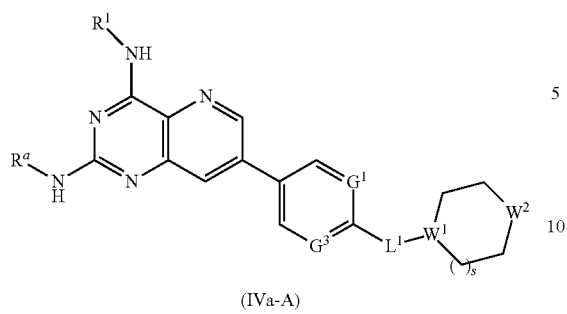

(IVa-A)

a compound of formula (IVa-D) and a compound of formula (IVa-C) are subjected to a coupling reaction under an alkaline condition in the presence of a catalyst to obtain a compound of formula (IVa-A);

Step 2:

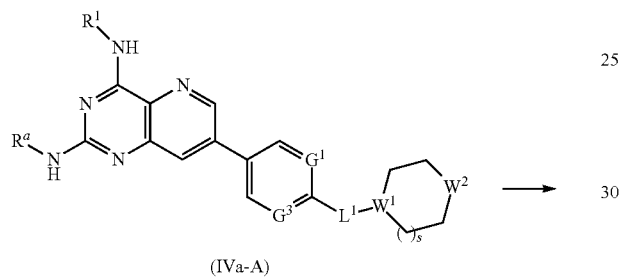

(IVa-A)

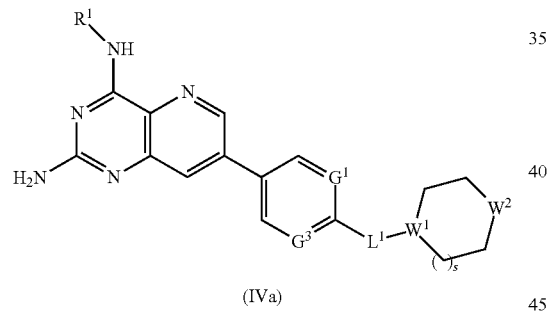

(IVa)

the compound of formula (IVA) is subjected to a deprotection reaction under an acidic condition to obtain the compound of formula (IV);

wherein:

$R^a$ is an amino protecting group, and preferably 2,4-dimethoxybenzyl; and $G^1$, $G^3$, $L^1$, $R^1$, $W^1$, $W^2$ and s are as defined in formula (IV).

Scheme VII

A method for preparing the compound of formula (IV) or a tautomer, mesomer, racemate, enantiomer, diastereomer thereof, or mixture thereof, or a pharmaceutically acceptable salt thereof of the present invention, comprises the following steps of:

step 1:

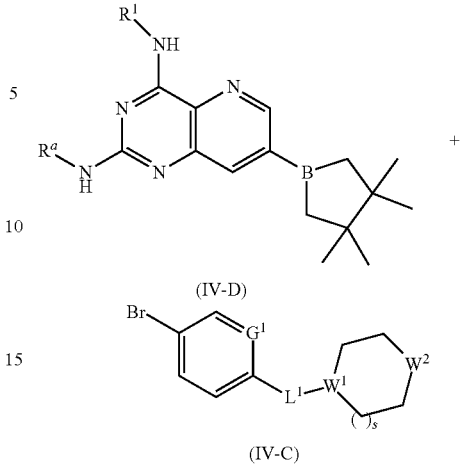

(IV-D)

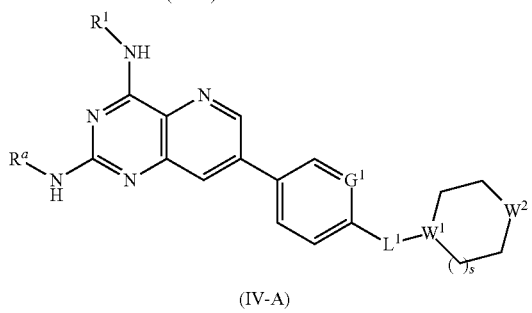

(IV-C)

(IV-A)

a compound of formula (IV-D) and a compound of formula (IV-C) are subjected to a coupling reaction under an alkaline condition in the presence of a catalyst to obtain a compound of formula (IV-A);

step 2:

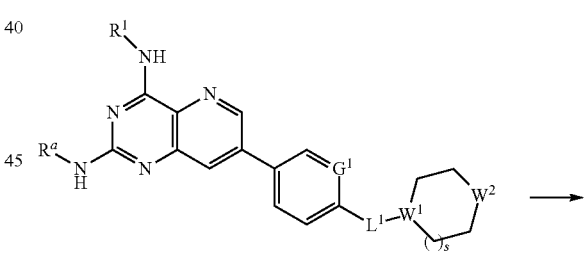

(IVA)

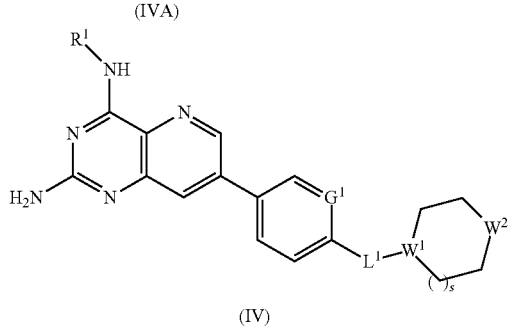

(IV)

the compound of formula (IVA) is subjected to a deprotection reaction under an acidic condition to obtain the compound of formula (IV);

wherein:

R<sup>a</sup> is an amino protecting group, and preferably 2,4-dimethoxybenzyl; and G¹, L¹, R¹, W¹, W² and s are as defined in formula (IV).

Scheme VIII

A method for preparing the compound of formula (Va) or a tautomer, mesomer, racemate, enantiomer, diastereomer thereof, or mixture thereof, or a pharmaceutically acceptable salt thereof of the present invention, comprises the following step of:

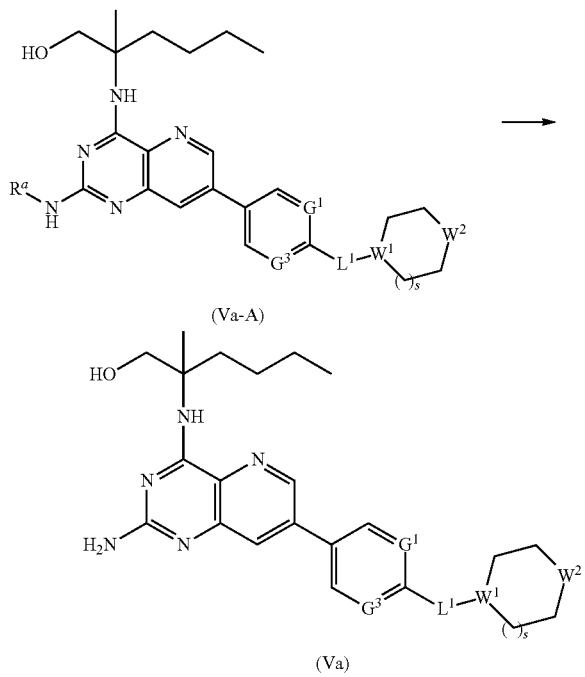

(Va-A)

(Va)

a compound of formula (Va-A) is subjected to a deprotection reaction under an acidic condition to obtain the compound of formula (Va);

wherein:

R<sup>a</sup> is an amino protecting group, and preferably 2,4-dimethoxybenzyl; and G¹, G³, L¹, W¹, W² and s are as defined in formula (Va).

The reagent that provides an acidic condition includes, but is not limited to, hydrogen chloride, a solution of hydrogen chloride in 1,4-dioxane, trifluoroacetic acid, formic acid, acetic acid, hydrochloric acid, sulfuric acid, methanesulfonic acid, nitric acid, phosphoric acid, p-toluenesulfonic acid, Me₃SiCl and TMSOTf, and preferably trifluoroacetic acid.

The above reaction is preferably carried out in a solvent. The solvent used includes, but is not limited to, acetic acid, trifluoroacetic acid, methanol, ethanol, toluene, tetrahydrofuran, dichloromethane, petroleum ether, ethyl acetate, n-hexane, dimethyl sulfoxide, 1,4-dioxane, water, N,N-dimethylformamide, and mixtures thereof.

In the above schemes, the reagent that provides an alkaline condition includes organic bases and inorganic bases. The organic bases include, but are not limited to, triethylamine, N,N-diisopropylethylamine, n-butyllithium, lithium diisopropylamide, lithium bistrimethylsilylamide, potassium acetate, potassium acetate, sodium tert-butoxide, potassium tert-butoxide and sodium n-butoxide. The inorganic bases include, but are not limited to, sodium bicarbonate, potassium bicarbonate, sodium hydride, potassium phosphate, sodium carbonate, potassium carbonate, potassium acetate, cesium carbonate, sodium hydroxide and lithium hydroxide, and preferably potassium carbonate.

The catalyst includes, but is not limited to, Pd/C, tetrakis(triphenylphosphine)palladium, palladium dichloride, palladium acetate, bis(dibenzylideneacetone)palladium, chloro (2-dicyclohexylphosphino-2',4',6'-triisopropyl-1,1'-biphenyl)[2-(2'-amino-1,1'-biphenyl)]palladium, 1,1'-bisdiphenyl phosphinoferrocene palladium dichloride, 1,1'-bis(dibenzylphosphorus) dichloroferrocene palladium or tris(dibenzylideneacetone) dipalladium, and preferably 1,1'-bisdiphenylphosphinoferrocene palladium dichloride.

EXAMPLES

The structures of the compounds were identified by nuclear magnetic resonance (NMR) and/or mass spectrometry (MS). NMR shifts (δ) are given in $10^{-6}$ (ppm). NMR is determined by a Bruker AVANCE-400 machine. The solvents for determination are deuterated-dimethyl sulfoxide (DMSO-$d_6$), deuterated-chloroform (CDCl$_3$) and deuterated-methanol (CD$_3$OD), and the internal standard is tetramethylsilane (TMS).

MS is determined by a FINNIGAN LCQAd (ESI) mass spectrometer (manufacturer: Thermo, type: Finnigan LCQ advantage MAX).

High performance liquid chromatography (HPLC) analysis is determined on an Agilent HPLC 1200DAD, Agilent HPLC 1200VWD and Waters HPLC e2695-2489 high pressure liquid chromatographs.

Chiral HPLC analysis is determined on an Agilent 1260 DAD high performance liquid chromatograph.

Preparative high performance liquid chromatography is carried out on Waters 2767, Waters 2767-SQ Detecor2, Shimadzu LC-20AP and Gilson-281 preparative chromatographs.

Chiral preparative HPLC is carried out on a Shimadzu LC-20AP preparative chromatograph.

CombiFlash rapid preparation instrument used is Combiflash Rf200 (TELEDYNE ISCO).

Yantai Huanghai HSGF254 or Qingdao GF254 silica gel plate is used as the thin-layer silica gel chromatography (TLC) plate. The dimension of the silica gel plate used in TLC is 0.15 mm to 0.2 mm, and the dimension of the silica gel plate used in product purification is 0.4 mm to 0.5 mm.

Yantai Huanghai 200 to 300 mesh silica gel is generally used as a carrier for silica gel column chromatography.

The average kinase inhibition rates and IC$_{50}$ values are determined by a NovoStar ELISA (BMG Co., Germany).

The known starting materials of the present invention can be prepared by the known methods in the art, or can be purchased from ABCR GmbH & Co. KG, Acros Organics, Aldrich Chemical Company, Accela ChemBio Inc., Chembee Company and the like.

Unless otherwise stated, the reactions are carried out under argon atmosphere or nitrogen atmosphere.

"Argon atmosphere" or "nitrogen atmosphere" means that a reaction flask is equipped with an argon or nitrogen balloon (about 1 L).

"Hydrogen atmosphere" means that a reaction flask is equipped with a hydrogen balloon (about 1 L).

Pressurized hydrogenation reactions are performed on a Parr 3916EKX hydrogenation instrument and a Qinglan QL-500 hydrogen generator or HC2-SS hydrogenation instrument.

For hydrogenation reactions, the reaction system is generally vacuumed and filled with hydrogen, and the above operation is repeated three times.

CEM Discover-S 908860 microwave reactor is used for microwave reactions.

Unless otherwise stated, the solution refers to an aqueous solution.

Unless otherwise stated, the reaction temperature is room temperature from 20° C. to 30° C.

The reaction process in the examples is monitored by thin layer chromatography (TLC). The developing solvent used in the reactions, the eluent system in column chromatography and the developing solvent system in thin layer chromatography for purification of the compounds included: A: dichloromethane/methanol system, B: n-hexane/ethyl acetate system, and C: petroleum ether/ethyl acetate system. The ratio of the volume of the solvent is adjusted according to the polarity of the compounds, and a small quantity of alkaline reagent such as triethylamine or acidic reagent such as acetic acid can also be added for adjustment.

Example 1

2-((2-Amino-7-(6-(pyrrolidin-1-ylmethyl)pyridin-3-yl)pyrido[3,2-d]pyrimidin-4-yl)amino)-2-methyl-hexan-1-ol 1

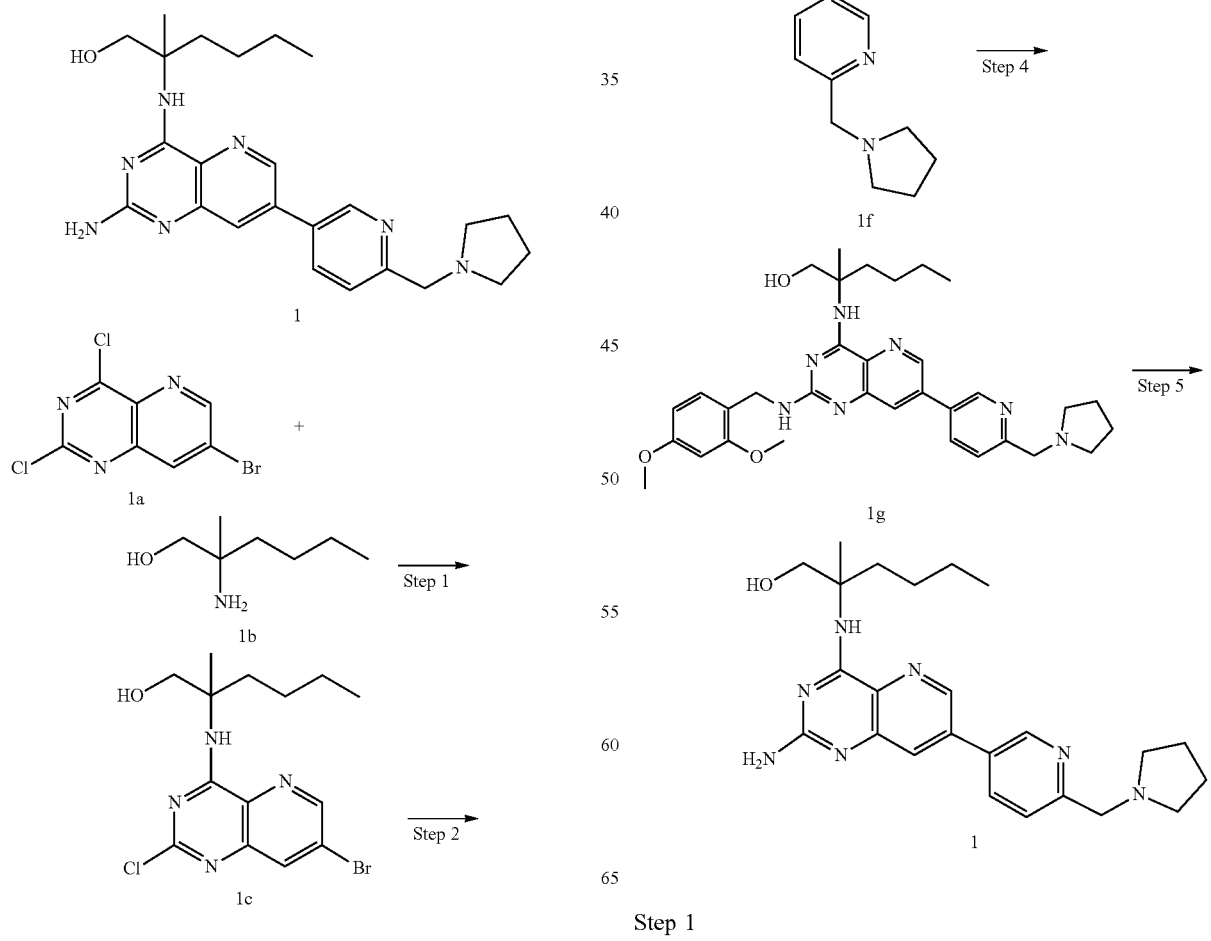

Step 1

2-((7-Bromo-2-chloropyrido[3,2-d]pyrimidin-4-yl)amino)-2-methylhexan-1-ol 1c 7-Bromo-2,4-dichloropyrido[3,2-d]pyrimidine 1a (5.4 g, 19.36 mmol, prepared according to the method disclosed in the patent application WO2014022728) was added to 120 mL of acetonitrile, followed by the addition of 2-amino-2-methylhexan-1-ol 1b (3.8 g, 28.96 mmol, prepared according to the method disclosed in the patent application WO2009129097) and potassium carbonate (8.027 g, 58.08 mmol). The reaction solution was stirred at 45° C. for 16 hours. After completion of the reaction, the insoluble matter was removed by filtration, and the filtrate was concentrated under reduced pressure. The residues were purified by silica gel column chromatography with eluent system A to obtain the title product 1c (4.0 g, yield: 55.3%).

MS m/z (ESI): 373.1 [M+1].

Step 2

2-((7-Bromo-2-((2,4-dimethoxybenzyl)amino)pyrido[3,2-d]pyrimidin-4-yl)amino)-2-methylhexan-1-ol 1d Compound 1c (4.0 g, 10.71 mmol) was added to 25 mL of tetrahydrofuran, followed by the addition of 2,4-dimethoxybenzylamine (6.0 g, 35.861 mmol) and N,N-diisopropylethylamine (4.15 g, 32.11 mmol). The reaction solution was sealed in a tube and stirred at 100° C. for 16 hours. 20 ml of water was added to the reaction solution, which was then extract with dichloromethane (20 mL×3). The organic phases were combined, washed with water (50 mL) and saturated sodium chloride solution (50 mL) respectively, dried over anhydrous magnesium sulfate, and filtered to remove the desiccant. The filtrate was concentrated under reduced pressure. The residues were purified by silica gel column chromatography with eluent system B to obtain the title product 1d (3.5 g, yield: 64.8%).

MS m/z (ESI):504.1 [M+1].

Step 3

2-((2-((2,4-Dimethoxy benzyl)amino)-7-(4,4,5,5-tetramethyl-1,3,2-dioxaborolan-2-yl)pyrido[3,2-d]pyrimidin-4-yl)amino)-2-methylhexan-1-ol 1e Compound 1d (130 mg, 0.237 mmol) was added to 5 mL of ethylene glycol dimethyl ether, followed by the addition of bis(pinacolato)diboron (91 mg, 0.358 mmol). 1,1'-bisdiphenylphosphinoferrocene palladium dichloride (35 mg, 0.048 mmol) and potassium acetate (70 mg, 0.713 mmol). The reaction solution was purged with argon three times, warmed to 80° C. and stirred for 2 hours. The reaction solution was concentrated under reduced pressure. 20 ml of water was added to the resulting system, which was then extracted with dichloromethane (10 mL×3). The organic phases were combined, washed with water (20 mL) and saturated sodium chloride solution (20 mL) respectively, dried over anhydrous magnesium sulfate, and filtered to remove the desiccant. The filtrate was concentrated under reduced pressure to obtain the crude title product 1e (130 mg, yield: 99.2%).

Step 4

2-((2-((2,4-Dimethoxy benzyl)amino)-7-(6-(pyrrolidin-1-ylmethyl)pyridin-3-yl)pyrido[3,2-d]pyrimidin-4-xl)amino)-2-methylhexan-1-ol 1g The crude compound 1e (130 mg, 0.235 mmol) was added to 10 mL of 1,4-dioxane and 2 mL of water, followed by the addition of 5-bromo-2-(pyrrolidin-1-ylmethyl)pyridine 1f (68 mg, 0.282 mmol, prepared according to the method disclosed in the patent application WO2007084451), potassium carbonate (49 mg, 0.355 mmol) and 1,1'-bisdiphenylphosphinoferrocene palladium dichloride (18 mg, 0.025 mmol). The reaction solution was purged with argon three times, warmed to 80° C. and reacted for 2 hours. The reaction solution was concentrated under reduced pressure. 20 ml of water was added to the reaction solution, which was then extracted with dichloromethane (20 mL). The organic phases were combined, washed with water (50) mL) and saturated sodium chloride solution (50 mL), dried over anhydrous magnesium sulfate, and filtered to remove the desiccant. The filtrate was concentrated under reduced pressure. The residues were purified by silica gel column chromatography with eluent system B to obtain the product 1g (60 mg, yield: 43.5%).

MS m/z (ESI): 586.0 [M+1].

Step 5

2-((2-Amino-7-(6-(pyrrolidin-1-ylmethyl)pyridin-3-yl)pyrido[3,2-d]pyrimidin-4-yl)amino)-2-methylhexan-1-ol 1

Compound 1g (60 mg, 0.102 mmol) was added to 10 mL of trifluoroacetic acid, and reacted at room temperature for 2 hours. The reaction solution was concentrated under reduced pressure. 20 ml of saturated sodium bicarbonate solution was added to the reaction solution, which was then extracted with dichloromethane (20 mL×3). The organic phases were combined, washed with water (50 mL) and saturated sodium chloride solution (50 mL), dried over anhydrous magnesium sulfate, and filtered to remove the desiccant. The filtrate was concentrated under reduced pressure. The residues were purified by silica gel column chromatography with eluent system B to obtain the product 1 (10 mg, yield: 22.4%).

MS m/z (ESI): 436.0 [M+1].

$^1$H NMR (400 MHZ, DMSO-$d_6$) δ 8.91 (s, 1H), 8.64 (s, 1H), 8.18-8.20 (m, 1H), 7.83 (s, 1H), 7.56-7.58 (m, 1H), 7.24 (s, 1H), 6.40 (br, 2H), 5.16-5.20 (m, 1H), 3.79 (s, 2H), 3.70-3.73 (m, 1H), 3.51-3.54 (m, 1H), 2.54 (s, 4H), 1.91-1.95 (m, 2H), 1.71-1.75 (m, 4H), 1.43 (s, 3H), 1.23-1.27 (m, 4H), 0.84-0.87 (m, 3H).

Example 2

(R)-2-((2-Amino-7-(6-(pyrrolidin-1-ylmethyl)pyridin-3-yl)pyrido[3,2-d]pyrimidin-4-yl)amino)-2-methylhexan-1-ol 2

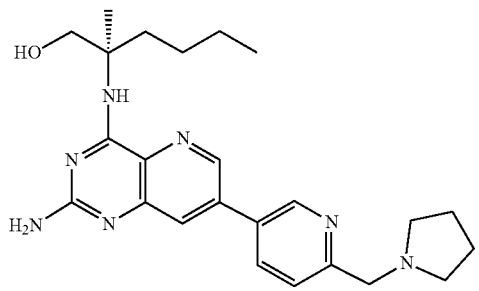

2

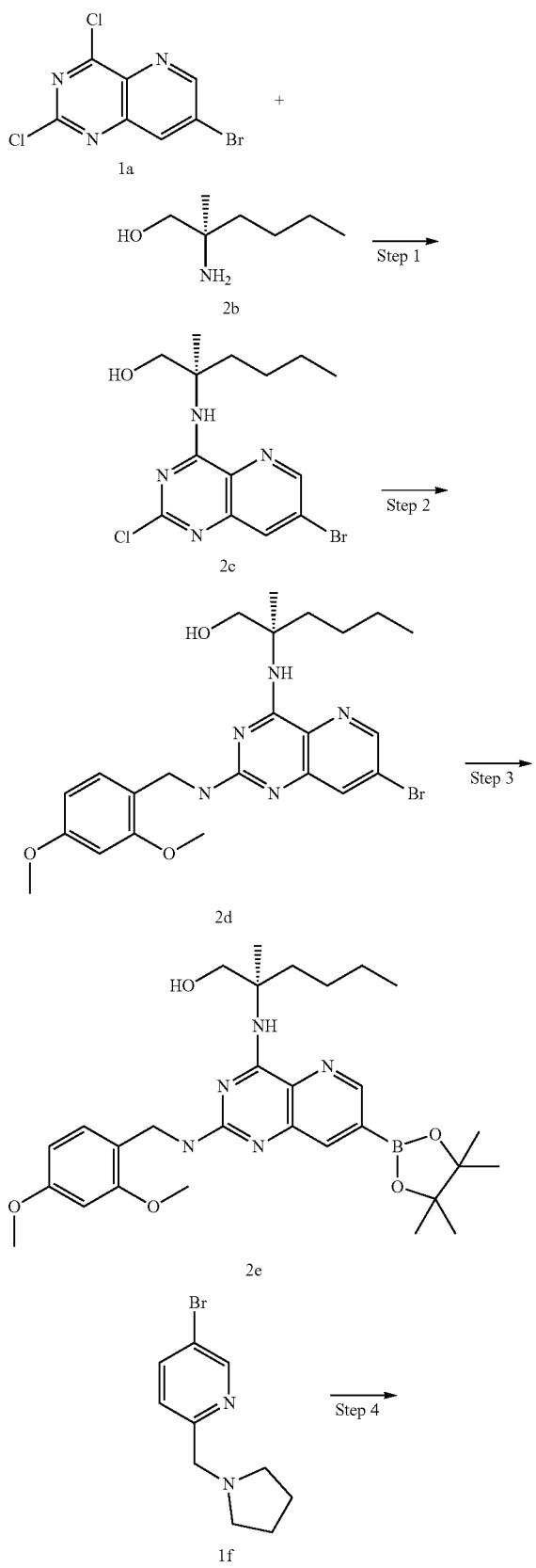
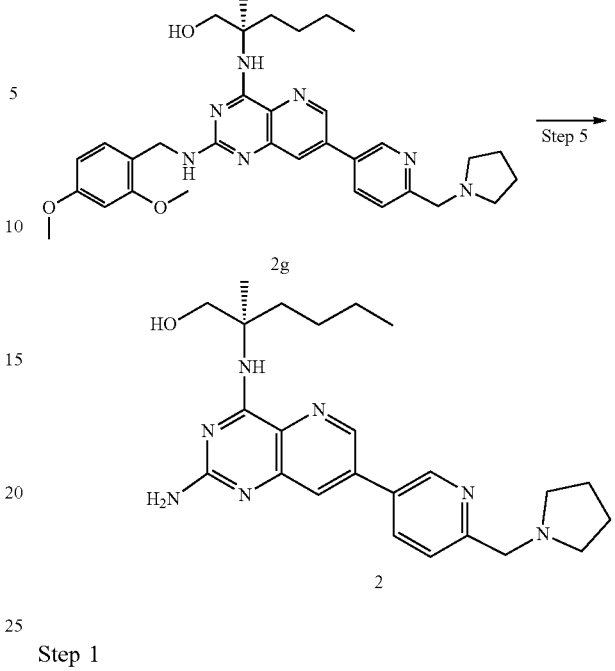

Step 1

(R)-2-((7-Bromo-2-chloropyrido[3,2-d]pyrimidin-4-yl)amino)-2-methylhexan-1-ol 2c Compound 1a (400 mg, 1.434 mmol) was added to 10 mL of tetrahydrofuran, followed by the addition of (R)-2-amino-2-methylhexan-1-ol 2b (prepared according to the method disclosed in the Example 59 on page 207 of the description of the patent application WO2016141092) (377 mg, 2.873 mmol) and N,N-diisopropylethylamine (556 mg, 4.302 mmol). The reaction solution was sealed in a tube and stirred at 100° C. for 16 hours. After completion of the reaction, the reaction solution was cooled to room temperature, and the insoluble matter was removed by filtration. The filtrate was concentrated under reduced pressure, and the resulting residues were purified by silica gel column chromatography with eluent system A to obtain the title product 2c (4.0 g, yield: 55.3%).

MS m/z (ESI): 373.1 [M+1].

Step 2

(R)-2-((7-Bromo-2-((2,4-dimethoxybenzyl)amino)pyrido[3,2-d]pyrimidin-4-yl)amino)-2-methylhexan-1-ol 2d Compound 2c (250 mg, 0.669 mmol) was added to 10 mL of tetrahydrofuran, followed by the addition of 2,4-dimethoxybenzylamine (560 mg, 3.349 mmol) and N,N-diisopropylethylamine (259 mg, 2.004 mmol). The reaction solution was sealed in a tube and stirred at 100° C. for 16 hours. 20 ml of water was added to the reaction solution, which was then extract with dichloromethane (20 mL×3). The organic phases were combined, washed with water (20 mL) and saturated sodium chloride solution (20) mL) respectively, dried over anhydrous magnesium sulfate, and filtered to remove the desiccant. The filtrate was concentrated under reduced pressure. The residues were purified by silica gel column chromatography with eluent system B to obtain the title product 2d (295 mg, yield: 87.5%).

MS m/z (ESI):504.1 [M+1].

Step 3

(R)-2-((2-((2,4-Dimethoxy benzyl)amino)-7-(4,4,5, 5-tetramethyl-1,3,2-dioxaborolan-2-yl)pyrido[3,2-d] pyrimidin-4-yl)amino)-2-methylhexan-1-ol 2e Compound 2d (295 mg, 0.54 mmol) was added to 5 mL of ethylene glycol dimethyl ether, followed by the addition of bis(pinacolato)diboron (223 mg, 878.169 μmol), 1,1'-bisdiphenylphosphinoferrocene palladium dichloride (43 mg, 0.059 mmol) and potassium acetate (173 mg, 1.76 mmol). The reaction solution was purged with argon three times, warmed to 80° C. and stirred for 2 hours. The reaction solution was concentrated under reduced pressure. 20 ml of water was added to reaction system, which was then extracted with dichloromethane (10 mL×3). The organic phases were combined, washed with water (20 mL) and saturated sodium chloride solution (20 mL) respectively, dried over anhydrous magnesium sulfate, and filtered to remove the desiccant. The filtrate was concentrated under reduced pressure to obtain the crude title product 2e (322 mg, yield: 100%).

Step 4

(R)-2-((2-((2,4-Dimethoxybenzyl)amino)-7-(6-(pyrrolidin-1-ylmethyl)pyridin-3-yl)pyrido[3,2-d]pyrimidin-4-yl)amino)-2-methylhexan-1-ol 2g The crude compound 2e (322 mg, 0.584 mmol) was added to 10 mL of 1,4-dioxane and 2 mL of water, followed by the addition of compound 1f (141 mg, 0.584 mmol), potassium carbonate (242 mg, 1.75 mmol) and 1,1'-bisdiphenylphosphinoferrocene palladium dichloride (43 mg, 0.059 mmol). The reaction solution was purged with argon three times, warmed to 80° C. and reacted for 2 hours. The reaction solution was concentrated under reduced pressure. 20 ml of water was added to the reaction solution, which was then extracted with dichloromethane (20 mL). The organic phases were combined, washed with water (50 mL) and saturated sodium chloride solution (50 mL), dried over anhydrous magnesium sulfate, and filtered to remove the desiccant. The filtrate was concentrated under reduced pressure. The residues were purified by silica gel column chromatography with eluent system B to obtain the product 2g (100 mg, yield: 29.2%).

MS m/z. (ESI): 586.0 [M+1]

Step 5

(R)-2-((2-Amino-7-(6-(pyrrolidin-1-ylmethyl)pyridin-3-yl)pyrido[3,2-d]pyrimidin-4-yl)amino)-2-methylhexan-1-ol 2

Compound 2g (100 mg, 0.170 mmol) was added to 10 mL of trifluoroacetic acid, and reacted at room temperature for 2 hours. The reaction solution was concentrated under reduced pressure. 20 ml of saturated sodium bicarbonate solution was added to the reaction solution, which was then extracted with dichloromethane (20 mL×3). The organic phases were combined, washed with water (50 mL) and saturated sodium chloride solution (50 mL), dried over anhydrous magnesium sulfate, and filtered to remove the desiccant. The filtrate was concentrated under reduced pressure. The resulting residues were purified by silica gel column chromatography with eluent system B to obtain the product 2 (45 mg yield: 60.5%).

MS m/z (ESI): 436.0 [M+1].

$^1$H NMR (400 MHZ, DMSO-$d_6$) δ 8.91 (s, 1H), 8.64 (s, 1H), 8.18-8.20 (m, 1H), 7.83 (s, 1H), 7.56-7.58 (m, 1H), 7.24 (s, 1H), 6.40 (br, 2H), 5.16-5.20 (m, 1H), 3.79 (s, 2H), 3.70-3.73 (m, 1H), 3.51-3.54 (m, 1H), 2.54 (s, 4H), 1.91-1.95 (m, 2H), 1.71-1.75 (m, 4H), 1.43 (s, 3H), 1.23-1.27 (m, 4H), 0.84-0.87 (m, 3H).

Example 3

2-((2-Amino-7-(6-(1-methylpiperidin-4-yl)pyridin-3-yl)pyrido[3,2-d]pyrimidin-4-yl)amino)-2-methyl-hexan-1-ol 3

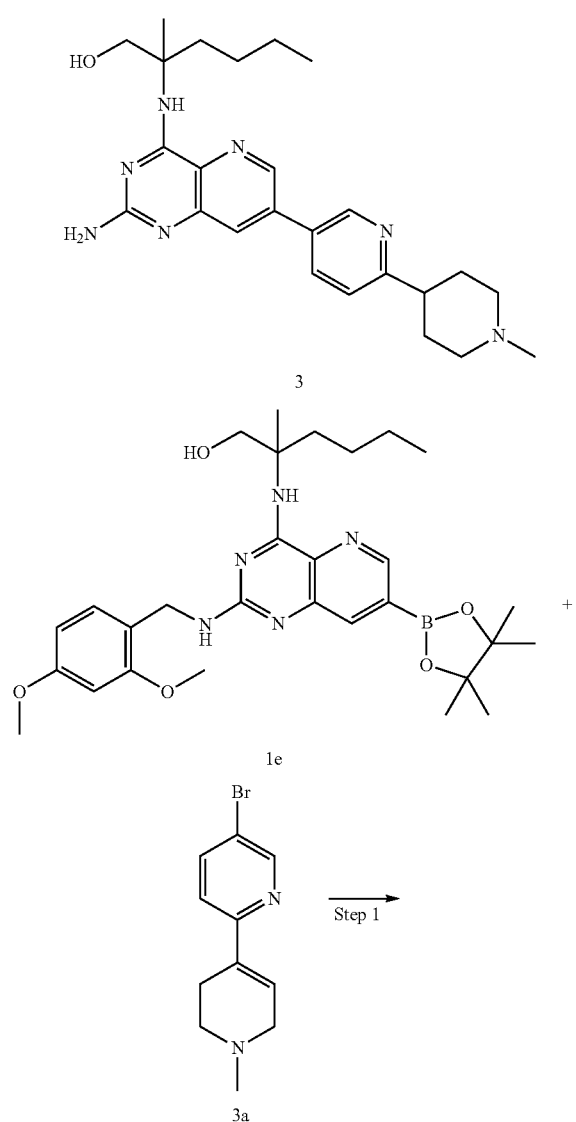

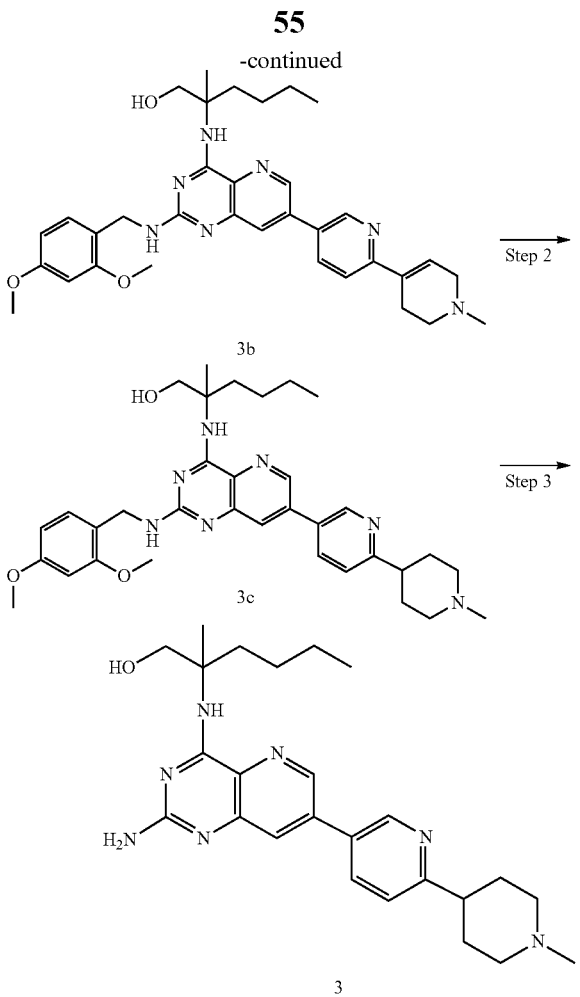

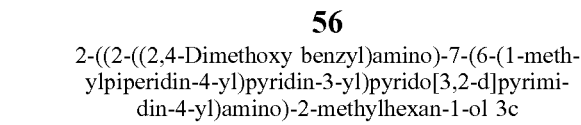

Step 1

2-((2-((2,4-Dimethoxybenzyl)amino)-7-(1'-methyl-1',2',3',6'-tetrahydro-[2,4'-bipyridin]-5-yl)pyrido[3,2-d]pyrimidin-4-yl)amino)-2-methylhexan-1-ol 3b Compound 1e (218 mg, 0.395 mmol) was added to 10 mL of 1,4-dioxane and 2 mL of water, followed by the addition of 5-bromo-1'-methyl-1',2',3',6'-tetrahydro-2,4'-bipyridine 3a (100 mg, 0.395 mmol, prepared according to the method disclosed in the patent application WO2010054279), 1,1'-bisdiphenylphosphinoferrocene palladium dichloride (29 mg, 0.040 mmol) and potassium carbonate (164 mg, 1.187 mmol). The reaction solution was purged with argon three times, warmed to 80° C. and stirred for 2 hours. The reaction solution was concentrated under reduced pressure. 20 ml of water was added to the resulting system, which was then extracted with dichloromethane (10 mL×3). The organic phases were combined, washed with water (20 mL) and saturated sodium chloride solution (30 mL) respectively, dried over anhydrous magnesium sulfate, and filtered to remove the desiccant. The filtrate was concentrated under reduced pressure. The residues were purified by silica gel column chromatography with eluent system B to obtain the title product 3b (100 mg, yield: 43.2%).

MS m/z (ESI): 598.0[M+1].

Step 2

2-((2-((2,4-Dimethoxy benzyl)amino)-7-(6-(1-methylpiperidin-4-yl)pyridin-3-yl)pyrido[3,2-d]pyrimidin-4-yl)amino)-2-methylhexan-1-ol 3c Compound 3b (100 mg, 0.163 mmol) was added to 10 mL of methanol, followed by the addition of Pd/C (20 mg), potassium carbonate (49 mg, 0.355 mmol) and 1,1'-bisdiphenylphosphinoferrocene palladium dichloride (18 mg, 0.025 mmol). The reaction solution was purged with hydrogen five times, and reacted at room temperature for 20 hours. Pd/C was removed by filtration, and the filtrate was concentrated under reduced pressure to obtain the crude title product 3c (68 mg, yield: 67.8%).

MS m/z (ESI): 600.0 [M+1].

Step 3

2-((2-Amino-7-(6-(1-methylpiperidin-4-yl)pyridin-3-yl)pyrido[3,2-d]pyrimidin-4-yl)amino)-2-methylhexan-1-ol 3

The crude compound 3c (60 mg, 0.100 mmol) was added to 5 mL of trifluoroacetic acid, and reacted at room temperature for 3 hours. The reaction solution was concentrated under reduced pressure. 20 ml of saturated sodium bicarbonate solution was added to the reaction solution, which was then extracted with dichloromethane (20) mL×3). The organic phases were combined, washed with saturated sodium chloride solution (30 mL), dried over anhydrous magnesium sulfate, and filtered to remove the desiccant. The filtrate was concentrated under reduced pressure. The residues were purified by silica gel column chromatography with eluent system B to obtain the product 3 (15 mg, yield: 33.4%).

MS m/z (ESI): 450.0 [M+1].

$^1$H NMR (400 MHZ, DMSO-$d_6$) δ 8.91 (s, 1H), 8.62 (s, 1H), 8.11-8.13 (d, 1H), 7.80 (s, 1H), 7.42-7.44 (m, 1H), 7.23 (s, 1H), 6.38 (br, 2H), 3.70-3.72 (m, 1H), 3.50-3.53 (m, 1H), 2.87-2.90 (m, 2H), 2.68-3.72 (m, 1H), 2.00 (s, 3H), 1.83-1.93 (m, 9H), 1.42 (s, 3H), 1.23-1.27 (m, 4H), 0.83-0.86 (m, 3H).

Example 4

(R)-2-((2-Amino-7-(6-(1-methylpiperidin-4-yl)pyridin-3-yl)pyrido[3,2-d]pyrimidin-4-yl)amino)-2-methylhexan-1-ol 4

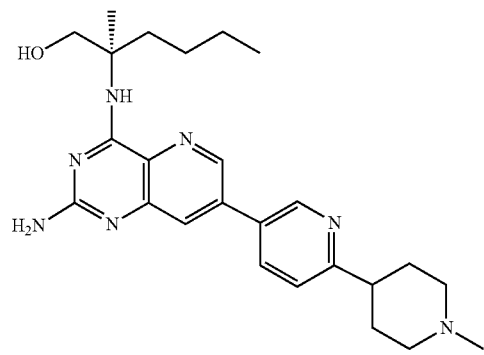

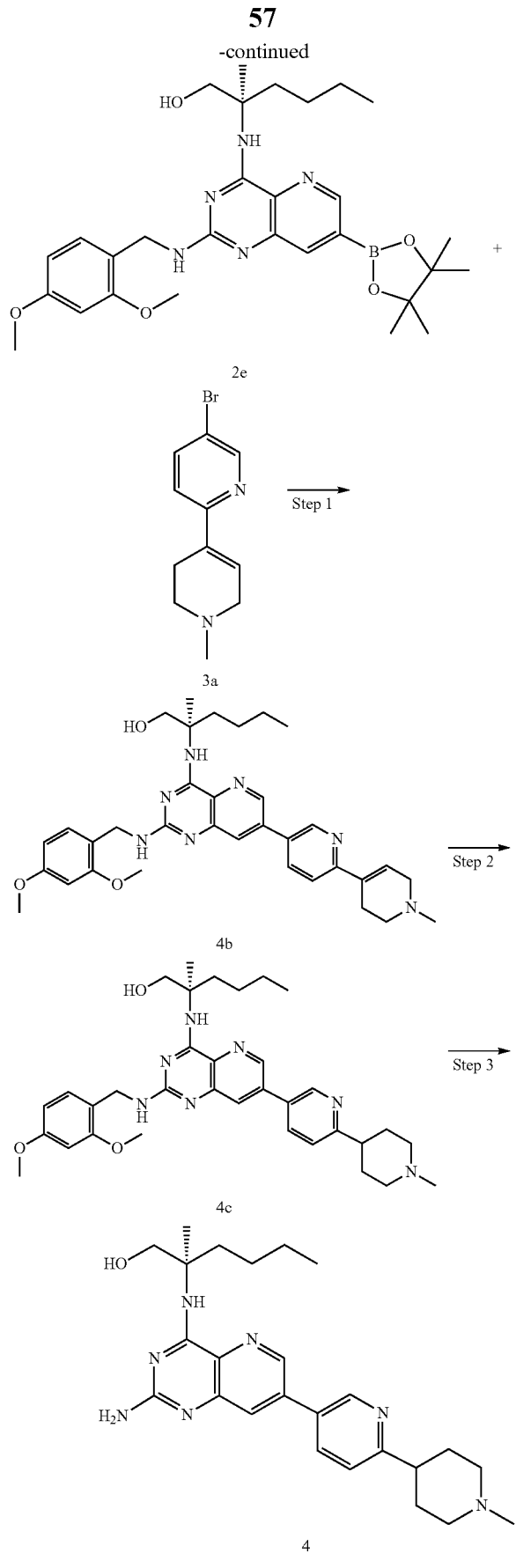

Step 1

(R)-2-((2-((2,4-dimethoxybenzyl)amino)-7-(1'-methyl-1',2',3',6'-tetrahydro-[2,4'-bipyridin]-5-yl)pyrido[3,2-d]pyrimidin-4-yl)amino)-2-methylhexan-1-ol 4b Compound 2e (284 mg, 0.515 mmol) was added to 10 mL of 1,4-dioxane and 2 mL of water, followed by the addition of compound 3a (130 mg, 0.515 mmol), 1,1'-bisdiphenylphosphinoferrocene palladium dichloride (38 mg, 0.052 mmol) and potassium carbonate (214 mg, 1.551 mmol). The reaction solution was purged with argon three times, warmed to 80° C. and stirred for 2 hours. The reaction solution was concentrated under reduced pressure. 20 ml of water was added to the resulting system, which was then extracted with dichloromethane (10 mL×3). The organic phases were combined, washed with water (20 mL) and saturated sodium chloride solution (30 mL) respectively, dried over anhydrous magnesium sulfate, and filtered to remove the desiccant. The filtrate was concentrated under reduced pressure. The residues were purified by silica gel column chromatography with eluent system B to obtain the title product 4b (102 mg, yield: 33.1%).

MS m/z (ESI): 598.0[M+1].

Step 2

(R)-2-((2-((2,4-Dimethoxybenzyl)amino)-7-(6-(1-methylpiperidin-4-yl)pyridin-3-yl)pyrido[3,2-d]pyrimidin-4-yl)amino)-2-methylhexan-1-ol 4c Compound 4b (100 mg, 0.163 mmol) was added to 10 mL of methanol, followed by the addition of Pd/C (20 mg), potassium carbonate (49 mg, 0.355 mmol) and 1,1'-bisdiphenylphosphinoferrocene palladium dichloride (18 mg, 0.025 mmol). The reaction solution was purged with hydrogen five times, and reacted at room temperature for 20 hours. Pd/C was removed by filtration, and the filtrate was concentrated under reduced pressure to obtain the crude title product 4c (85 mg, yield: 84.7%).

MS m/z (ESI): 600.0 [M+1].

Step 3

(R)-2-((2-Amino-7-(6-(1-methylpiperidin-4-yl)pyridin-3-yl)pyrido[3,2-d]pyrimidin-4-yl)amino)-2-methylhexan-1-ol 4

The crude compound 4c (80 mg, 0.133 mmol) was added to 5 mL of trifluoroacetic acid, and reacted at room temperature for 2 hours. The reaction solution was concentrated under reduced pressure. 20 ml of saturated sodium bicarbonate solution was added to the reaction solution, which was then extracted with dichloromethane (20 mL×2). The organic phases were combined, washed with saturated sodium chloride solution (30 mL), dried over anhydrous magnesium sulfate, and filtered to remove the desiccant. The filtrate was concentrated under reduced pressure. The residues were purified by thin layer chromatography with eluent system B to obtain the product 4 (26 mg, yield: 43.3%).

MS m/z (ESI): 450.0 [M+1].

$^1$H NMR (400 MHZ, DMSO-$d_6$) δ 8.91 (s, 1H), 8.62 (s, 1H), 8.11-8.13 (d, 1H), 7.80 (s, 1H), 7.42-7.44 (m, 1H), 7.23 (s, 1H), 6.38 (br, 2H), 3.70-3.72 (m, 1H), 3.50-3.53 (m, 1H), 2.87-2.90 (m, 2H), 2.68-3.72 (m, 1H), 2.00 (s, 3H), 1.83-1.93 (m, 9H), 1.42 (s, 3H), 1.23-1.27 (m, 4H), 0.83-0.86 (m, 3H).

Example 5

2-((2-Amino-7-(6-((4-methylpiperazin-1-yl)methyl)pyridin-3-yl)pyrido[3,2-d]pyrimidin-4-yl)amino)-2-methylhexan-1-ol 5

2-((2-((2,4-Dimethoxy benzyl)amino)-7-(6-((4-methylpiperazin-1-yl)methyl)pyridin-3-yl)pyrido[3,2-d]pyrimidin-4-yl)amino)-2-methylhexan-1-ol 5b Compound 1e (200 mg, 0.363 mmol) was added to 10 mL of 1,4-dioxane and 2 mL water, followed addition of of by the 1-((5-bromopyridin-2-yl)methyl)-4-methylpiperazine 5a (108 mg, 0.401 mmol, prepared according to the method disclosed in the patent application WO20020026052), 1,1'-

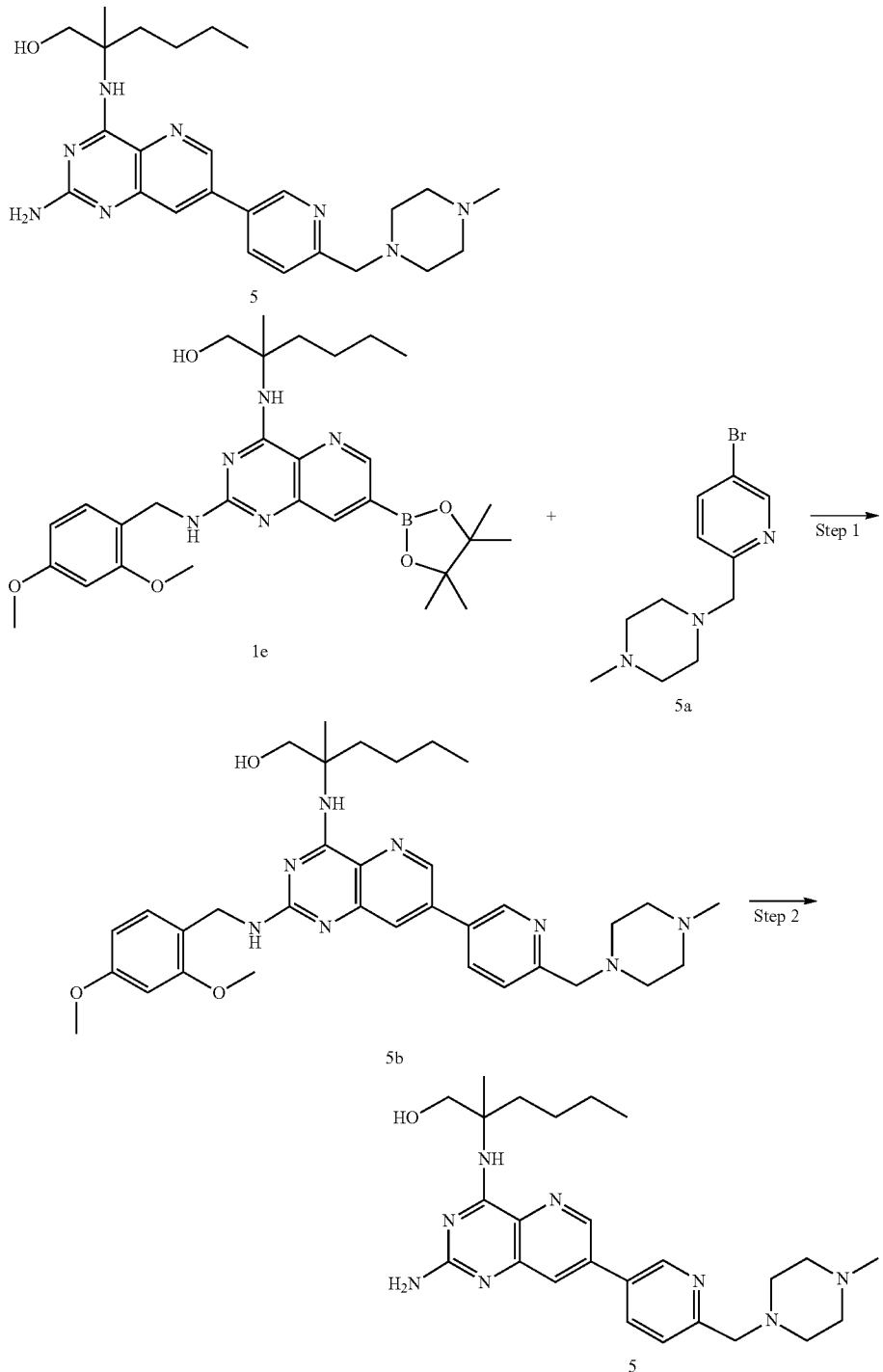

Step 1 bisdiphenylphosphinoferrocene palladium dichloride (27 mg, 0.037 mmol) and potassium carbonate (150 mg, 1.085 mmol). The reaction solution was purged with argon three times, warmed to 80° C. and reacted for 2 hours. The reaction solution was concentrated under reduced pressure. 20 ml of water was added to the reaction system, which was then extracted with dichloromethane (10 mL×3). The organic phases were combined, washed with water (20 mL) and saturated sodium chloride solution (30 mL) respectively, dried over anhydrous magnesium sulfate, and filtered to remove the desiccant. The filtrate was concentrated under reduced pressure. The residues were purified by silica gel column chromatography with eluent system B to obtain the title product 5b (121 mg, yield: 54.2%).

MS m/z (ESI): 615.1 [M+1].

Step 2

2-((2-Amino-7-(6-((4-methylpiperazin-1-yl)methyl) pyridin-3-yl)pyrido[3,2-d]pyrimidin-4-yl)amino)-2-methylhexan-1-ol 5

Compound 5b (85 mg, 0.138 mmol) was added to 5 mL of trifluoroacetic acid, and reacted at room temperature for 3 hours. The reaction solution was concentrated under reduced pressure. 20 ml of saturated sodium bicarbonate solution was added to the reaction solution, which was then extracted with dichloromethane (20 mL×3). The organic phases were combined, washed with saturated sodium chloride solution (30 mL), dried over anhydrous magnesium sulfate, and filtered to remove the desiccant. The filtrate was concentrated under reduced pressure. The residues were purified by silica gel column chromatography with eluent system B to obtain the product 5 (23 mg, yield: 49.5%).

MS m/z (ESI): 465.1 [M+1].

$^1$H NMR (400 MHZ, DMSO-$d_6$) δ 8.87-8.88 (d, 1H), 8.60-8.61 (m, 1H), 8.14-8.16 (d, 1H), 7.79-7.80 (s, 1H), 7.51-7.53 (d, 1H), 7.20 (s, 1H), 6.36 (br, 2H), 5.12-5.15 (t, 1H), 3.66 (s, 2H), 3.68-3.70 (m, 1H), 3.48-2.53 (m, 1H), 2.32-3.42 (m, 8H), 2.12 (s, 3H), 1.90-1.92 (m, 2H), 1.40 (s, 3H), 1.22-1.23 (m, 4H), 0.80-0.84 (m, 3H).

Example 6

(R)-2-((2-Amino-7-(6-((4-methylpiperazin-1-yl) methyl)pyridin-3-yl)pyrido[3,2-d]pyrimidin-4-yl) amino)-2-methylhexan-1-ol 6

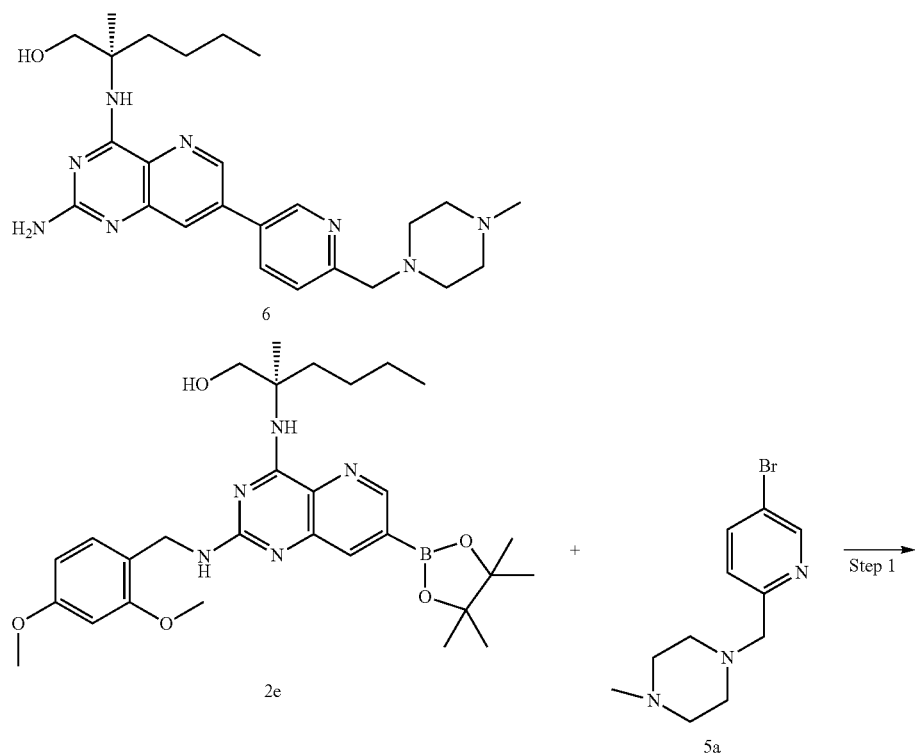

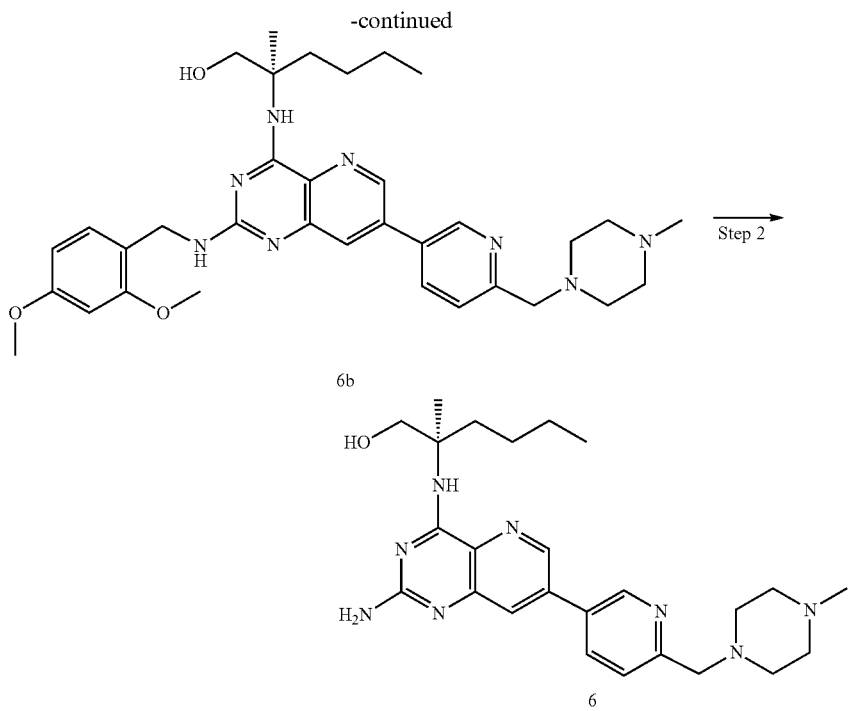

Step 1

(R)-2-((2-(((2,4-Dimethoxy benzyl)amino)-7-(6-((4-methylpiperazin-1-yl)methyl)pyridin-3-yl)pyrido[3,2-d]pyrimidin-4-yl)amino)-2-methylhexan-1-ol 6b Compound 2e (650 mg, 1.178 mmol) was added to 20 mL of 1,4-dioxane and 4 mL of water, followed by the addition of 1-((5-bromopyridin-2-yl)methyl)-4-methylpiperazine 5a (318 mg, 1.170 mmol), 1,1'-bisdiphenylphosphinoferrocene palladium dichloride (86 mg, 0.117 mmol) and potassium carbonate (489 mg, 3.538 mmol). The reaction solution was purged with argon three times, warmed to 80° C. and stirred for 2 hours. The reaction solution was concentrated under reduced pressure. 30 ml of water was added to the reaction system, which was then extracted with dichloromethane (30 mL×3). The organic phases were combined, washed with water (30 mL) and saturated sodium chloride solution (30 mL) respectively, dried over anhydrous magnesium sulfate, and filtered to remove the desiccant. The filtrate was concentrated under reduced pressure. The residues were purified by silica gel column chromatography with eluent system B to obtain the title product 6b (650 mg, yield: 89.70%).

MS m/z (ESI): 615.1 [M+1].

Step 2

(R)-2-((2-Amino-7-(6-((4-methylpiperazin-1-yl)methyl)pyridin-3-yl)pyrido[3,2-d]pyrimidin-4-yl)amino)-2-methylhexan-1-ol 6

Compound 6b (650 mg, 0.138 mmol) was added to 5 mL of trifluoroacetic acid, and reacted at room temperature for 3 hours. The reaction solution was concentrated under reduced pressure. 20 ml of saturated sodium bicarbonate solution was added to the reaction solution, which was then extracted with dichloromethane (20 mL×3). The organic phases were combined, washed with saturated sodium chloride solution (30 mL), dried over anhydrous magnesium sulfate, and filtered to remove the desiccant. The filtrate was concentrated under reduced pressure. The residues were purified by silica gel column chromatography with eluent system B to obtain the product 6 (320 mg yield: 65.14%).

MS m/z (ESI): 465.1[M+1].

$^1$H NMR (400 MHZ, DMSO-$d_6$) δ 8.87-8.88 (d, 1H), 8.60-8.61 (m, 1H), 8.14-8.16 (d, 1H), 7.79-7.80 (s, 1H), 7.51-7.53 (d, 1H), 7.20 (s, 1H), 6.36 (br, 2H), 5.12-5.15 (t, 1H), 3.66 (s, 2H), 3.68-3.70 (m, 1H), 3.48-2.53 (m, 1H), 2.32-3.42 (m, 8H), 2.12 (s, 3H), 1.90-1.92 (m, 2H), 1.40 (s, 3H), 1.22-1.23 (m, 4H), 0.80-0.84 (m, 3H).

Example 7

(R)-2-((2-Amino-7-(2-((4-methylpiperazin-1-yl)methyl)pyrimidin-5-yl)pyrido[3,2-d]pyrimidin-4-yl)amino)-2-methylhexan-1-ol

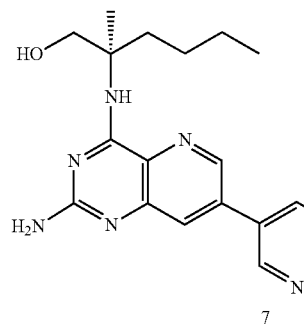
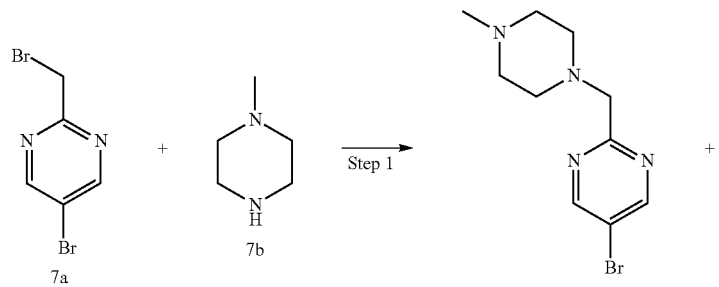
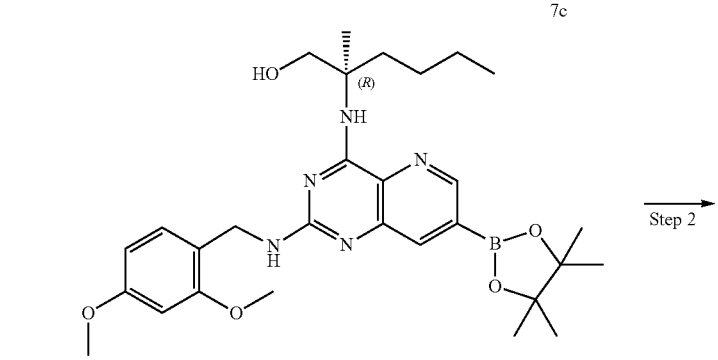
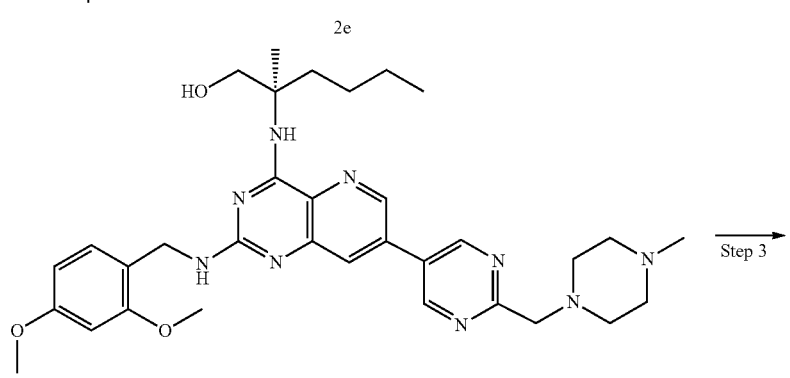

Step 1

5-Bromo-2-((4-methylpiperazin-1-yl)methyl)pyrimidine 7c

Compound 5-bromo-2-(bromomethyl)pyrimidine 7a (200 mg, 0.794 mmol) was added to 5 mL of acetonitrile, followed by the addition of potassium carbonate (220 mg, 1.592 mmol). 1-Methylpiperazine 7b (120 mg, 1.198 mmol) was added at 0° C., and the reaction solution was warmed to room temperature and stirred for 2 hours. After completion of the reaction, the insoluble matter was removed by filtration, and the filtrate was concentrated under reduced pressure. The residues were purified by silica gel column chromatography with eluent system B to obtain the title product 7c (200 mg, yield: 92.9%).

MS m/z (ESI): 273.1 [M+1].

Step 2

(R)-2-((2-(((2,4-Dimethoxy benzyl)amino)-7-(2-((4-methylpiperazin-1-yl)methyl)pyrimidin-5-yl)pyrido[3,2-d]pyrimidin-4-yl)amino)-2-methylhexan-1-ol 7d Compound 2e (163 mg, 0.296 mmol) was added to 5 mL of 1,4-dioxane and 1 mL of water, followed by the addition of 7c (81 mg, 0.299 mmol), tetrakistriphenylphosphonium palladium (35 mg, 0.030 mmol) and potassium carbonate (82 mg, 0.593 mmol). The reaction solution was purged with argon three times, warmed to 100° C. and stirred for 2 hours. The reaction solution was concentrated under reduced pressure. 20 ml of water was added to the reaction system, which was then extracted with dichloromethane (10 mL×3). The organic phases were combined, washed with water (20 mL) and saturated sodium chloride solution (30 mL) respectively, dried over anhydrous magnesium sulfate, and filtered to remove the desiccant. The filtrate was concentrated under reduced pressure. The residues were purified by silica gel column chromatography with eluent system B to obtain the title product 7d (127 mg, yield: 69.8%).

MS m/z (ESI): 616.3[M+1].

Step 3

(R)-2-((2-Amino-7-(2-((4-methylpiperazin-1-yl)methyl)pyrimidin-5-yl)pyrido[3,2-d]pyrimidin-4-yl)amino)-2-methylhexan-1-ol 7

Compound 7d (127 mg, 0.206 mmol) was added to 3 mL of trifluoroacetic acid, and reacted at room temperature for 1 hour. The reaction solution was concentrated under reduced pressure. 20 ml of saturated sodium bicarbonate solution was added to the reaction solution, which was then extracted with dichloromethane (20 mL×3). The organic phases were combined, washed with saturated sodium chloride solution (30 mL), dried over anhydrous magnesium sulfate, and filtered to remove the desiccant. The filtrate was concentrated under reduced pressure. The residues were purified by high performance liquid chromatography (Waters-2767, elution system: $H_2O$ (10 mmol $NH_4OAc$), ACN) to obtain the product 7 (34 mg, yield: 35.4%).

MS m/z (ESI): 466.3 [M+1].

$^1$H NMR (400 MHZ, DMSO-$d_6$) δ 9.19 (s, 2H), 8.66 (s, 1H), 7.92 (s, 1H), 7.23 (s, 1H), 6.40 (br, 2H), 5.15 (br, 1H), 3.73 (s, 2H), 3.70 (d, 2H), 3.50 (d, 2H), 2.51 (br, 3H), 2.29 (br, 3H), 2.11 (s, 3H), 1.90-1.88 (m, 2H), 1.41 (s, 3H), 1.28-1.20 (m, 4H), 0.83 (t, 3H).

Example 8

(R)-2-((2-Amino-7-(2-(1-methylpiperidin-4-yl)pyrimidin-5-yl)pyrido[3,2-d]pyrimidin-4-yl)amino)-2-methylhexan-1-ol 8

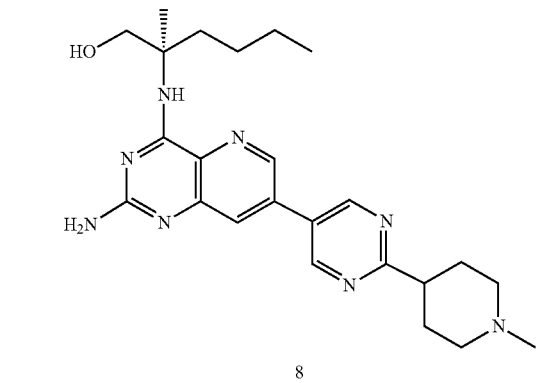

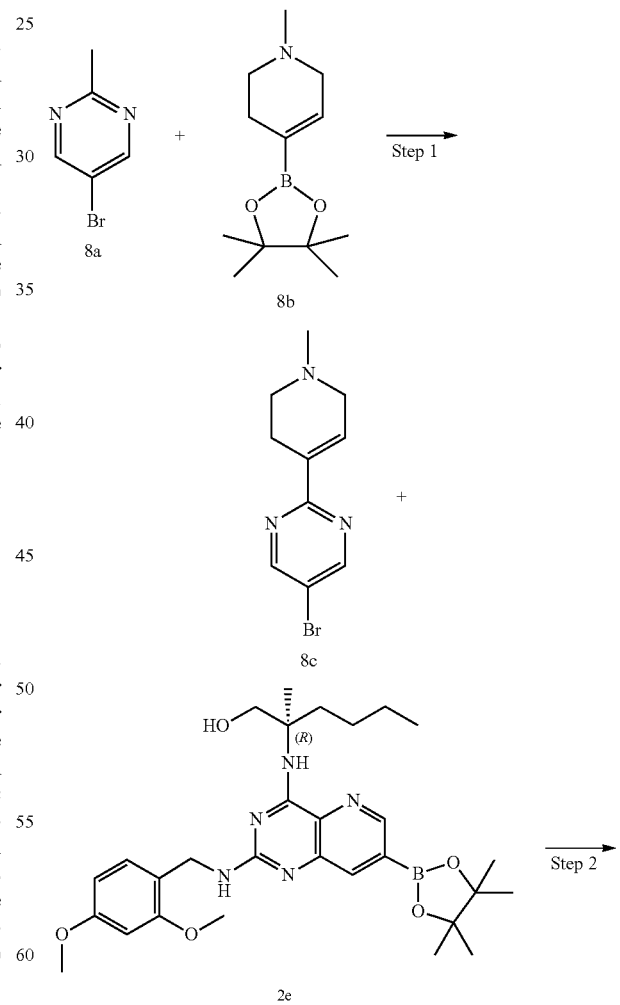

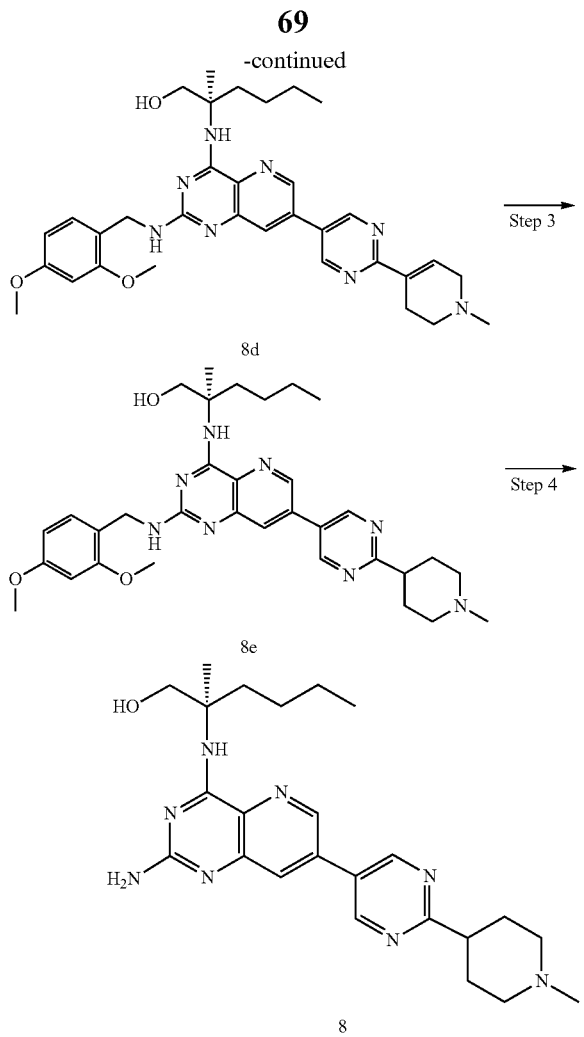

Step 1

5-Bromo-2-(1-methyl-1,2,3,6-tetrahydropyridin-4-yl)pyrimidine 8c

Compound 5-bromo-2-iodopyrimidine 8a (4 g, 14.041 mmol) was added to 200 mL of 1,4-dioxane and 40 mL of water, followed by the addition of 1-methyl-4-(4,4,5,5-tetramethyl-1,3,2-dioxaborolan-2-yl)-1,2,3,6-tetrahydropyridine 8b (3.45 g, 15.463 mmol), 1,1'-bisdiphenylphosphinoferrocene palladium dichloride (1.05 g, 1.435 mmol) and potassium carbonate (3.89 g, 28.146 mmol). The reaction solution was purged with argon three times, warmed to 45° C. and stirred overnight. The reaction solution was concentrated under reduced pressure. 30 ml of water was added to the reaction system, which was then extracted with dichloromethane (60 mL×3). The organic phases were combined, washed with water (30 mL) and saturated sodium chloride solution (30 mL) respectively, dried over anhydrous magnesium sulfate, and filtered to remove the desiccant. The filtrate was concentrated under reduced pressure. The residues were purified by silica gel column chromatography with eluent system B to obtain the title product 8c (2.5 g, yield: 70.1%).

MS m/z (ESI): 255.9 [M+1].

Step 2

(R)-2-((2-((2,4-Dimethoxybenzyl)amino)-7-(2-(1-methyl-1,2,3,6-tetrahydropyridin-4-yl)pyrimidin-5-yl)pyrido[3,2-d]pyrimidin-4-yl)amino)-2-methyl-hexan-1-ol 8d Compound 2e (4.15 g, 7.5252 mmol) was added to 80 mL of 1,4-dioxane and 16 mL of water, followed by the addition of compound 8c (1.53 g, 6.021 mmol), 1,1'-bisdiphenylphosphinoferrocene palladium dichloride (551 mg, 0.753 mmol) and potassium carbonate (2.1 g, 15.195 mmol). The reaction solution was purged with argon three times, heated to 95° C. and stirred for 45 minutes. The reaction solution was concentrated under reduced pressure. 40 ml of water was added to the reaction system, which was then extracted with dichloromethane (40 mL×3). The organic phases were combined, washed with water (40 mL) and saturated sodium chloride solution (40 mL) respectively, dried over anhydrous magnesium sulfate, and filtered to remove the desiccant. The filtrate was concentrated under reduced pressure. The residues were purified by silica gel column chromatography with eluent system B to obtain the title product 8d (3.5 g, yield: 77.7%).

MS m/z (ESI): 599.4[M+1].

Step 3

(R)-2-((2-((2,4-Dimethoxy benzyl)amino)-7-(2-(1-methylpiperidin-4-yl)pyrimidin-5-yl)pyrido[3,2-d]pyrimidin-4-yl)amino)-2-methylhexan-1-ol 8e Compound 8d (3.5 g, 5.846 mmol) was added to 50 mL of methanol, followed by the addition of Pd/C (1 g). The reaction solution was purged with hydrogen five times, and reacted at room temperature for 48 hours. Pd/C was removed by filtration, and the filtrate was concentrated under reduced pressure. The residues were purified by silica gel column chromatography with eluent system B to obtain the title product 8e (1.7 g, yield: 48.4%).

MS m/z (ESI): 601.4 [M+1].

Step 4

(R)-2-((2-Amino-7-(2-(1-methylpiperidin-4-yl)pyrimidin-5-yl)pyrido[3,2-d]pyrimidin-4-yl)amino)-2-methylhexan-1-ol 8

The crude compound 8e (1.7 g. 2.830 mmol) was added to 20 mL of trifluoroacetic acid, and reacted at room temperature for 1 hour. The reaction solution was concentrated under reduced pressure. 50 ml of saturated sodium carbonate solution was added to the reaction solution, which was then extracted with dichloromethane (50 mL×3). The organic phases were combined, washed with saturated sodium chloride solution (50 mL), dried over anhydrous magnesium sulfate, and filtered to remove the desiccant. The filtrate was concentrated under reduced pressure. The residues were purified by high performance liquid chromatography (Waters-2767, elution system: $H_2O$ (10 mmol $NH_4OAc$), ACN) to obtain the product 8 (600 mg, yield: 47.1%).

MS m/z (ESI): 451.3 [M+1].

$^1$H NMR (400 MHZ, DMSO-$d_6$) δ 9.16 (s, 2H), 8.64 (s, 1H), 7.90 (s, 1H), 7.22 (s, 1H), 6.37 (br, 2H), 5.14-5.12 (m, 1H), 3.71-3.67 (m, 1H), 3.51-3.47 (m, 1H), 2.89-2.72 (m, 3H), 2.17 (s, 3H), 2.05-1.72 (m, 8H), 1.40 (s, 3H), 1.28-1.19 (m, 4H), 0.83 (t, 3H).

Example 9

2-((2-Amino-7-(6-(piperazin-1-ylmethyl)pyridin-3-yl)pyrido[3,2-d]pyrimidin-4-yl)amino)-2-methyl-hexan-1-ol 9

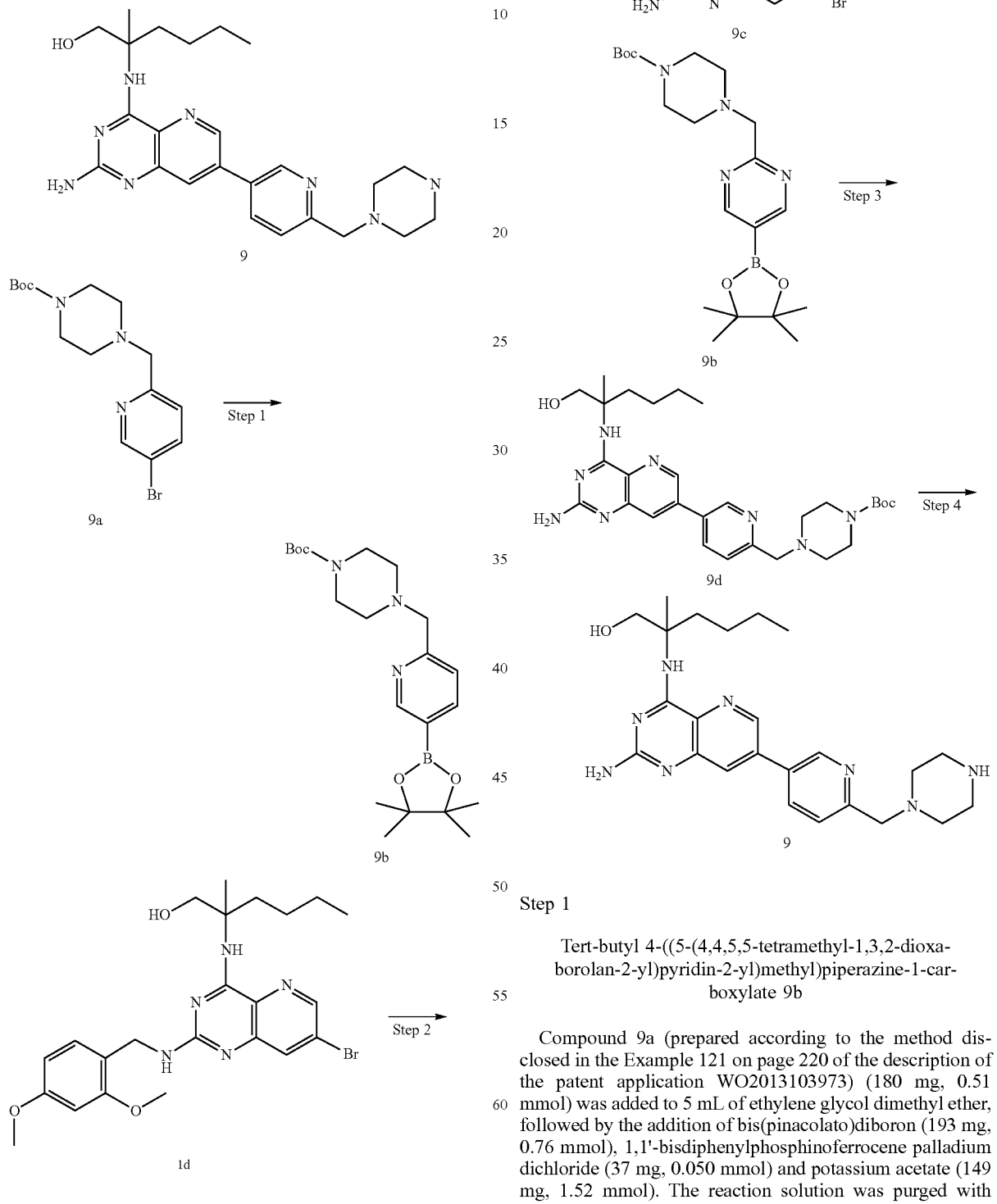

Step 1

Tert-butyl 4-((5-(4,4,5,5-tetramethyl-1,3,2-dioxaborolan-2-yl)pyridin-2-yl)methyl)piperazine-1-carboxylate 9b Compound 9a (prepared according to the method disclosed in the Example 121 on page 220 of the description of the patent application WO2013103973) (180 mg, 0.51 mmol) was added to 5 mL of ethylene glycol dimethyl ether, followed by the addition of bis(pinacolato)diboron (193 mg, 0.76 mmol), 1,1'-bisdiphenylphosphinoferrocene palladium dichloride (37 mg, 0.050 mmol) and potassium acetate (149 mg, 1.52 mmol). The reaction solution was purged with argon three times, heated to 80° C. and stirred for 2 hours. The reaction solution was concentrated under reduced pressure. 20 ml of water was added to the reaction system, which was then extracted with dichloromethane (10 mL×3). The organic phases were combined, washed with water (20 mL) and saturated sodium chloride solution (20 mL) respectively, dried over anhydrous magnesium sulfate, and filtered to remove the desiccant. The filtrate was concentrated under reduced pressure to obtain the crude title product 9b (203 mg, yield: 100%), which was used directly in the next step without purification.

MS m/z (ESI): 404.2 [M+1].

Step 2

2-((2-Amino-7-bromopyrido[3,2-d]pyrimidin-4-yl)amino)-2-methylhexan-1-ol 9c

Compound 1d (1.0 g, 1.98 mmol) was added to 15 mL of trifluoroacetic acid, and reacted at room temperature for 1 hour. The reaction solution was concentrated under reduced pressure. 20 ml of saturated sodium bicarbonate solution was added to the reaction solution, which was then extracted with dichloromethane (20 mL×3). The organic phases were combined, washed with saturated sodium chloride solution (30 mL), dried over anhydrous magnesium sulfate, and filtered to remove the desiccant. The filtrate was concentrated under reduced pressure. The residues were purified by high performance liquid chromatography (Waters-2767, elution system: $H_2O$ (10 mmol $NH_4OAc$), ACN) to obtain the product 9c (402 mg, yield: 58.0%).

Step 3

Tert-butyl 4-((5-(2-amino-4-((1-hydroxy-2-methylhexan-2-yl)amino)pyrido[3,2-d]pyrimidin-7-yl)pyridin-2-yl)methyl)piperazine-1-carboxylate 9d Compound 9c (193 mg, 0.546 mmol) was added to 10 mL of 1,4-dioxane and 2 mL of water, followed by the addition of the crude compound 9b (200 mg, 0.50 mmol), 1,1'-bisdiphenylphosphinoferrocene palladium dichloride (37 mg, 0.050 mmol) and potassium carbonate (138 mg, 1.00 mmol). The reaction solution was purged with argon three times, heated to 80° C. and stirred for 2 hours. The reaction solution was concentrated under reduced pressure. 20 ml of water was added to the reaction system, which was then extracted with dichloromethane (10 mL×3). The organic phases were combined. The organic phase was washed with water (20 mL) and saturated sodium chloride solution (30 mL) respectively, dried over anhydrous magnesium sulfate, and filtered to remove the desiccant. The filtrate was concentrated under reduced pressure. The residues were purified by silica gel column chromatography with eluent system B to obtain the title product 9d (125 mg, yield: 45.9%).

MS m/z (ESI): 551.3 [M+1].

Step 4

2-((2-Amino-7-(6-(piperazin-1-ylmethyl)pyridin-3-yl)pyrido[3,2-d]pyrimidin-4-yl)amino)-2-methylhexan-1-ol 9

Compound 9d (100 mg, 0.181 mmol) was added to 5 mL of trifluoroacetic acid, and reacted at room temperature for 1 hour. The reaction solution was concentrated under reduced pressure. 50 ml of saturated sodium carbonate solution was added to the reaction solution, which was then extracted with dichloromethane (50 mL×3). The organic phases were combined, washed with saturated sodium chloride solution (50 mL), dried over anhydrous magnesium sulfate, and filtered to remove the desiccant. The filtrate was concentrated under reduced pressure. The residues were purified by high performance liquid chromatography (Waters-2767, elution system: $H_2O$ (10 mmol $NH_4OAc$), ACN) to obtain the product 9 (30 mg, yield: 36.7%).

MS m/z (ESI): 451.2 [M+1].

$^1$H NMR (400 MHZ, DMSO-$d_6$) δ 8.88 (s, 1H), 8.60 (s, 1H), 8.14-8.17 (m, 1H), 7.79 (s, 1H), 7.21 (s, 1H), 6.37 (br, 3H), 3.67-3.71 (m, 1H), 3.71-3.67 (m, 1H), 3.60 (s, 2H), 3.48-3.50 (m, 1H), 2.71-2.74 (m, 3H), 2.30-2.35 (m, 4H), 1.90-1.92 (m, 2H), 1.40 (s, 3H), 1.21-1.24 (m, 6H), 0.81-0.84 (t, 3H).

TEST EXAMPLES

Biological Assay

Test Example 1. Determination of Agonist Activity of the Compounds of the Present Invention on Human TLR8 and TLR7

The agonist effect of the compounds of the present invention on hTLR8 expressed by the HEK-Blue™ hTLR8 stably transfected cells was determined by the following experimental method.

I. Experimental Materials and Instruments
 1. DMEM(Gibco, 10564-029);
 2. Fetal bovine serum (GIBCO, 10099);
 3. Trypan blue solution (Sigma, T8154-100 ML);
 4. Flexstation 3 multi-function microplate reader (Molecular Devices);
 5. HEK-Blue™ hTLR8 cell line (InvivoGen, hkb-hTLR8), or HEK-Blue™ hTLR7 cell line (InvivoGen, hkb-hTLR7);
 6. HEK-Blue detection reagent (InvivoGen, hb-det3); and
 7. Phosphate buffer solution (PBS) pH 7.4 (Shanghai Basalmedia Technologies Co., Ltd., B320).

II. Experimental Procedures a. Determination of Agonist Activity on Human TLR8

A bag of HEK-Blue detection dry powder was dissolved in 50 ml of water free of endotoxin, and the solution was then placed in an incubator at 37° C. for 10 minutes followed by sterile filtration to prepare a HEK-Blue detection medium. The compound was firstly formulated into a 20 mM stock solution, then diluted with pure DMSO to a maximum concentration of 6×10$^6$ nM, and a total of 10 points were obtained by a 3-fold gradient dilution. The above formulated compound was firstly diluted 20-fold with the medium, then 20 μl of the diluted compound was added to each well.

The supernate was removed from the HEK-Blue™ hTLR8 cells, to which 2-5 ml of pre-warmed PBS was then added. The cells were placed in an incubator for 1-2 minutes, gently pipetted, and counted by trypan blue staining. The cells were re-suspended in the HEK-Blue detection medium to adjust the concentration to 2.2×10$^5$ cells/ml. 180 μl of cells was added to the above 96-well plate comprising 20 μl of the compound, and incubated at 37° C. for 16 hours.

The corresponding OD values were obtained by a microplate reader at a wavelength of 620 nm, and the $EC_{50}$ values of the compounds were calculated by Graphpad Prism.

b. Determination of Agonist Activity on Human TLR7

A bag of HEK-Blue detection dry powder was dissolved in 50 ml of water free of endotoxin, and the solution was then placed in an incubator at 37° C. for 10 minutes followed by sterile filtration to prepare a HEK-Blue detection medium. The compound was firstly formulated into a 20 mM stock solution, then diluted with pure DMSO to a maximum concentration of 6×10$^6$ nM, and a total of 10 points were obtained by a 3-fold gradient dilution. The above formulated compound was firstly diluted 20-fold with the medium, then 20 μl of the diluted compound was added to each well.

The supernate was removed from the HEK-Blue™ hTLR7 cells, to which 2-5 ml of pre-warmed PBS was then added. The cells were placed in an incubator for 1-2 minutes, gently pipetted, and counted by trypan blue staining. The cells were re-suspended in the HEK-Blue detection medium to adjust the concentration to $2.2×10^5$ cells/ml. 180 μl of cells was added to the above 96-well plate comprising 20 μl of the compound, and incubated at 37° C. for 16 hours.

The corresponding OD values were obtained by a microplate reader at a wavelength of 620 nm, and the $EC_{50}$ values of the compounds were calculated by Graphpad Prism.

The agonist effect of the compounds of the present invention on human TLR8 and TLR7 can be determined by the above test, and the obtained $EC_{50}$ values are shown in Table 1.

TABLE 1

$EC_{50}$ bvalues of the compounds of the present invention on human TLR8 and TLR7

| Example No. | TLR8 $EC_{50}$ (μM) | TLR8 Emax (%) | TLR7 $EC_{50}$ (μM) | TLR7 Emax (%) |
|---|---|---|---|---|
| 1 | 0.13 | 97 | — | — |
| 2 | 0.08 | 106 | — | — |
| 3 | 0.10 | 104 | — | — |
| 4 | 0.10 | 97 | >30 | 12 |
| 5 | 0.27 | 110 | >30 | 14 |
| 6 | 0.10 | 107 | >30 | 14 |
| 7 | 0.08 | 116 | — | — |
| 8 | 0.04 | 114 | >19 | 73 |
| 9 | 0.15 | 103 | >30 | 5 |

"—" means not tested.

Conclusion: The compounds of the present invention have a good activating effect on human TLR8, while have no activating effect on human TLR7, indicating that the compounds of the present invention are selective for TLR8.

Test Example 2. Inhibition Effect of the Compounds of the Present Invention on the Enzyme Activity of Midazolam Metabolite Site of CYP3A4 in Human Liver Microsome The effect of the compounds of the present invention on the enzyme activity of midazolam metabolite site of CYP3A4 in human liver microsomes was determined by the following experimental method.

I. Experimental Materials and Instruments
1. Phosphate buffer solution (PBS) (Shanghai Basalmedia Technologies Co., Ltd., B320, similarly hereinafter);
2. NADPH (Sigma N-1630);
3. Human liver microsome (Corning Gentest);
4. ABI QTrap 4000 liquid chromatograph/mass spectrometer (AB Sciex);
5. Inertsil C8-3 column, 4.6×50 mm, 5 μm (Dikma Technologies Inc., USA); and
6. CYP probe substrate (15 μM midazolam, SIGMA UC429) and positive control inhibitor (ketoconazole, SIGMA K1003).

II. Experimental Procedures 100 mM PBS buffer was formulated, which was then used to formulate 2.5 mg/ml human microsome solution and 5 mM NADPH solution. The 5× concentration of the compound working solution was diluted with PBS in gradients (150, 50, 15, 5, 1.5, 0.15, 0.015, 0 μM). The 5× concentration of ketoconazole working solution was diluted with PBS in gradients (150, 50, 15, 5, 1.5, 0.15, 0.015, 0 μM). Midazolam working solution was diluted with PBS to a concentration of 15 μM.

20 μl of 2.5 mg/ml microsome solution, 20 μl of 15 μM midazolam working solution, 20 μl of $MgCl_2$ solution and 20 μl of the compound working solution (150, 50, 15, 5, 1.5, 0.15, 0.015, 0 μM, different reaction systems for each concentration) were mixed well. For the positive control group, the compound was replaced with the same concentration of ketoconazole. The mixture together with 5 mM NADPH solution was pre-incubated at 37° C. for 5 minutes. After 5 minutes, 20 μl of NADPH was added to each well, the reaction was initiated, and the plate was incubated for 30 minutes. All the incubated samples were present in duplicate. After 30 minutes, 250 μl of acetonitrile containing internal standard (100 ng/ml camptothecin) was added to all samples, mixed well, shaken at 800 rpm for 10 minutes, and then centrifuged at 3700 rpm for 10 minutes. 80 μl of the supernatant was taken and analyzed by LC-MS/MS.

The data was calculated by Graphpad Prism to obtain the $IC_{50}$ values of the compounds on the midazolam metabolite site of CYP3A4, which are shown in Table 2.

TABLE 2

$IC_{50}$ values of the compounds of the present invention on the midazolam metabolite site of CYP3A4

| Example No. | $IC_{50}$ (μM) |
|---|---|
| 2 | 27 |
| 4 | >30 |
| 5 | >30 |
| 6 | >30 |
| 8 | >30 |

Conclusion: The compounds of the present invention have no inhibition effect on the midazolam metabolic site of CYP3A4 in human liver microsome, and show good safety, indicating that the metabolic drug interaction based on the midazolam metabolic site of CYP3A4 will not occur.

Test Example 3. Inhibition Effect of the Compounds of the Present Invention on the Enzyme Activity of CYP2D6 in Human Liver Microsome The effect of the compounds of the present invention on the enzyme activity of CYP2D6 in human liver microsome was determined by the following experimental method.

I. Experimental Materials and Instruments
1. Phosphate buffer solution (PBS);
2. NADPH (Sigma N-1630);
3. Human liver microsome (Corning Gentest);
4. ABI QTrap 4000 liquid chromatograph/mass spectrometer (AB Sciex);
5. Inertsil C8-3 column, 4.6×50 mm, 5 μm (Dikma Technologies Inc., USA); and
6. CYP probe substrate (20 μM dextromethorphan, SIGMA Q0750) and positive control inhibitor (quinidine, SIGMA D9684).

II. Experimental Procedures 100 mM PBS buffer was formulated, which was then used to formulate 2.5 mg/ml human microsome solution and 5 mM NADPH solution. The 5× concentration of the compound working solution was diluted with PBS in gradients (150, 50, 15, 5, 1.5, 0.15, 0.015, 0 μM). The 5× concentration of quinidine working solution was diluted with PBS in gradients (150, 50, 15, 5, 1.5, 0.15, 0.015, 0 μM). Dextromethorphan working solution was diluted with PBS to a concentration of 20 μM.

20 μl of 2.5 mg/ml microsome solution, 20 μl of 20 μM dextromethorphan working solution, 20 μl of MgCl$_2$ solution and 20 μl of the compound working solution (150, 50, 15, 5, 1.5, 0.15, 0.015, 0 μM, different reaction systems for each concentration) were mixed well. For the positive control group, the compound was replaced with the same concentration of quinidine. The mixture together with 5 mM NADPH solution was pre-incubated at 37° C. for 5 minutes. After 5 minutes, 20 μl of NADPH was added to each well, the reaction was initiated, and the plate was incubated for 30 minutes. All the incubated samples were present in duplicate. After 30 minutes, 250 μl of acetonitrile containing internal standard (100 ng/ml camptothecin) was added to all samples, mixed well, shaken at 800 rpm for 10 minutes, and then centrifuged at 3700 rpm for 10 minutes. 80 μl of the supernatant was taken and analyzed by LC-MS/MS.

The data was calculated by Graphpad Prism to obtain the IC$_{50}$ values of the inhibition effect of the present compounds on CYP2D6 enzyme, which are shown in Table 3.

TABLE 3

| IC$_{50}$ values of the inhibition effect of the present compounds on CYP2D6 enzyme | |
|---|---|
| Example No. | IC$_{50}$ (μM) |
| 2 | >30 |
| 4 | >30 |
| 5 | >30 |
| 6 | >30 |
| 8 | >30 |

Conclusion: The compounds of the present invention have a poor inhibition effect on the enzyme activity of CYP2D6 in human liver microsome, and show good safety, indicating that the metabolic drug interaction based on the CYP2D6 will not occur.

Test Example 4. Inhibition Effect of the Compounds of the Present Invention on the Enzyme Activity of Testosterone Metabolite Site of CYP3A4 in Human Liver Microsomes The effect of the compounds of the present invention on the enzyme activity of testosterone metabolite site of CYP3A4 in human liver microsomes was determined by the following experimental method.

I. Experimental Materials and Instruments
1. Phosphate buffer solution (PBS);
2. NADPH (Sigma N-1630);
3. Human liver microsome (Corning Gentest);
4. ABI QTrap 4000 liquid chromatograph/mass spectrometer (AB Sciex);
5. Inertsil C8-3 column, 4.6×50 mm, 5 μm (Dikma Technologies Inc., USA); and
6. CYP probe substrate (testosterone/100 μM, SIGMA K1003) and positive control inhibitor (ketoconazole, Dr. Ehrenstorfer GmbH, C17322500).

II. Experimental Procedures
100 mM PBS buffer was formulated, which was then used to formulate 2.5 mg/ml human microsome solution and 5 mM NADPH solution. The 5× concentration of the compound working solution was diluted with PBS in gradients (150, 50, 15, 5, 1.5, 0.15, 0.015, 0 μM). The 5× concentration of ketoconazole working solution was diluted with PBS in gradients (150, 50, 15, 5, 1.5, 0.15, 0.015, 0 μM). Dextromethorphan working solution was diluted with PBS to a concentration of 50 μM.

20 μl of 2.5 mg/ml microsome solution, 20 μl of 50 μM testosterone working solution, 20 μl of MgCl$_2$ solution and 20 μl of the compound working solution (150, 50, 15, 5, 1.5, 0.15, 0.015, 0 μM, different reaction systems for each concentration) were mixed well. For the positive control group, the compound was replaced with the same concentration of ketoconazole. The mixture together with 5 mM NADPH solution was pre-incubated at 37° C. for 5 minutes. After 5 minutes, 20 μl of NADPH was added to each well, the reaction was initiated, and the plate was incubated for 30 minutes. All the incubated samples were present in duplicate. After 30 minutes, 250 μl of acetonitrile containing internal standard (100 ng/ml camptothecin) was added to all samples, mixed well, shaken at 800 rpm for 10 minutes, and then centrifuged at 3700 rpm for 10 minutes. 80 μl of the supernatant was taken and analyzed by LC-MS/MS.

The data was calculated by Graphpad Prism to obtain the IC$_{50}$ values of the compounds on the testosterone metabolite site of CYP3A4, which are shown in Table 4.

TABLE 4

| IC$_{50}$ values of the compounds of the present invention on the testosterone metabolite site of CYP3A4 | |
|---|---|
| Example No. | IC$_{50}$ (μM) |
| 4 | 16 |
| 5 | 8.3 |
| 6 | >30 |
| 8 | >30 |

Conclusion: The compounds of the present invention have no inhibition effect on the testosterone metabolite site of CYP3A4 in human liver microsome, and show good safety, indicating that the metabolic drug interaction based on the testosterone metabolite site of CYP3A4 will not occur.

Test Example 5. Determination of the Stimulating Effect of the Compounds of the Present Invention on the Ability of Secretion of IL12 and IFN γ from Peripheral Blood Mononuclear Cells (PBMC)

The stimulating effect of the compounds of the present invention on the ability of secretion of IL12 and IFN γ from PBMC was determined by the following experimental method.

I. Experimental Materials and Instruments
1. RMPI 1640 (Invitrogen, 11875);
2. FBS (Gibco, 10099-141);
3. Ficoll-Paque PREMIUM (GE, 17-5442-02);
4. Trypan blue solution (Sigma, T8154-100 ML);
5. SepMate™-50 (Stemcell, 15460);
6. Bright-LineIM blood cell counter (Sigma, Z359629-1EA);
7. 96-well cell culture plate (Corning, 3599);
8. 96-well v-bottom plate (Corning, 3894);
9. Human IL-12 ELISA kit (Neobioscience Technology Co., EHC152.96);
10. Human IFN γ kit (cisbio, 62HIFNGPEG); and 11. PHERAStar multi-function microplate reader (BMG, PHERAStar).

II. Experimental Procedures

The compound was diluted with pure DMSO to a maximum concentration of 5 mM, and a total of 9 points were obtained by a 4-fold gradient dilution. 4 µl of the compound solution was then added to 196 µl of RMPI 1640 medium containing 10% FBS and mixed well. 50 µl of the mixture was taken and added to a 96-well cell culture plate.

All reagents were equilibrated to room temperature. 60 ml of blood from a healthy human and the same volume of PBS (containing 2% FBS) were added to a 250 ml culture flask, gently pipetted, mixed well and diluted. 15 ml of lymphocyte separation solution Ficoll-Paque PREMIUM was added to a 50 ml PBMC centrifuge tube SepMate™-50, followed by the addition of 30 ml of the above diluted blood. The mixture was centrifuged at 1200 g for 10 minutes at room temperature. The supernatant was taken and then centrifuged at 300 g for 8 minutes. The cells were re-suspended in the RMPI 1640 medium containing 10% FBS and counted, and the number of PBMCs was adjusted to $3.33 \times 10^6$ cells/ml. 150 µl of the cell solution was added to the plate containing the compounds, and incubated in an incubator at 37° C., 5.0% $CO_2$ for 24 hours. The cell culture plate was placed in a centrifuge, and centrifuged at 1200 rpm for 10 minutes at room temperature. 150 µl of the supernatant was taken from each well.

The reagents in the Human IL-12 ELISA kit were equilibrated to room temperature. According to the kit's instruction, the highest concentration of the standard is 2000 pg/ml, and a total of 8 points were obtained by a 2-fold gradient dilution. The sample to be tested was diluted 20 folds. The solution was then added to a pre-coated plate at 100 µl/well. The plate was incubated at 37° C. for 90 minutes and rinsed. The antibiotic-antibody was added at 100 µl/well, and the plate was incubated at 37° C. for 60 minutes and rinsed. HRP binding enzyme was added at 100 µl/well, and the plate was incubated at 37° C. for 30 minutes and rinsed. TMB was added, and the plate was incubated at room temperature for 5 minutes. Finally, the stop solution was added to stop the reaction, and the absorbance at 450 nm was read by the microplate reader.

The reagents in the Human IFN γ test kit were equilibrated to room temperature. The standard and detection antibody were prepared according to the kit's instruction under dark conditions. 16 µl of the supernatant obtained by centrifugation was added to each well, and 4 µl of freshly prepared mixed detection antibody was added to each well. The solution was mixed well by shaking, and incubated overnight in the dark at room temperature. The plate was read by the PHERAStar multi-function microplate reader.

The concentration of the compound that can stimulate PBMC to produce SD that is 3 times higher than the average value of the group without the compound (SD of the group without the compound) was defined as the minimum effective concentration (MEC) value of the compound.

The stimulation effect of the compounds of the present invention on the ability of secrete IL12 and IFNγ from PBMC was determined by the above test, and the obtained MEC values are shown in Table 5.

TABLE 5

MEC of the compounds of the present invention on stimulating PBMC to secrete IL12 and IFNγ

| Example No. | IL12 MEC (nM) | IFNγ MEC (nM) |
|---|---|---|
| 2 | 23 | 24 |
| 3 | 15 | 27 |
| 4 | 31 | 33 |
| 6 | 41 | — |
| 8 | 5 | — |
| 9 | 24 | 94 |

"—" means not tested.

Conclusion: From the activity data of the compounds of the present invention on stimulating PBMC to secrete IL12 and IFNγ, the compounds of the present invention have the advantage of a lower effective concentration.

Test Example 6. Determination of the Inhibition Effect of the Compounds on hERG Potassium Channel by Patchliner 1. The Purpose of the Experiment The blocking effect of the compounds of the present application on hERG potassium current was determined using an automatic patch-clamp on a stable cell line transfected with hERG potassium channels.

2. Experimental Method 2.1 Experimental Materials and Instruments 2.1.1 Experimental Materials:

| Reagent name | Supply company | Item No. |
|---|---|---|
| FBS | GIBCO | 10099 |
| Sodium pyruvate solution | sigma | S8636-100ML |
| MEM non-essential amino acid solution (100×) | sigma | M7145-100ML |
| G418 sulfate | Enzo | ALX-380-013-G005 |
| MEM | Hyclone | SH30024.01B |
| hERG cDNA | Origene | — |
| G418.Sulfate | Enzo | ALX-380-013-G005 |
| pcDNA3.1(+) | invitrogen | V79020 |
| HEK293 human embryonic kidney cells | Chinese Academy of Sciences Cell Bank | Art. No. GNHu18 |

2.1.2 Experimental Instruments

| Instrument name | Supply company | Mode |
|---|---|---|
| Patchliner 4 channel | nanion | 2-03-03100-002 |
| Patchliner cleaning station | nanion | 2-02-03201-005 |
| Patchliner cell bank | nanion | 2-02-03105-000 |
| Elektrodenchloridierer Patchliner | nanion | 3-02-03533-000 |
| HEAK EPC10 patch clamp amplifier | nanion | 1-01-10012-000 |
| Osmotic pressure molar tester | Gonoter | Gonoter 030 |
| pH meter | Mettle Toledo | FE20 |

2.2 Automatic Patch Clamp Experimental Procedures

The HEK293 cell line was transfected with pCDNA3.1(+) that had constructed the hERG gene. The monoclonal HEK293-hERG stable cell line was screened by adding G418. The HEK293-hERG stable cell line was subcultured at a density of 1:4 in MEM/EBSS medium (10% FBS, 400 µg/mL G418, 1% MEM non-essential amino acid solution (100×), 1% sodium pyruvate solution) and cultured within 48 to 72 hours for the automatic patch clamp experiment. On the day of the experiment, the cells were digested with 0.25% trypsin (life technologies, 12563-029), collected by centrifugation and resuspended with extracellular fluid (140 mM NaCl, 4 mM KCl, 1 mM $MgCl_2$, 2 mM $CaCl_2$, 5 mM MD glucose monohydrate, 10 mM HEPES, pH 7.4, 298 mOsmol) to obtain a cell suspension. The cell suspension was placed on the cell bank of the Patchliner instrument, the Patchliner instrument used a negative pressure controller to apply the cells to the chip (NPC-16), and the negative pressure attracted individual cells to the wells of the chip. When the whole cell mode was formed, the instrument got the hERG current according to the set hERG current-voltage program, and then the instrument automatically perfused the compound from low to high concentration. The currents at each concentration of the compound and the blank control current were analyzed by the HEAK EPC 10 patch clamp amplifier (Nanion), Pathlinersoftware and data analysis software provided by Pathcontrol HTsoftware.

2.3 Experimental Results

The blocking effect of the compounds of the present invention on hERG potassium current was determined by the above test, and the obtained $IC_{50}$ values are shown in Table 6.

TABLE 6

| $IC_{50}$ of the blocking effect of the compounds of the present invention on hERG potassium current | |
|---|---|
| Example No. | $IC_{50}$ (μM) |
| 2 | 7 |
| 4 | 14 |
| 5 | 17 |
| 6 | 26 |
| 8 | >30 |

Conclusion: The compounds of the present application have a weak inhibitory effect on hERG, and could reduce side effects caused by the hERG pathway.

What is claimed is:

1. A compound of formula (I);

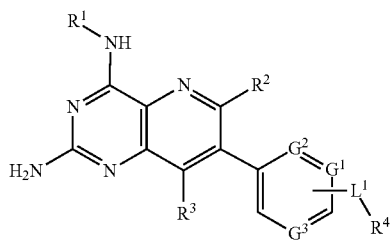

(I)

or a tautomer, mesomer, racemate, enantiomer, diastereomer thereof, or mixture thereof, or a pharmaceutically acceptable salt thereof,
wherein:
$G^1$ is N;
$G^2$ is $CR^5$;
$G^3$ is $CR^5$ or N;
$L^1$ is selected from the group consisting of alkylene and covalent bond;
$R^1$ is alkyl, wherein the alkyl is optionally substituted by one or more hydroxy;
$R^2$ and $R^3$ are identical or different, and are each independently selected from the group consisting of hydrogen atom, halogen, alkyl, alkoxy, haloalkyl, haloalkoxy, hydroxy, hydroxyalkyl, cyano, amino, nitro, cycloalkyl, heterocyclyl, aryl and heteroaryl;
$R^4$ is heterocyclyl, wherein the heterocyclyl is optionally substituted by one or more substituent(s) selected from the group consisting of alkyl, alkoxy, halogen, amino, cyano, nitro, hydroxy, hydroxyalkyl, cycloalkyl, heterocyclyl, aryl and heteroaryl; and
$R^5$ is selected from the group consisting of hydrogen atom, halogen, alkyl, alkoxy, haloalkyl, haloalkoxy, hydroxy, hydroxyalkyl, cyano, amino, nitro, cycloalkyl, heterocyclyl, aryl and heteroaryl.

2. The compound of formula (I) according to claim 1, which is a compound of formula (Ia):

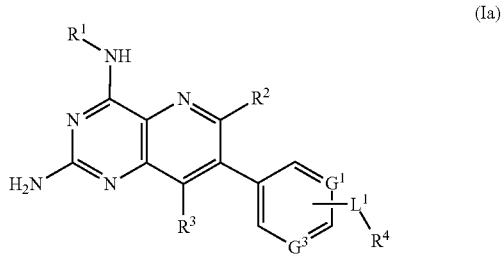

(Ia)

or a tautomer, mesomer, racemate, enantiomer, diastereomer thereof, or mixture thereof, or a pharmaceutically acceptable salt thereof,
wherein:
$G^1$, $G^3$, $L^1$ and $R^1$ to $R^4$ are as defined in claim 1.

3. The compound of formula (I) according to claim 1, which is a compound of formula (II):

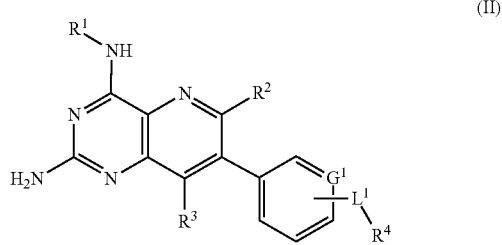

(II)

or a tautomer, mesomer, racemate, enantiomer, diastereomer thereof, or mixture thereof, or a pharmaceutically acceptable salt thereof,
wherein:
$G^1$, $L^1$ and $R^1$ to $R^4$ are as defined in claim 1.

4. The compound of formula (I) according to claim 1, which is a compound of formula (III):

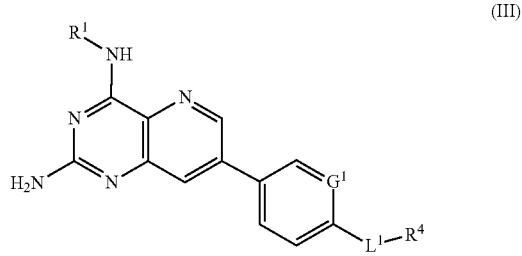

(III)

or a tautomer, mesomer, racemate, enantiomer, diastereomer thereof, or mixture thereof, or a pharmaceutically acceptable salt thereof,
wherein:
$G^1$, $L^1$, $R^1$ and $R^4$ are as defined in claim 1.

5. The compound of formula (I) according to claim 1, wherein $R^4$ is a heterocyclyl, which is optionally substituted by one or more alkyl(s); and/or $L^1$ is —(CH$_2$)$_n$— or a covalent bond; and n is an integer from 1 to 6.

6. The compound of formula (I) according to claim 1, which is a compound of formula (IV):

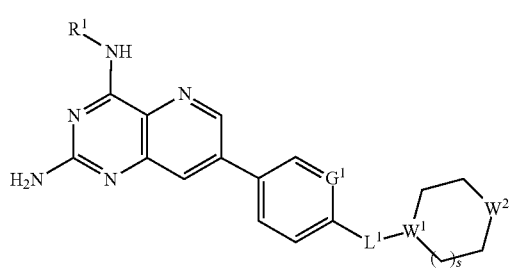

(IV)

or a tautomer, mesomer, racemate, enantiomer, diastereomer thereof, or mixture thereof, or a pharmaceutically acceptable salt thereof,
wherein:
$W^1$ is CH and $W^2$ is $NR^6$; or
$W^1$ is N and $W^2$ is CH$_2$ or $NR^6$;
$R^6$ is selected from the group consisting of hydrogen atom and alkyl;
s is 0 or 1; and
$G^1$, $L^1$ and $R^1$ are as defined in claim 1.

7. The compound of formula (I) according to claim 1, which is a compound of formula (V):

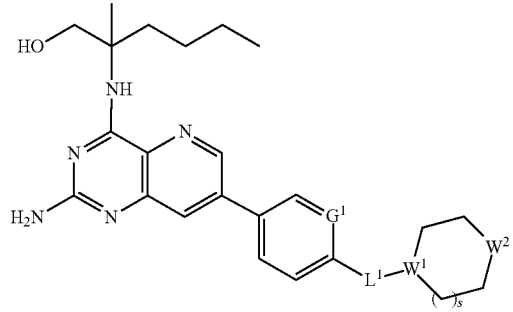

(V)

or a tautomer, mesomer, racemate, enantiomer, diastereomer thereof, or mixture thereof, or a pharmaceutically acceptable salt thereof,
wherein:
$W^1$ is CH and $W^2$ is $NR^6$; or
$W^1$ is N and $W^2$ is CH$_2$ or $NR^6$;
$R^6$ is selected from the group consisting of hydrogen atom and alkyl;
s is 0 or 1; and
$G^1$ and $L^1$ are as defined in claim 1.

8. The compound of formula (I) according to claim 1, which is selected from the group consisting of:

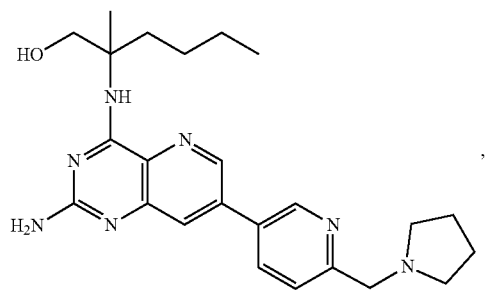

1

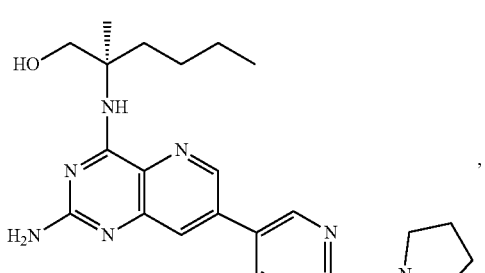

2

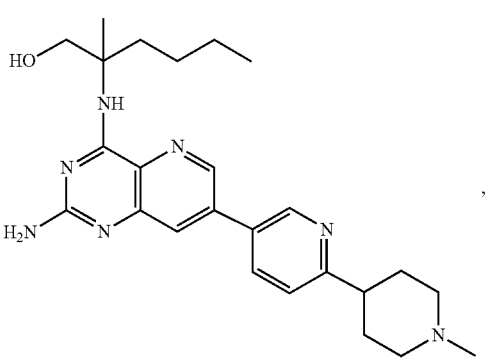

3

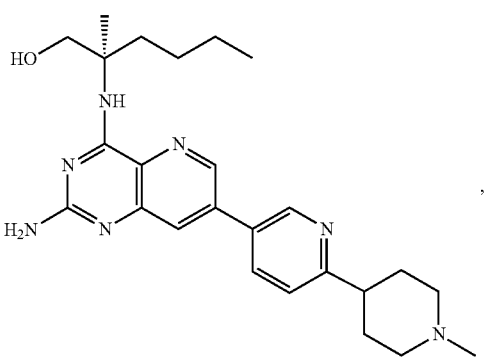

4

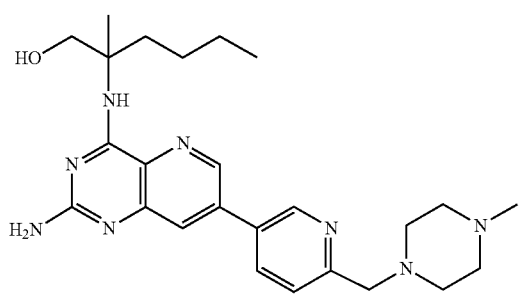

5

-continued

6

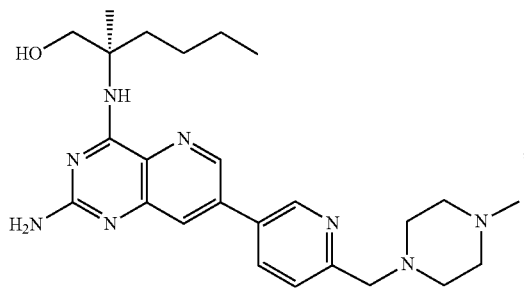

,

7

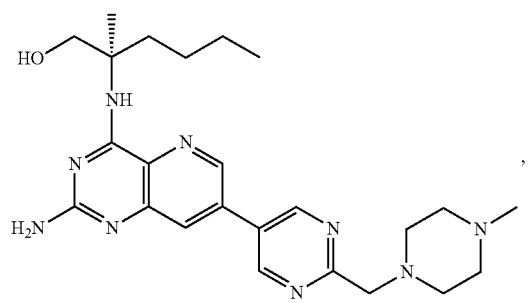

,

8

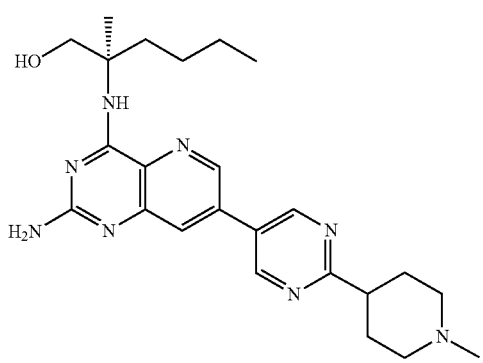

and

9

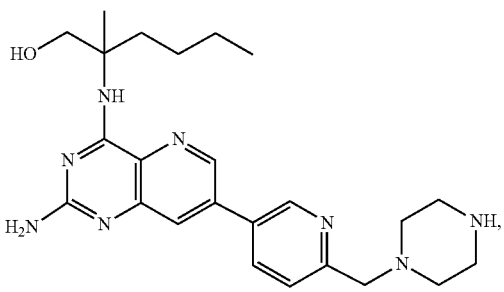

or a tautomer, mesomer, racemate, enantiomer, diastereomer thereof, or mixture thereof, or a pharmaceutically acceptable salt thereof.

9. A compound of formula (IA):

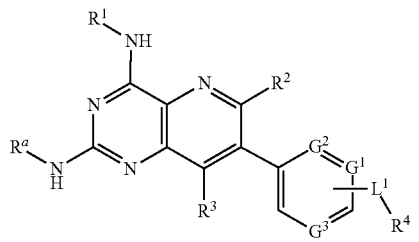

(IA)

or a tautomer, mesomer, racemate, enantiomer, diastereomer thereof, or mixture thereof, or a pharmaceutically acceptable salt thereof,
wherein:
$R^a$ is an amino protecting group;
$G^1$ is N;
$G^2$ is $CR^5$;
$G^3$ is $CR^5$ or N;
$L^1$ is selected from the group consisting of alkylene and covalent bond;
$R^1$ is alkyl, wherein the alkyl, is optionally substituted by one or more hydroxy;
$R^2$ and $R^3$ are identical or different, and are each independently selected from the group consisting of hydrogen atom, halogen, alkyl, alkoxy, haloalkyl, haloalkoxy, hydroxy, hydroxyalkyl, cyano, amino, nitro, cycloalkyl, heterocyclyl, aryl and heteroaryl;
$R^4$ is heterocyclyl, wherein the heterocyclyl is optionally substituted by one or more substituent(s) selected from the group consisting of alkyl, alkoxy, halogen, amino, cyano, nitro, hydroxy, hydroxyalkyl, cycloalkyl, heterocyclyl, aryl and heteroaryl; and
$R^5$ is selected from the group consisting of hydrogen atom, halogen, alkyl, alkoxy, haloalkyl, haloalkoxy, hydroxy, hydroxyalkyl, cyano, amino, nitro, cycloalkyl, heterocyclyl, aryl and heteroaryl.

10. A compound, which is selected from the group consisting of:

1g

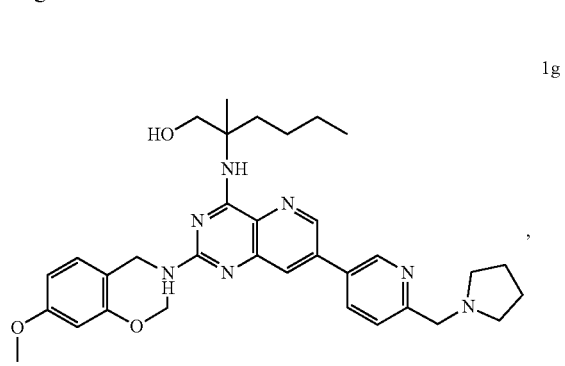

,

2g

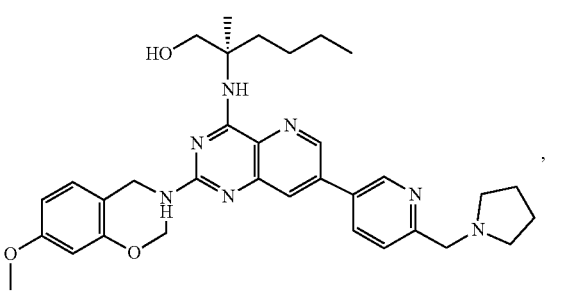

,

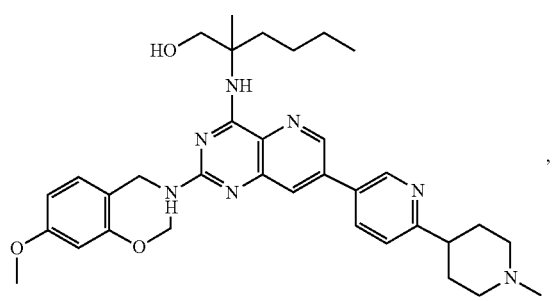
3c,

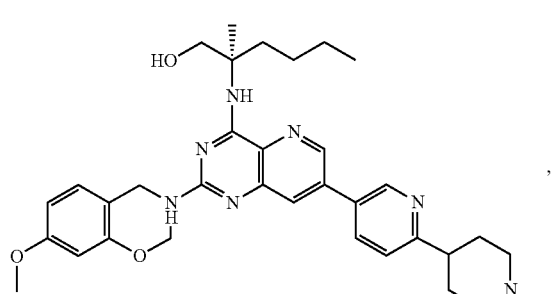
4c,

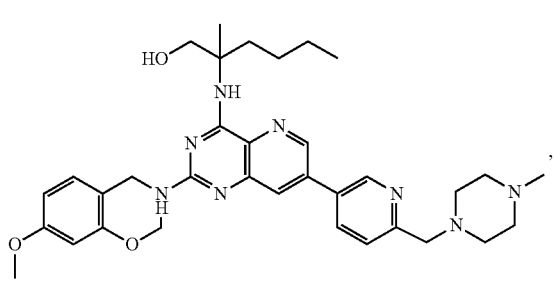
5b,

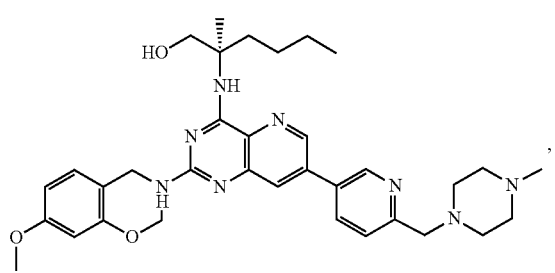
6b,

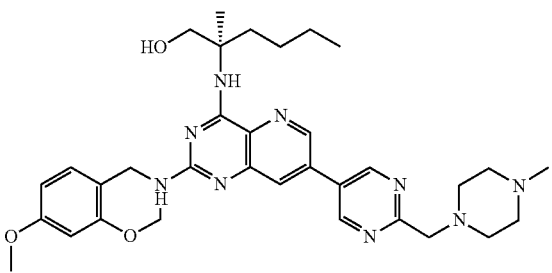
7d,

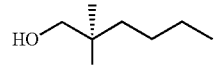
8e

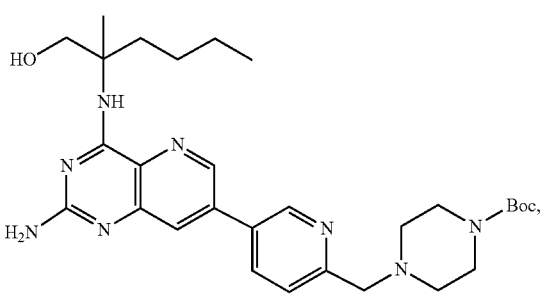
and

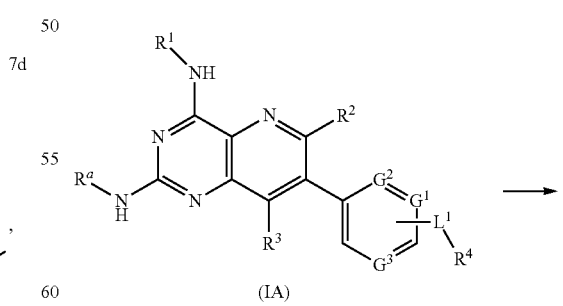
9d or a tautomer, mesomer, racemate, enantiomer, diastereomer thereof, or mixture thereof, or a pharmaceutically acceptable salt thereof.

11. The compound of formula (I) according to claim 5, wherein $R^4$ is a 4 to 6 membered heterocyclyl comprising one or two identical or different heteroatom(s) selected from the group consisting of N, O and S, and the 4 to 6 membered heterocyclyl is optionally substituted by one or more alkyl(s).

12. The compound of formula (IA) according to claim 9, wherein $R^a$ is 2,4-dimethoxybenzyl.

13. The compound of formula (I) according to claim 6, wherein $R^6$ is alkyl.

14. The compound of formula (I) according to claim 7, wherein $R^6$ is alkyl.

15. A method for preparing the compound of formula (I) according to claim 1, comprising a step of:

(IA)

-continued

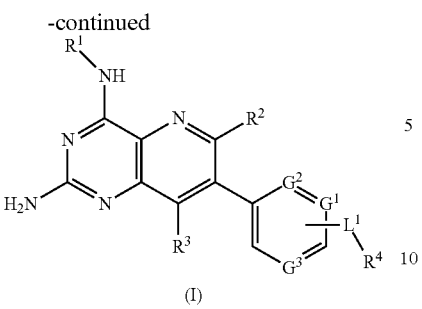

(I)

subjecting the compound of formula (IA) to a deprotection reaction to obtain the compound of formula (I);
wherein:
$R^a$ is an amino protecting group; and
$G^1$ to $G^3$, $L^1$ and $R^1$ to $R^4$ are as defined in claim 1.

16. A pharmaceutical composition, comprising a therapeutically effective amount of the compound of formula (I) according to claim 1, and one or more pharmaceutically acceptable carriers, diluents or excipients.

17. A method of activating TLR8 in a patient in need thereof, the method comprising administering to the patient a therapeutically effective amount of the compound of formula (I) according to claim 1.

18. A method of treating an infection caused by a virus in a patient in need thereof, the method comprising administering to the patient a therapeutically effective amount of the compound of formula (I) according to claim 1, wherein the virus is hepatitis B virus, hepatitis C virus, influenza virus, herpes virus and AIDS virus.

19. A method of regulating an immune system in a patient in need thereof, the method comprising administering to the patient a therapeutically effective amount of the compound of formula (I) according to claim 1.

* * * * *